United States Patent
Moskowitz et al.

(10) Patent No.: US 10,098,672 B2
(45) Date of Patent: *Oct. 16, 2018

(54) CERVICAL SPINOUS PROCESS STAPLE

(71) Applicant: Moskowitz Family LLC, Rockville, MD (US)

(72) Inventors: Mosheh T. Moskowitz, Rockville, MD (US); Ahmnon D. Moskowitz, Rockville, MD (US); Nathan C. Moskowitz, Rockville, MD (US)

(73) Assignee: Moskowitz Family LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/337,210

(22) Filed: Jul. 21, 2014

(65) Prior Publication Data
US 2015/0148847 A1   May 28, 2015

Related U.S. Application Data

(63) Continuation of application No. 13/101,135, filed on May 4, 2011, now Pat. No. 9,675,385, which is a (Continued)

(51) Int. Cl.
*A61B 17/70* (2006.01)
*A61B 17/064* (2006.01)
(Continued)

(52) U.S. Cl.
CPC ........ *A61B 17/7047* (2013.01); *A61B 17/068* (2013.01); *A61B 17/0642* (2013.01);
(Continued)

(58) Field of Classification Search
CPC ............ A61B 17/0642; A61B 17/0643; A61B 17/7047; A61B 17/7068; A61B 17/707; A61B 17/7062; A61B 2/4405
(Continued)

(56) References Cited

U.S. PATENT DOCUMENTS

| | | |
|---|---|---|
| 4,532,926 A | 8/1985 | O'Holla |
| 4,554,914 A | 11/1985 | Kapp et al. |

(Continued)

FOREIGN PATENT DOCUMENTS

| | | |
|---|---|---|
| WO | 2004093749 A1 | 11/2004 |
| WO | 2006091503 A1 | 8/2006 |

OTHER PUBLICATIONS

Vincent C. Traynelis, "Prosthetics and Biologics: The Wave of the Future," Clinical Neurosurgery, vol. 50, Proceedings of the Congress of Neurological Surgeons, Philadelphia, PA 2002, Chapter 9, pp. 207-219.

(Continued)

*Primary Examiner* — Julianna N Harvey
(74) *Attorney, Agent, or Firm* — Fish & Richardson P.C.

(57) ABSTRACT

Thoracic/lumbar and cervical spinous process staples which staple/fuse adjacent spinous processes are disclosed. Thoracic/lumbar transverse process staples which staple/fuse adjacent transverse processes are also disclosed. Each embodiment has upper and lower claws connected by a ratchet spring mechanism, along with a multiplicity of bone fastener prongs attached to the upper and lower claws. Two sets of prongs on each staple claw are spaced by a distance approximately equal to the distance separating adjacent spinous or transverse processes so as to facilitate stapling/fusion of two adjacent processes. Also disclosed are staple prongs with multiple perforations which enable incorporation of bone fusion material thereby facilitating stapling/fusion of spinal elements.

25 Claims, 47 Drawing Sheets

Related U.S. Application Data continuation-in-part of application No. 12/471,345, filed on May 22, 2009, now Pat. No. 8,257,370, which is a continuation of application No. 12/054,335, filed on Mar. 24, 2008, now Pat. No. 7,972,363, which is a continuation-in-part of application No. 11/842,855, filed on Aug. 21, 2007, now Pat. No. 7,942,903, application No. 14/337,210, which is a continuation of application No. 13/101,135, filed on May 4, 2011, now Pat. No. 9,675,385, which is a continuation-in-part of application No. 12/471,340, filed on May 22, 2009, now Pat. No. 8,734,516, application No. 14/337,210, which is a continuation of application No. 13/101,135, filed on May 4, 2011, now Pat. No. 9,675,385, which is a continuation-in-part of application No. 12/054,335, filed on Mar. 24, 2008, now Pat. No. 7,972,363, which is a continuation-in-part of application No. 11/842,855, filed on Aug. 21, 2007, now Pat. No. 7,942,903, application No. 14/337,210, which is a continuation of application No. 13/101,135, filed on May 4, 2011, now Pat. No. 9,675,385, which is a continuation-in-part of application No. 11/842,855, filed on Aug. 21, 2007, now Pat. No. 7,942,903, application No. 14/337,210, which is a continuation of application No. 13/101,135, filed on May 4, 2011, now Pat. No. 9,675,385, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279, application No. 14/337,210, which is a continuation of application No. 13/101,135, filed on May 4, 2011, now Pat. No. 9,675,385, which is a continuation-in-part of application No. 11/208,644, filed on Aug. 23, 2005, now Pat. No. 7,704,279, application No. 14/337,210, which is a continuation of application No. 13/101,135, filed on May 4, 2011, now Pat. No. 9,675,385, application No. 14/337,210, which is a continuation of application No. 13/101,135, filed on May 4, 2011, now Pat. No. 9,675,385, application No. 14/337,210, which is a continuation of application No. 13/101,129, filed on May 4, 2011, now Pat. No. 8,784,450, and a continuation of application No. 14/257,650, filed on Apr. 21, 2014, now Pat. No. 9,622,875.

(60) Provisional application No. 60/670,231, filed on Apr. 12, 2005, provisional application No. 61/419,679, filed on Dec. 3, 2010, provisional application No. 61/425,749, filed on Dec. 21, 2010.

(51) Int. Cl.
| | |
|---|---|
| *A61B 17/068* | (2006.01) |
| *A61F 2/44* | (2006.01) |
| *A61F 2/46* | (2006.01) |
| *A61B 17/80* | (2006.01) |
| *A61F 2/28* | (2006.01) |
| *A61F 2/30* | (2006.01) |

(52) U.S. Cl.
CPC ...... *A61B 17/0643* (2013.01); *A61B 17/7065* (2013.01); *A61F 2/447* (2013.01); *A61F 2/4637* (2013.01); *A61B 17/809* (2013.01); *A61B 2017/0641* (2013.01); *A61B 2017/0647* (2013.01); *A61B 2017/0648* (2013.01); *A61F 2002/2835* (2013.01); *A61F 2002/305* (2013.01); *A61F 2002/30331* (2013.01); *A61F 2002/30383* (2013.01); *A61F 2002/30476* (2013.01); *A61F 2002/30772* (2013.01); *A61F 2002/30787* (2013.01); *A61F 2002/30879* (2013.01); *A61F 2002/448* (2013.01); *A61F 2002/4622* (2013.01); *A61F 2002/4641* (2013.01); *A61F 2220/0025* (2013.01); *A61F 2220/0033* (2013.01)

(58) Field of Classification Search
USPC .................. 606/248, 249, 75, 324, 247
See application file for complete search history.

(56) References Cited

U.S. PATENT DOCUMENTS

| | | | |
|---|---|---|---|
| 4,599,086 A | 7/1986 | Doty | |
| 4,636,217 A | 1/1987 | Ogilvie et al. | |
| 4,852,558 A | 8/1989 | Outerbridge | |
| 4,960,420 A | 10/1990 | Goble et al. | |
| 4,976,722 A * | 12/1990 | Failla | A61B 17/122 |
| | | | 606/151 |
| 4,997,432 A | 3/1991 | Keller | |
| 5,002,552 A * | 3/1991 | Casey | A61F 6/206 |
| | | | 251/9 |
| 5,005,749 A | 4/1991 | Aranyi | |
| 5,062,850 A | 11/1991 | Macmillan et al. | |
| 5,123,926 A | 6/1992 | Pisharodi | |
| 5,290,312 A | 3/1994 | Kojimoto et al. | |
| 5,405,391 A | 4/1995 | Henderson et al. | |
| 5,413,583 A | 5/1995 | Wohlers | |
| 5,454,819 A | 10/1995 | Knoepfler | |
| 5,514,180 A | 5/1996 | Heggeness et al. | |
| 5,660,188 A | 8/1997 | Groiso | |
| 5,667,472 A | 9/1997 | Finn et al. | |
| 5,782,832 A | 7/1998 | Larsen et al. | |
| 5,865,848 A | 2/1999 | Baker | |
| 5,888,223 A | 3/1999 | Bray, Jr. | |
| 5,951,574 A | 9/1999 | Stefanchik et al. | |
| 5,960,522 A | 10/1999 | Boe | |
| 6,026,827 A * | 2/2000 | Revais | A45D 8/20 |
| | | | 132/133 |
| 6,126,689 A | 10/2000 | Brett | |
| 6,312,431 B1 | 11/2001 | Asfora | |
| 6,342,074 B1 | 1/2002 | Simpson | |
| 6,368,350 B1 | 4/2002 | Erickson et al. | |
| 6,375,682 B1 | 4/2002 | Fleischmann et al. | |
| 6,419,704 B1 | 7/2002 | Ferree | |
| 6,432,106 B1 | 8/2002 | Fraser | |
| 6,458,159 B1 | 10/2002 | Thalgott | |
| 6,527,804 B1 | 3/2003 | Gauchet et al. | |
| 6,533,818 B1 | 3/2003 | Weber et al. | |
| 6,558,423 B1 | 5/2003 | Michelson | |
| 6,572,653 B1 | 6/2003 | Simonson | |
| 6,579,318 B2 | 6/2003 | Varga et al. | |
| 6,582,468 B1 | 6/2003 | Gauchet | |
| 6,613,055 B2 | 9/2003 | Di Emidio | |
| 6,629,998 B1 | 10/2003 | Lin | |
| 6,641,614 B1 | 11/2003 | Wagner et al. | |
| 6,719,794 B2 | 4/2004 | Gerber | |
| 6,723,126 B1 | 4/2004 | Berry | |
| 6,733,532 B1 | 5/2004 | Gauchet et al. | |
| 6,764,491 B2 | 7/2004 | Frey et al. | |
| 6,770,094 B2 | 8/2004 | Fehling et al. | |
| 6,786,070 B1 * | 9/2004 | Dimig | E05B 77/30 |
| | | | 292/201 |
| 6,824,564 B2 | 11/2004 | Crozet | |
| 6,852,117 B2 * | 2/2005 | Orlowski | A61B 17/122 |
| | | | 606/120 |
| 6,904,308 B2 | 6/2005 | Frisch et al. | |
| 6,953,477 B2 | 10/2005 | Berry | |
| 6,955,671 B2 | 10/2005 | Uchikubo | |
| 6,972,019 B2 | 12/2005 | Michelson | |
| 7,030,904 B2 | 4/2006 | Adair et al. | |
| 7,033,394 B2 | 4/2006 | Michelson | |
| 7,037,258 B2 | 5/2006 | Chatenever et al. | |

(56) References Cited

U.S. PATENT DOCUMENTS

| | | |
|---|---|---|
| 7,097,615 B2 | 8/2006 | Banik et al. |
| 7,211,112 B2 | 5/2007 | Baynham et al. |
| 7,326,248 B2 | 2/2008 | Michelson |
| 7,442,209 B2 | 10/2008 | Michelson |
| 7,476,251 B2 | 1/2009 | Zucherman et al. |
| 7,615,059 B2 | 11/2009 | Watschke et al. |
| 7,704,279 B2 | 4/2010 | Moskowitz et al. |
| 7,862,616 B2 | 1/2011 | Lechmann et al. |
| 8,034,060 B2 | 10/2011 | Keren et al. |
| 8,206,420 B2 | 6/2012 | Patel et al. |
| 8,267,300 B2 | 9/2012 | Boudreaux |
| 8,328,872 B2 | 12/2012 | Duffield et al. |
| 8,403,986 B2 | 3/2013 | Michelson |
| 8,784,450 B2 | 7/2014 | Moskowitz |
| 9,179,944 B2 | 11/2015 | Boyer, II |
| 9,675,385 B2 * | 6/2017 | Moskowitz ........ A61B 17/0642 |
| 2002/0068977 A1 | 6/2002 | Jackson |
| 2002/0143338 A1 | 10/2002 | Orbay et al. |
| 2003/0040746 A1 | 2/2003 | Mitchell et al. |
| 2003/0216736 A1 * | 11/2003 | Robinson ........... A61B 17/7068 606/86 B |
| 2004/0088054 A1 | 5/2004 | Berry |
| 2004/0177531 A1 | 9/2004 | DiBenedetto et al. |
| 2004/0254644 A1 | 12/2004 | Taylor |
| 2005/0027362 A1 | 2/2005 | Williams et al. |
| 2005/0049590 A1 | 3/2005 | Alleyne et al. |
| 2005/0075634 A1 | 4/2005 | Zucherman et al. |
| 2005/0102028 A1 | 5/2005 | Arnin et al. |
| 2005/0177235 A1 | 8/2005 | Baynham et al. |
| 2005/0216084 A1 | 9/2005 | Fleischmann |
| 2005/0273170 A1 | 12/2005 | Navarro et al. |
| 2005/0278026 A1 | 12/2005 | Gordon et al. |
| 2006/0247640 A1 | 11/2006 | Blackwell et al. |
| 2007/0093830 A1 | 4/2007 | Zucherman et al. |
| 2007/0161992 A1 | 7/2007 | Kwak et al. |
| 2007/0213820 A1 | 9/2007 | Magerl et al. |
| 2007/0233082 A1 * | 10/2007 | Chin .................. A61B 17/7065 606/276 |
| 2008/0294206 A1 | 11/2008 | Choi et al. |
| 2009/0054988 A1 | 2/2009 | Hess |
| 2009/0062869 A1 | 3/2009 | Claverie et al. |
| 2009/0105831 A1 | 4/2009 | Jones et al. |
| 2009/0163920 A1 | 6/2009 | Hochschuler et al. |
| 2010/0087860 A1 | 4/2010 | Chin et al. |
| 2010/0145460 A1 | 6/2010 | McDonough et al. |
| 2011/0022090 A1 | 1/2011 | Gordon |
| 2011/0066186 A1 | 3/2011 | Boyer et al. |
| 2012/0029636 A1 | 2/2012 | Ragab et al. |
| 2012/0150228 A1 | 6/2012 | Zappacosta |

OTHER PUBLICATIONS

E.K. Wai et al., "Disk Replacement Arthroplasties: Can The Success of Hip and Knee Replacements be Repeated in the Spine?," Seminars in Spine Surgery, vol. 15, No. 4 Dec. 2003, pp. 473-482.

Richard D. Guyer et al., "Intervertebral Disc Prostheses," Spine Journal, vol. 28, No. 15S, Supp. to Aug. 1, 2003, pp. S15-S23.

Dieter Grob et al., "Clinical Experience With the Dynesys Semirigid Fixation System for the Lumbar Spine," SPINE, vol. 30, No. 3, 2005, pp. 324-331.

International Search Report (ISR) and Written Opinion of the International Searching Authority, dated Dec. 3, 2007, International Application No. PCT/US 07/05005.

International Search Report (ISR) and Written Opinion of the International Searching Authority, dated May 21, 2008, International Application No. PCT/US2007/021015.

International Search Report (ISR) and Written Opinion of the International Searching Authority, dated Jul. 9, 2008, International Application No. PCT/US2007/021013.

* cited by examiner

100c

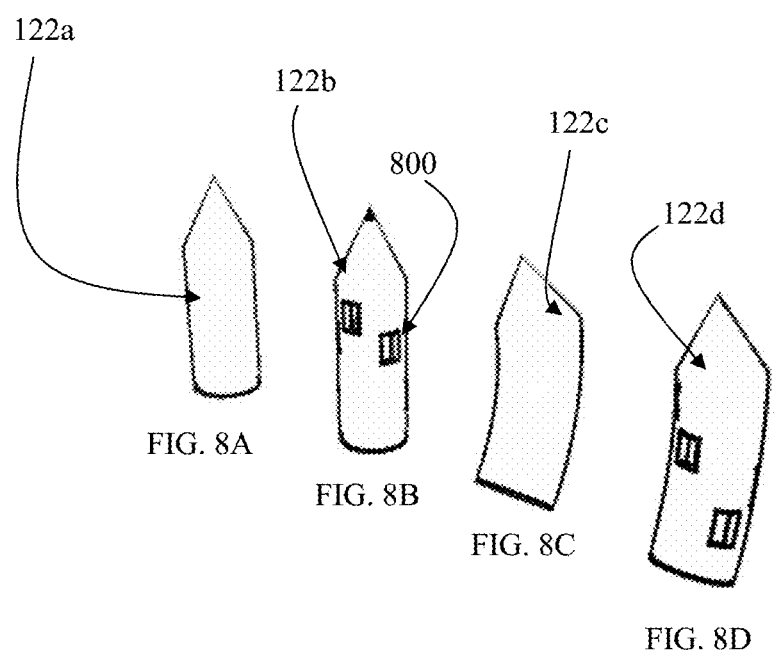

CERVICAL SPINOUS PROCESS STAPLE

CROSS-REFERENCE TO RELATED APPLICATIONS

This application is a Continuation in Part of U.S. application Ser. Nos. 13/101,135, filed May 4, 2011, Ser. No. 13/101,129, filed May 4, 2011 (now U.S. Pat. No. 8,784,450), and Ser. No. 14/257,650, filed Apr. 21, 2014 (now U.S. Pat. No. 9,622,875).

Application Ser. No. 13/101,135 claims priority to U.S. Provisional Application Nos. 61/425,749, filed Dec. 21, 2010 and Ser. No. 61/419,679, filed Dec. 3, 2010. Application Ser. No. 13/101,135 is a Continuation in Part of U.S. application Ser. Nos. 12/471,345, filed May 22, 2009 (now U.S. Pat. No. 8,257,370) and Ser. No. 12/471,340, filed May 22, 2009 (now U.S. Pat. No. 8,734,516).

Application Ser. No. 12/471,345 is a Continuation in Part of U.S. application Ser. No. 12/054,335, filed Mar. 24, 2008 (now U.S. Pat. No. 7,972,363), which is a Continuation in Part of U.S. application Ser. No. 11/842,855, filed Aug. 21, 2007 (now U.S. Pat. No. 7,942,903).

FIELD OF DISCLOSURE

The present invention relates to stand-alone or supplemental cervical, thoracic and lumbosacral Spinous Process (SP) interarticulating staples, and thoracic/lumbosacral Transverse Process (TP) interarticulating staples. Both the SP and TP interarticulating staples can be surgically implanted and function independently as stand-alone spinal segmental fusion devices and/or can be employed supplementally in tandem with each other, and/or supplementally in tandem with facet joint (FJ) interarticulating staples according to the above-referenced related applications of Applicants, and/or supplementally with other known fusion devices to achieve stable spinal fusion. The embodiments of these inventions may obviate and/or lessen the need for posterior supplemental pedicle screw fixation, as well as anterior or lateral plate fixation/instrumentation, and thereby achieve a safer and more minimally invasive method of achieving spinal segmental fixation/fusion.

The present invention also relates to staple prongs with multiple perforations which allow packing of bone and/or bone growth material within the prongs thereby facilitating the integration/fusion of the device to the spine, minimizing and/or preventing implant extrusion, and promoting bone fusion.

BACKGROUND

The history and evolution of instrumented spinal fusion in the entire human spine has been reviewed in related pending application Ser. No. 12/471,345, filed on May 22, 2009, application Ser. No. 12/471,340, filed on May 22, 2009, Ser. No. 12/054,335 filed on Mar. 24, 2008, Ser. No. 11/842,855, filed on Aug. 21, 2007, Ser. No. 11/536,815 filed on Sep. 29, 2006, and Ser. No. 11/208,644 filed on Aug. 23, 2005, the contents of which are hereby incorporated by reference in their entirety.

Conventionally, the majority of posterior cervical, and posterior and lateral, thoracic and lumbosacral fusion techniques, as well as anterior and/or lateral thoracic/lumbosacral fusion techniques are typically supplemented with pedicle screw placement.

Complications of pedicle screw placement in the spine include duration of procedure, significant tissue dissection and muscle retraction, misplaced screws with neural and/or vascular injury, excessive blood loss, need for transfusions, prolonged recovery, incomplete return to work, and excessive rigidity leading to adjacent segmental disease requiring further fusions and re-operations.

Recent advances in pedicle screw fixation including minimally invasive, and stereotactic CT image-guided technology, and the development of flexible rods, imperfectly address some but not all of these issues.

Complications of anterior plating/instrumentation in the anterior lumbar spine include potential devastating injury to the major vessels due to chronic vascular erosion of major vessels, or acute vascular injuries due to partial or complete plate and or screw pull-out. Recent advances including diminishing plate width and/or profile, and absorbable plates/screws, imperfectly address some, but not all of these issues.

Furthermore, for re-do surgeries, plate removal can be arduous with potential complications of vascular, and/or neural injury and screw breakage.

Lateral access to the lumbosacral spine can be complicated by damage to the genitofemoral nerve. Sensory and motor evoked potential monitoring during this surgery imperfectly address some but not all of these issues.

SUMMARY

The above-referenced related applications of Applicants describe spinal facet joint (FJ) interarticulating staples that address and attempt to improve or resolve the above problems and issues. The exemplary embodiments of the invention described herein are modifications of the facet joint (FJ) stapling device of the above-referenced related applications of Applicants and which are specifically adapted to execute adjacent spinal level Spinous Process (SP) and Transverse Process (TP) segmental fixation/fusion and which further address, improve upon, and/or resolve the above-referenced problems. The exemplary embodiments can further minimize and/or avoid transpedicular, anterior, and lateral spinal fusion instrumentation techniques and thereby avoid their concomitant complications and disadvantages which are detailed above. These exemplary embodiments continue to advance minimally invasive and low risk spinal device technology.

Herein described are multiple exemplary spinal fusion device embodiments of Spinous Process (SP) and Transverse Process (TP) interarticulating staples. These embodiments are exemplarily described for thoracic/lumbosacral SP interarticulating staples, thoracic/lumbosacral TP interarticulating staples, and cervical SP interarticulating staples.

For example, two broadly distinct SP staple embodiments are described; one for thoracic/lumbosacral SP fusion, and one for cervical SP fusion. These two distinctly designed embodiments take into account the inherent anatomical differences between cervical and lumbar SP size, geometry, topography, bone thickness and inter-spinous process distance(s).

Likewise the design of the thoracic/lumbosacral Transverse Process (TP) interarticulating staple embodiment takes into account the unique inter-TP distance(s), and the geometric contour, topography, and bone thickness of the TP compared to the SP elements.

The present disclosure recognizes the aforementioned problems with conventional apparatuses and solves these problems by, among other things, improving upon the designs illustrated in the aforementioned related applications. The present disclosure provides an advanced minimally invasive and low risk method of segmental spinal fusion via the use of interarticulating SP and TP stapling devices.

The exemplary embodiments of SP and TP fixating stapling devices described herein, and the FJ stapling device, described in the above-referenced related applications of Applicants, each can independently or in various combinations of co-supplemental application provide as strong or stronger segmental fusion as pedicle screws without the complications arising from pedicle screw placement, which include screw misplacement with potential nerve and/or vascular injury, violation of healthy facets, possible pedicle destruction, blood loss, and overly rigid fusions.

The stapling/fusion of adjacent SPs and/or TPs, and/or FJs can minimize or avoid, and hence minimize or prevent, destruction of healthy facet joints. Because the embodiments avoid fusion of anterior, middle and posterior columns, as do pedicle screws, the exemplary embodiments in essence create more flexible, i.e. less rigid, fusion, and hence diminish the possibility of adjacent level disease, and thus the probability of further operations requiring fusion extensions, i.e. re-operations.

The present disclosure recognizes that the very advantage of transpedicular screws which facilitate a strong solid fusion by rigidly engaging all three spinal columns is the same mechanical mechanism whereby complete inflexibility of all columns is incurred, thereby leading to increasing rostral and caudal segmental stress which leads to increased rates of reoperation.

The present disclosure also recognizes that SP and TP stapling/fusion whether performed via open, endoscopic, or percutaneous fluoroscopically guided surgical techniques lead to a more flexible fusion, far less muscle retraction, blood loss and significant reduction in operating room time. Thus, the complication(s) of pedicle screw pull-out, and hence the high re-operation rate associated with conventional flexible pedicle screws/rods is obviated. Although one could opt to supplement these constructs with pedicle screws, there would be no absolute need to do so with the operative devices described herein.

The exemplary embodiments for both SP and TP staples can be used to perform multiple levels of fusion engaging a series of adjacent pair of SPs and TPs with one staple per unit of two adjacent elements. These embodiments can be employed to adjoin (fuse) multiple levels of SPs and TPs in incremental spinal process units of two.

Both SP and TP staples can also be modified (elongated) to staple/fuse three or more spinal elements using a single staple.

The further advantages of SP and TP stapling throughout the spine include speed and safety. Insertion of these devices does not involve and hence does not traverse neural/vascular structures, and hence the risk of neural or vascular injury is entirely avoided.

The relative speed of insertion, and safety of these devices conferred by their capacity to be inserted via percutaneous, open, or minimally invasive techniques, with or without endoscopic or fluoroscopic guidance, minimizes overall surgical risks. Thus, the performance of SP and TP stapling/fusion is amenable to an outpatient setting which would alleviate the economic burden of spinal fusion surgery.

For example, in an exemplary embodiment, a thoracic/lumbosacral Spinous Process (SP) staple may include a top claw and a bottom claw with a plurality of ridges, a staple pin pivotally connecting the top claw and the bottom claw, and a ratchet mechanism that limits an opening force of the top claw with respect to the bottom claw. The ratchet mechanism may include a ratchet pin pivotably-mounted to the top claw, wherein the claws can include a plurality of claw teeth which interdigitate with each other, and the ratchet pin can include a flexure spring engaging the plurality of ratchet teeth. The plurality of claw ridges can help incorporate the staple into the bone.

The top and bottom claws of the staple may also include a plurality of prongs. Further, two sets of upper and lower claw prongs may be utilized to penetrate each thoracic/lumbosacral SP. The distance between the two sets of upper and lower claw prongs can be the average distance between the lumbar SPs. The two sets of upper and lower claw prongs can be manufactured with varying interspinous distances accounting for varying intra and inter-patient anatomical differences.

In an exemplary embodiment, a total of sixteen prongs may be utilized; eight prongs per SP unit. Further, a total of eight prongs on the upper claw and eight prongs on the lower jaw may be utilized; four prongs on the upper claw for penetration of each SP and four prongs on the lower claw for penetration of each SP. Upon clamping (e.g., completely clamping) the staple on two adjacent SPs, a total of eight prongs can penetrate each SP; four from the upper claw, and four from the bottom claw. The two sets of prongs per SP unit can be spaced apart on the upper and lower claws at a distance equal to the interspinous process distance such that the claws will engage and perforate each adjacent SP.

Other exemplary embodiments of staple prongs, including solid-straight, solid-curved, perforated-straight and perforated-curved are described herein and are contemplated by the present invention.

The perforated prongs may include multiple perforations within the prongs themselves which can allow the packing of autologous, or allograft bone, bone putty, bone morphogenic protein, bmp, bone marrow aspirate or any biological or synthetic material which promotes bone fusion. Further, these embodiments can facilitate integration of the device into the bone and promote bony fusion.

The exemplary embodiments having curved or straight prong(s) can be selected based on anatomical variations and surgical preference.

In another exemplary embodiment, a thoracic/lumbosacral Transverse Process (TP) staple may include a top claw and a bottom claw with a plurality of ridges, a staple pin pivotally connecting the top claw and the bottom claw, and a ratchet mechanism that limits an opening force of the top claw with respect to the bottom claw. The ratchet mechanism may include a ratchet pin pivotably mounted to the top claw. The claws may include a plurality of interdigitating claw teeth, and the ratchet pin can include a flexure spring engaging the plurality of ratchet teeth. The plurality of claw ridges can help incorporate the staple into the bone.

The top and bottom claws of the TP staple may also include a plurality of prongs. Further, there may be two sets of upper and lower claw prongs which can penetrate each TP unit. The distance between the two sets of prongs on the upper and lower claws can be the average distance between lumbar TPs. The two sets of upper and lower claw prongs can be manufactured with varying inter-TP distances accounting for varying intra and inter-patient anatomical differences. The staple claws can be contoured to hug the transverse processes and can have two sets of prongs separated by the inter-TP distance. In an embodiment, four prongs may penetrate each TP unit; two prongs can be located on the upper claw and two opposing prongs can be located on the lower claw which may engage and perforate each TP. When the staple is clamped (i.e., fully clamped or closed) on two adjacent TPs, a total of four prongs can engage each TP.

Other exemplary embodiments of staple prongs, including solid-straight, solid-curved, perforated-straight and perforated-curved are described herein and are contemplated by the present invention.

An embodiment having perforated prongs may include multiple perforations within the prongs themselves which can allow the packing of autologous, or allograft bone, bone putty, bone morphogenic protein, bmp, bone marrow aspirate or any biological or synthetic material which promotes fusion. These embodiments may facilitate integration of the device into the bone thereby facilitating bony fusion.

Embodiments having curved or straight prong(s) can be selected based on anatomical variations and surgical preference.

In another exemplary embodiment, a cervical Spinous Process (SP) staple may include a top claw and a bottom claw including a plurality of ridges, a staple pin pivotally connecting the top claw and the bottom claw, and a ratchet mechanism that can limit an opening force of the top claw with respect to the bottom claw. The ratchet mechanism may include a ratchet pin pivotally mounted to the top claw. The claws can include a plurality of claw teeth, and the ratchet pin may include a flexure spring engaging the plurality of ratchet teeth. The plurality of ridges may help incorporate the staple into the bone.

The cervical SP staple may be formed to hug the contour of the SPs. Further, the cervical SP staple can be inserted from above because of the limited interspinous distance. The two opposing proximal elements of the cervical staple may be curved to avoid depressing the tips of the spinous processes, and the claws can be contoured to be flush with any unique cervical spinous process slope and geometry.

The top and bottom claws of the cervical staple may include a plurality of prongs. The cervical staple may include two sets of upper and lower claw prongs for penetration of each cervical SP. The distance between the upper and lower sets of prongs can be the average distance between two adjacent cervical SPs, and can be manufactured with varying interspinous distances accounting for varying intra and inter-patient anatomical differences. The cervical staple may include four prongs within the staple. The cervical staple may include two sets of prongs; one set per penetration of each SP. For each set, one prong can be located on the upper claw and one prong can be located on the lower claw. When the staple is closed (i.e., clamped), two prongs may engage/penetrate each cervical SP; one from the top claw, and one from the lower claw.

Other exemplary embodiments of staple prongs, including solid-straight, solid-curved, perforated-straight and perforated-curved are described herein and are contemplated by the present invention.

The perforated prongs may include multiple perforations within the prongs themselves which can allow the packing of autologous, or allograft bone, bone putty, bone morphogenic protein, bmp, bone marrow aspirate or any biological or synthetic material which promotes fusion. These embodiments may facilitate integration of the device into the SP thereby facilitating bony fusion.

The exemplary embodiments having curved or straight prong(s) can be selected based on anatomical variations and surgical preference.

The exemplary embodiment of the Spinous Process (SP) staple with interlocking-interdigitating hemi-spacers whether performed via open, endoscopic, or percutaneous fluoroscopically guided surgical techniques when compared to a laminectomy with or without fusion entails far less muscle retraction, blood loss and significant reduction in operating room time. Thus, the complications of nerve and or vascular injury, facet joint violation, worsening spinal instability, and pedicle screw pull out, are all obviated. When compared to the X-Stop and similar devices, surgical application of this single-piece device (upon application) utilizes a solitary one-step procedure thereby enhancing its minimal invasive utility, and further economizes operating room time. It can be done under local anesthesia in an out-patient setting.

The exemplary embodiment of this device can be used to perform multiple levels of distraction engaging a series of adjacent pair of SPs with one staple per unit of two adjacent elements. These embodiments can be employed to adjoin, separate and distract multiple levels of SPs in incremental spinal process units of two.

For example, an exemplary embodiment of the SP staple with interlocking-interdigitating hemi-spacers may include a top claw and a bottom claw with a plurality of ridges, a staple pin pivotally connecting the top claw and the bottom claw, and a ratchet mechanism that limits an opening force of the top claw with respect to the bottom claw. The ratchet mechanism includes a ratchet pin pivotally mounted to the top claw, wherein the claws include a plurality of claw teeth which interdigitate with each other, and wherein the ratchet pin includes a flexure spring engaging the plurality of ratchet teeth. The plurality of claw ridges helps incorporate it into the bone.

The staple's top and bottom claws may also include a plurality of prongs. Further, there may be two sets of upper and lower claw prongs designed for penetration of each SP. The distance between these two sets of prongs is the average distance between lumbar SPs. The staple can be manufactured with varying interspinous distances to address varying intra and inter-patient anatomical differences.

In an embodiment, a total of sixteen prongs may be utilized; eight prongs per SP unit. Further, a total of eight prongs on the upper claw and eight prongs on the lower jaw may be utilized; four prongs on the upper claw for penetration of each SP and four prongs on the lower claw for penetration of each SP. The staple on two adjacent SPs may be clamped using a total of eight prongs to penetrate each SP; four from the upper claw, and four from the bottom claw. The two sets of prongs per SP unit can be spaced apart on the upper and lower claws at a distance equal to the interspinous process distance such that the claws will engage and perforate each adjacent SP. Other embodiments may utilize multiple variations of the number and precise location of the prongs.

In between the two sets of prongs on the upper and lower claws is a rectangular hemi-spacer that can be attached to each claw with a screw and can be positioned to act as a wedge occupying the inter-spinous space in between adjacent SPs. The hemi-spacers on opposing staple claws are designed with mirror image interlocking protrusions, and protrusion receptacles allowing their co-mating and thus unification. Thus, when the upper and lower claws of the SP staple unite, and their prongs perforate adjacent SPs, the hemi-spacers interdigitate, interlock, and unite forming a single interspinous process wedge spacer which maintains separation/distraction between SPs, thereby alleviating spinal canal compression thus alleviating lumbar stenosis.

The hemi-spacers can be attached to each claw of the staple via a screw. Depending on the interspinous distance, and the degree of desired SP separation/distraction, different sized hemi-spacers can be preferentially attached to each claw to account for inter- and intra-patient anatomical variability. The size can vary in height, length and width. The staples can be manufactured with built-in non-removable hemi-spacers. The hemi-spacers may be any suitable geometric shape to achieve SP separation e.g., square, elliptical, ovoid, triangular, pentagonal, hexagonal, or others. The hemi-spacer interdigitations can also be composed of sharp penetrating prongs, of a series of horizontal or vertical extensions which can fit into corresponding slots, or any similar mating technique which can align and unite two mirror image masses. The hemi-spacers and the staple can be made of any bio-compatible material.

Furthermore the staples can be manufactured with different claw lengths and inter-spinous inter-prong distances.

In related pending application Ser. No. 12/471,345, filed on May 22, 2009, application Ser. No. 12/471,340, filed on May 22, 2009, Ser. No. 12/054,335 filed on Mar. 24, 2008, Ser. No. 11/842,855, filed on Aug. 21, 2007, Ser. No. 11,536,815 filed on Sep. 29, 2006, and Ser. No. 11/208,644 filed on Aug. 23, 2005, Applicants have described various exemplary embodiments of staple prongs, including solid-straight, solid-curved, perforated-straight and perforated-curved staple prongs.

Perforated prongs may include multiple perforations within the prongs themselves which can allow the packing of autologous, or allograft bone, bone putty, bone morphogenic protein, bmp, bone marrow aspirate or any biological or synthetic material which promotes bone fusion. Further, these embodiments can facilitate integration of the device into the bone and promote bony fusion. The curved or straight prong(s) embodiments can be selected based on anatomical variations and surgical preference. These embodiments can be applied to this staple as well. Only the solid-straight embodiment is illustrated here. The other prong embodiments are incorporated here by reference.

The exemplary embodiment of this device can be used to perform multiple levels of separation/distraction engaging a series of adjacent pair of SPs with one staple per every incremental unit of two adjacent SP elements.

Yet another exemplary embodiment is directed to a posterior lumbar facet joint staple, including a top claw, a bottom claw, a staple pin pivotally connecting the top claw and the bottom claw, and a ratchet mechanism that limits an opening force of the top claw with respect to the bottom claw.

Another exemplary embodiment is directed to a posterior cervical facet joint staple, including a staple body having a first surface extending along a longitudinal axis. The first surface includes a plurality of prongs and a groove extending along an axis that is perpendicular to the longitudinal axis and disposed at a center point along the longitudinal axis.

Another exemplary embodiment is directed to a staple gun for a posterior lumbar facet joint staple, including a handle having a first grip and a second grip, a cylinder body having a first end for receiving the posterior lumbar facet joint staple and a second end adjacent to the handle, a connector that connects the cylinder body to the handle, and a spring return mechanism that biases the first grip and the second grip back to an original position.

Yet another exemplary embodiment is directed to a staple gun for a posterior cervical facet joint staple, including a handle, a staple guide having a first end for receiving the posterior cervical facet joint staple and a second end mounted to the handle, a plurality of supports disposed on each side of the first end of the staple guide, and for engaging the posterior cervical facet joint staple, a staple plunger disposed in the staple guide. The staple plunger has a first end for contacting the posterior cervical facet joint staple and a second end that is adjacent to the handle. The plunger is translatable between a locked position and an unlocked position. The staple gun further includes a torsional spring that applies force to the second end of the plunger along a direction of translation of the plunger from the locked position to the unlocked position, and a trigger assembly mounted to the handle for releasing the torsional spring and plunger from the locked position.

Another exemplary embodiment is directed to a method of inserting a bi-directional fixating transvertebral (BDFT) screw/cage apparatus between a first vertebral body and a second vertebral body. The method includes measuring a dimension of a disc space between the first vertebral body and the second vertebral body, determining that the disc space is a posterior lumbar disc space, an anterior lumbar disc space, or an anterior cervical disc space, selecting an intervertebral cage based on the measured dimension of the disc space and based on the determination of the disc space being the posterior lumbar disc space, the anterior lumbar disc space, or the anterior cervical disc space, inserting the selected intervertebral cage into a midline of the disc space until the selected intervertebral cage is flush or countersunk relative to the first vertebral body and the second vertebral body, inserting a first screw member into a first internal screw guide of the selected intervertebral cage, inserting a second screw member into a second internal screw guide of the selected intervertebral cage, screwing the first screw member and the second screw member into the first vertebral body and the second vertebral body respectively, confirming a position and placement of the intervertebral cage relative to the first vertebral body and the second vertebral body, and locking the first screw member and the second screw member in a final position by embedding a portion of the first screw member and the second screw member into a screw locking mechanism of the selected The aforementioned related applications described a novel calibrated lumbar/thoracic stapling device which staples the inferior articulating facet of the superior spinal segment to the superior articulating facet of the inferior vertebral segment unilaterally or bilaterally, which may minimize motion until interbody fusion occurs. The present invention presents an evolved and lumbar staple gun which is far more user friendly than previously described embodiments by incorporating a new release mechanism, as described in the aforementioned related applications. This new change simplifies the earlier design, and facilitates easier insertion and removal of the staple decreasing the risk of the staple becoming loose or falling off during an operation. The exemplary staple gun thus makes posterior lumbar facet stapling far more amenable for percutaneous fluoroscopically guided surgical stapling.

The aforementioned related applications introduced a novel posterior cervical facet stapling device which staples the inferior articulating facet of the superior cervical segment with the superior articulating facet of the inferior cervical segment either unilaterally or bilaterally. The advantage of cervical facet staples is speed and safety. The risks of cervical facet pedicle screw fixation, which include nerve root and vertebral artery injuries, are completely obviated by the use of the embodiments of the present invention. Thus, cervical facet staples achieve the same function of cervical pedicle screws without the risks.

Placement of different embodiments of the cervical facet staples which include those with two or four prongs, along unilateral and/or bilateral facet joints in a modular manner, lead to different degrees of calibrated joint motion hence introducing the novel concept of calibrated cervical fusion. In the related applications, cervical facet embodiments of a highly evolved cervical staple gun for the two and four pronged cervical staples were introduced. The staple gun included a built-in trigger, trigger spring, spring hook, and return spring polyethylene cushion that improved the strength, ease and speed of staple bone penetration. In this application, the embodiments can provide more simplified and economically efficient staple guns which are very user friendly and further enhances the application of the cervical staple gun also making posterior cervical facet stapling more amenable to a non-invasive, percutaneous surgical procedure.

For example, an exemplary embodiment is directed to a posterior lumbar facet staple and a staple gun for a posterior lumbar facet staple, and a staple gun for a posterior cervical facet joint staple are provided.

Another exemplary embodiment is directed to a staple gun for a posterior lumbar facet joint staple gun, including a handle having a first grip and a second grip, a cylinder body having a first end for receiving the posterior lumbar facet joint staple and a second end adjacent to the handle, a connector that connects the cylinder body to the handle, a puller, an independent puller tip and a return spring. This embodiment is more user friendly making the staple gun easier to load, easier to use, and prevents the staple from falling off during any portion of the surgery.

Yet another exemplary embodiment is directed to a staple gun for a posterior cervical facet joint staple, including a handle, a retaining spring, a central plunger and a tip. The device can be used with a hammer to apply two or four pronged posterior cervical staples to impact them into the facets. A central button releases the staple from the spring allowing the staple gun to be reloaded.

BRIEF DESCRIPTION OF THE DRAWINGS

The accompanying drawings are presented to aid in the description of embodiments of the invention and are provided solely for illustration of the embodiments and not limitation thereof.

FIG. 8A illustrates a perspective view of the straight-solid staple prong, according to an exemplary embodiment of the invention.

FIG. 8B illustrates a perspective view of the straight-perforated staple prong, according to an exemplary embodiment of the invention.

FIG. 8C illustrates a perspective view of the curved-solid staple prong, according to an exemplary embodiment of the invention.

FIG. 8D illustrates a perspective view of the curved-perforated staple prong, according to an exemplary embodiment of the invention.

DETAILED DESCRIPTION OF THE EXEMPLARY EMBODIMENTS

Figure 1A:
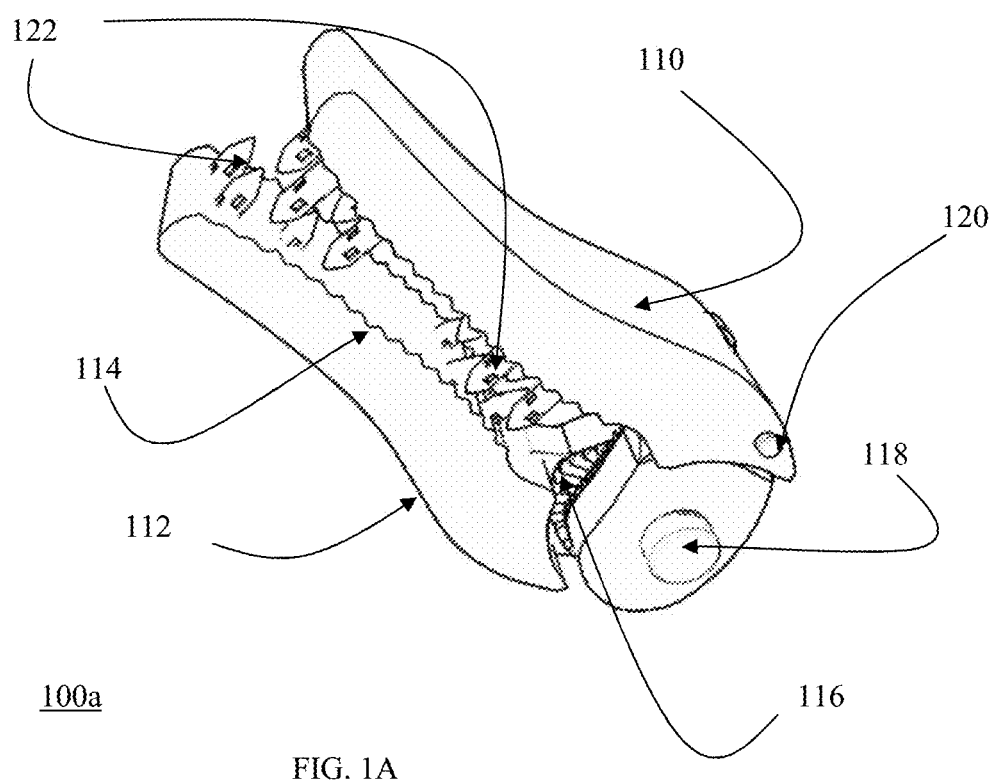
FIG. 1A illustrates a perspective (lateral) view of the thoracic/lumbosacral Spinous Process (SP) staple in a closed position, according to an exemplary embodiment of the invention.
Figure 1B:
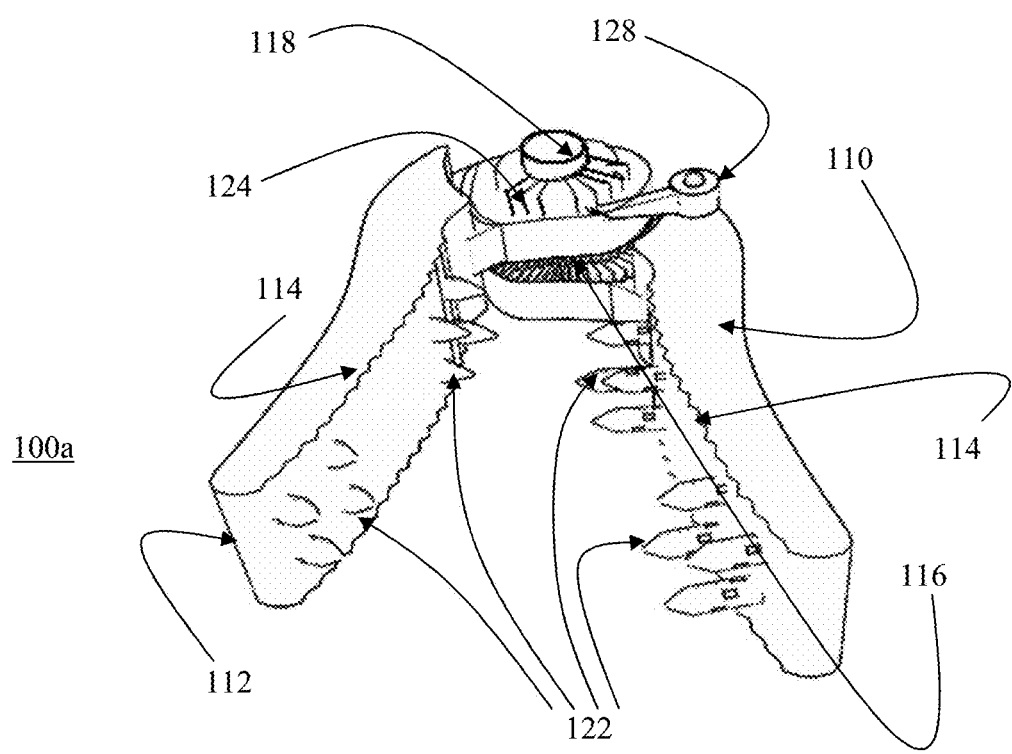
FIG. 1B illustrates a side perspective (top oblique) view of the thoracic/lumbosacral SP staple in an open position, according to an exemplary embodiment of the invention.
Figure 1C:
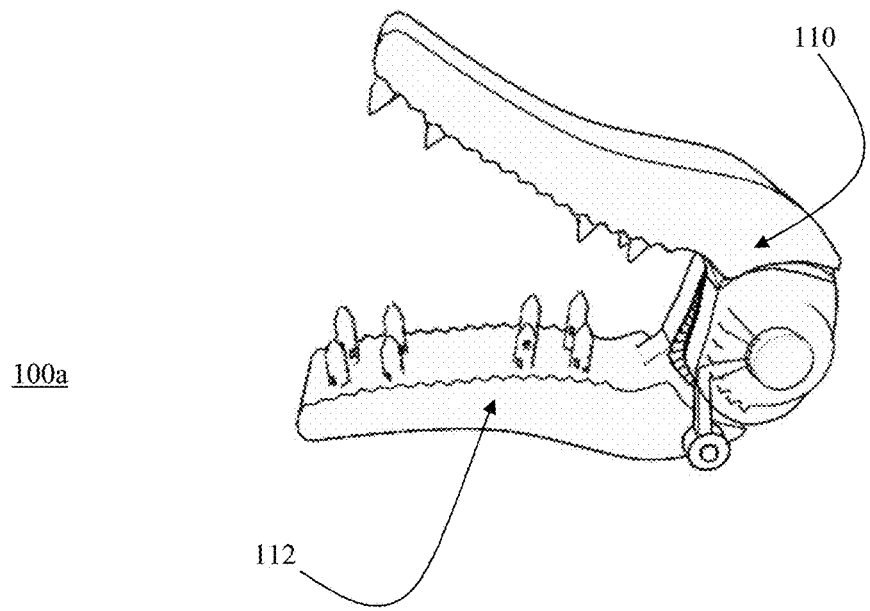
FIG. 1C illustrates a perspective (lateral) view of the thoracic/lumbosacral SP staple in an open position, according to an exemplary embodiment of the invention.
Figure 1D:
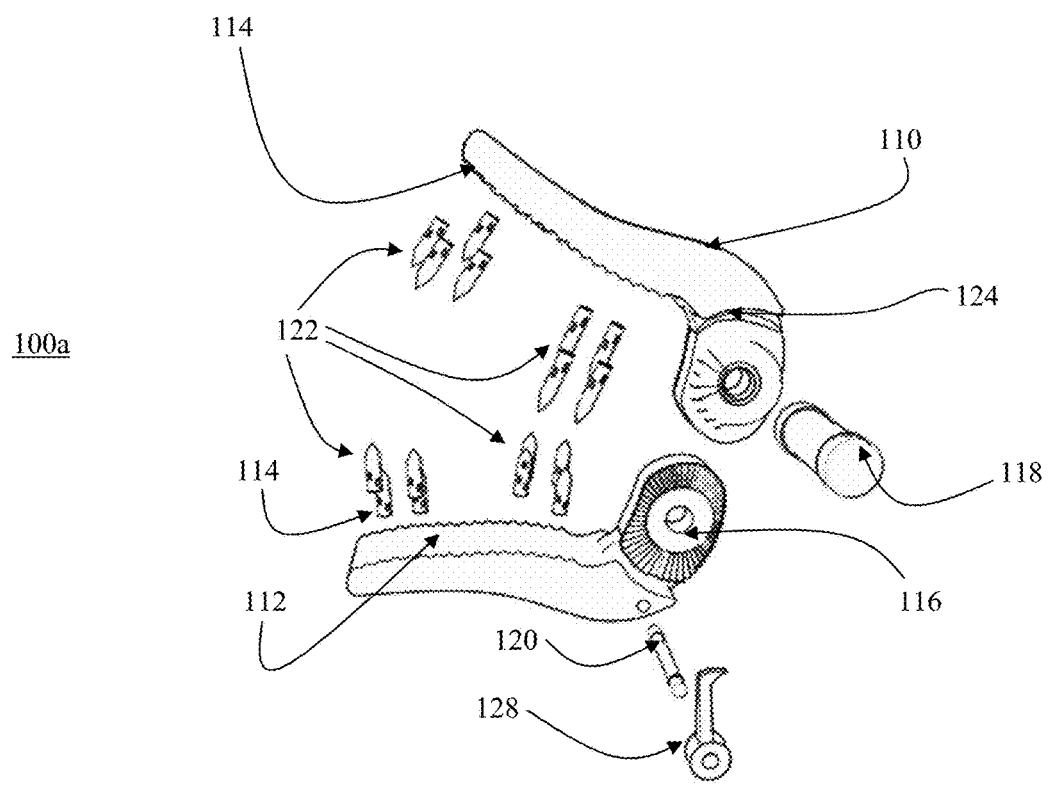
FIG. 1D illustrates an exploded view of the thoracic/lumbosacral SP staple, according to an exemplary embodiment of the invention.
Figure 2A:
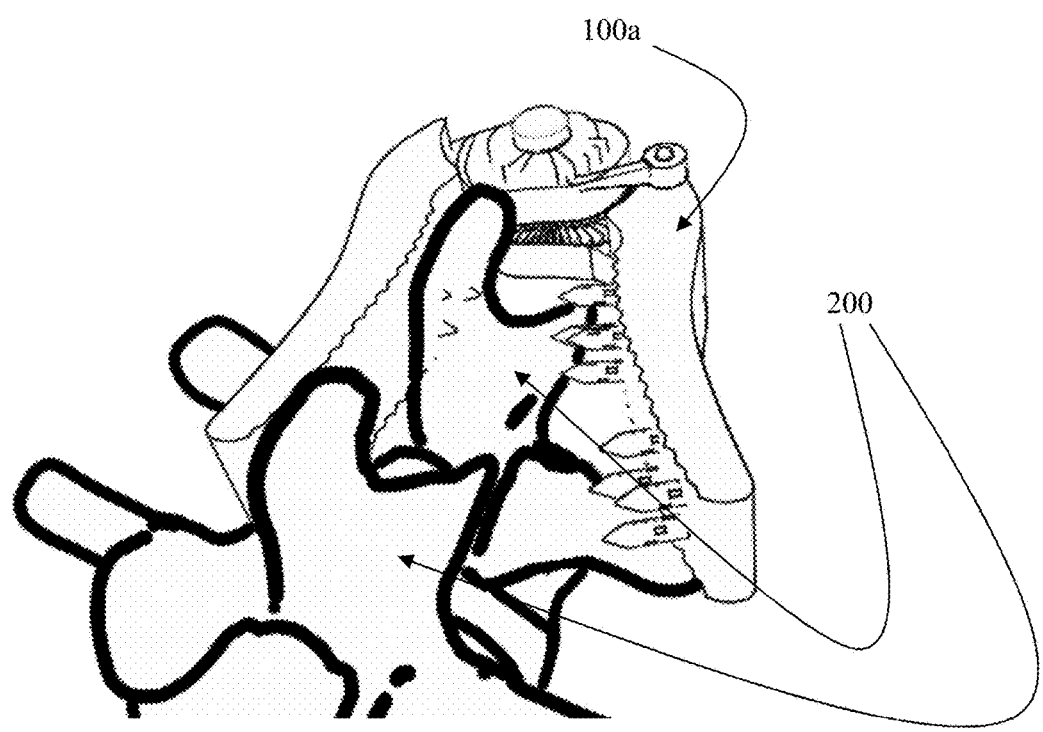
FIG. 2A illustrates a perspective (top oblique) assembly view of the lumbosacral Spinous Process (SP) staple articulating with two SPs in a partially open (partially clamped) position, according to an exemplary embodiment of the invention.
Figure 2B:
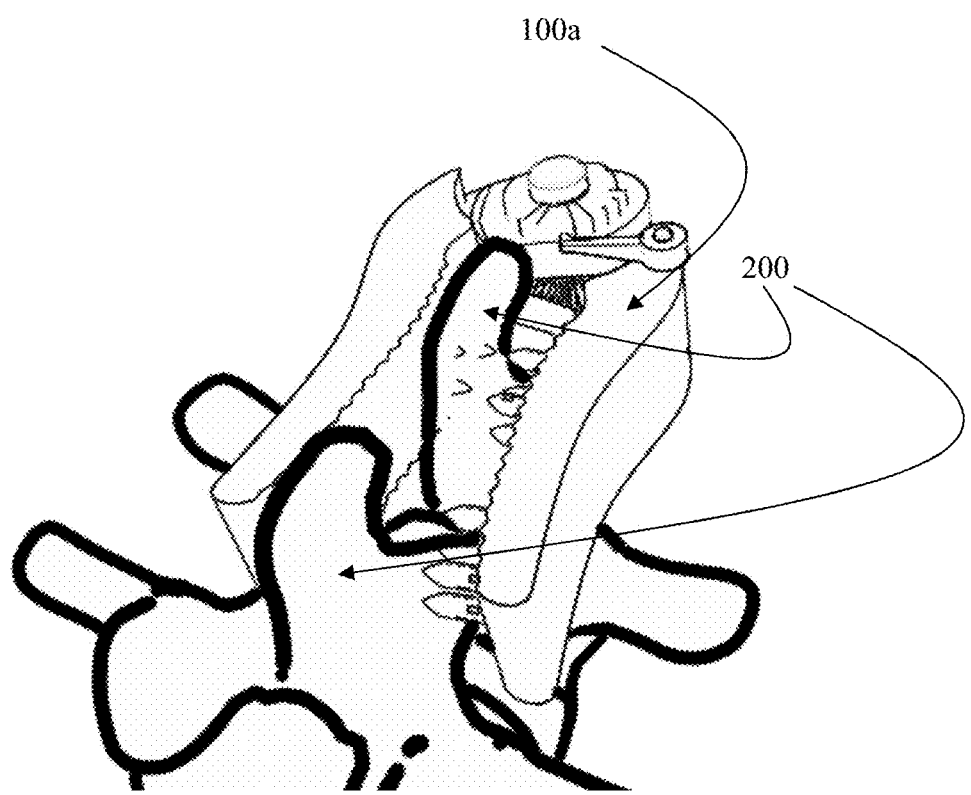
FIG. 2B illustrates a perspective (top oblique) assembly view of the lumbosacral SP staple articulating with two SPs in a partially open (partially clamped) position, according to an exemplary embodiment of the invention.
Figure 2C:
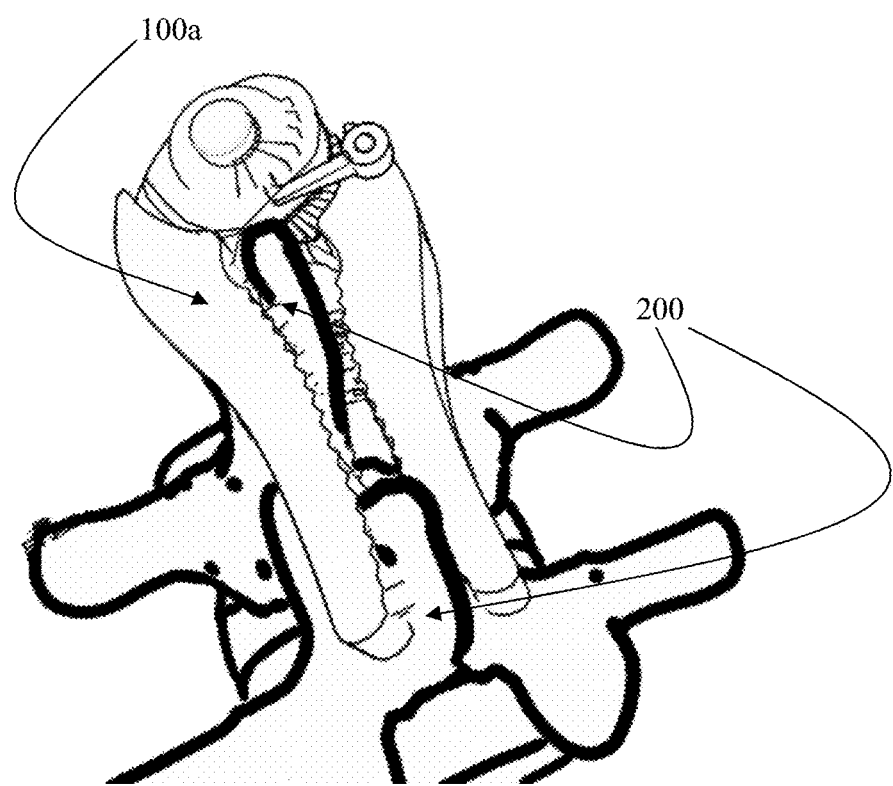
FIG. 2C illustrates a perspective (top oblique) assembly view of the lumbosacral SP staple articulating with two SPs in a closed (clamped) position, according to an exemplary embodiment of the invention.
Figure 2D:
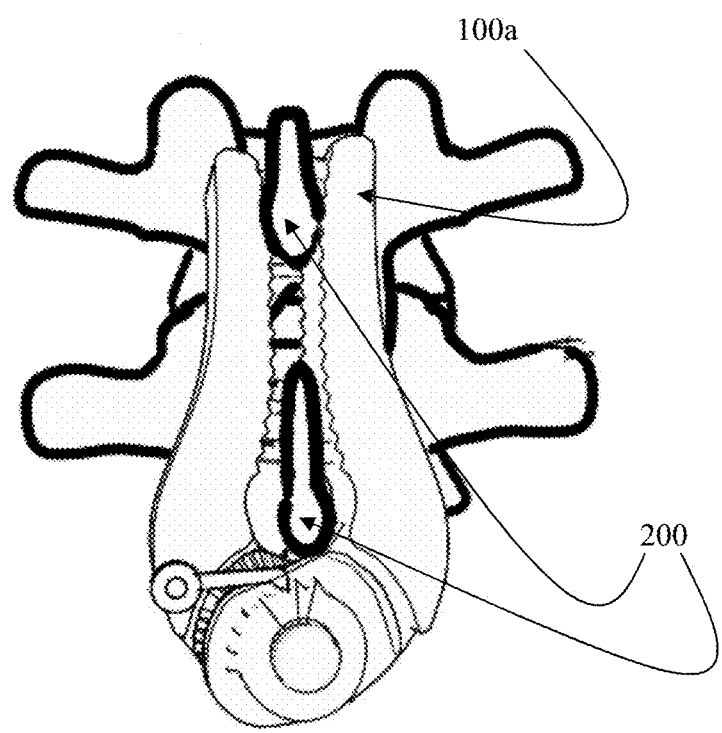
FIG. 2D illustrates a top assembly view of the lumbosacral SP staple articulating with two SPs in a closed (clamped) position, according to an exemplary embodiment of the invention.
Figure 2E:
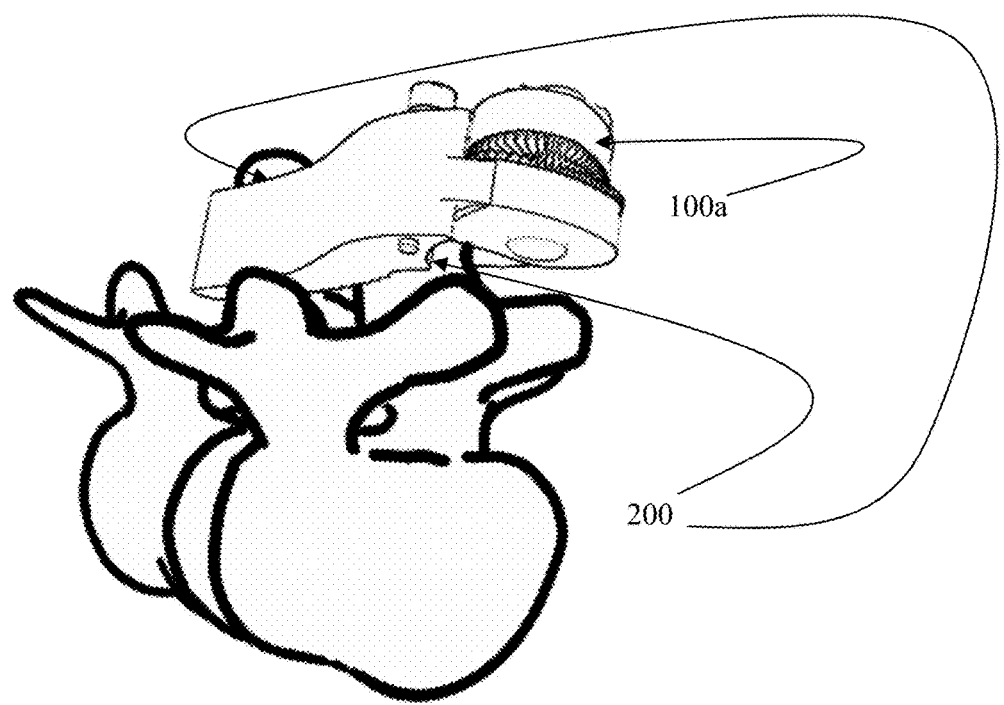
FIG. 2E illustrates a top (posterior-oblique) assembly perspective view of the lumbosacral SP staple articulating with two SPs in a closed (clamped) position, according to an exemplary embodiment of the invention.
Figure 3A:
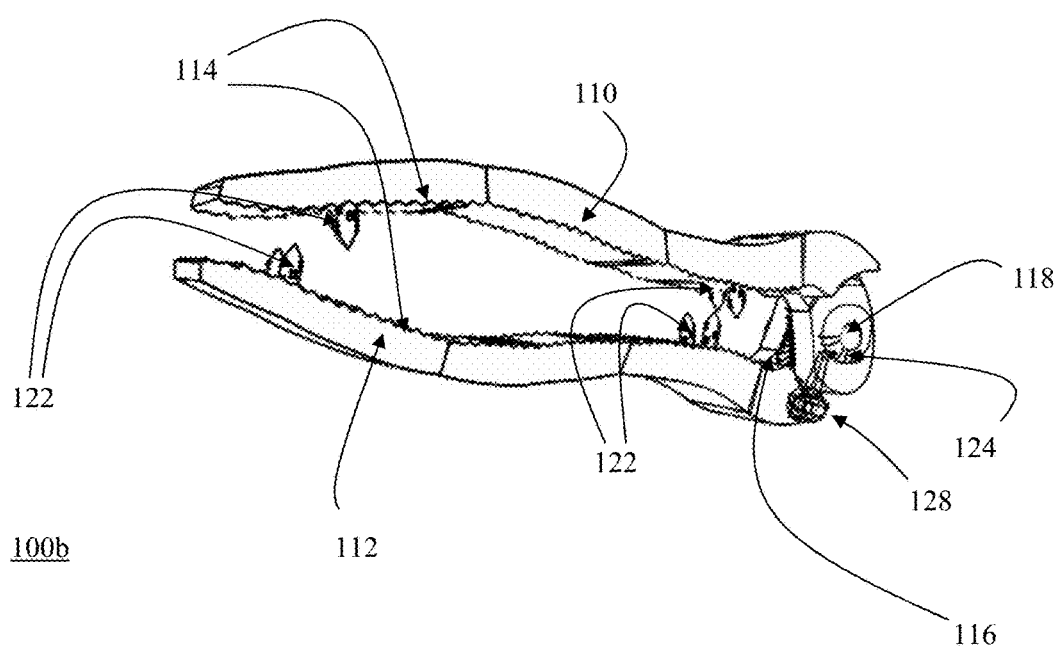
FIG. 3A illustrates a perspective (lateral) view of the thoracic/lumbosacral Transverse Process (TP) staple in a partially closed (partially clamped) position, according to an exemplary embodiment of the invention.
Figure 3B:
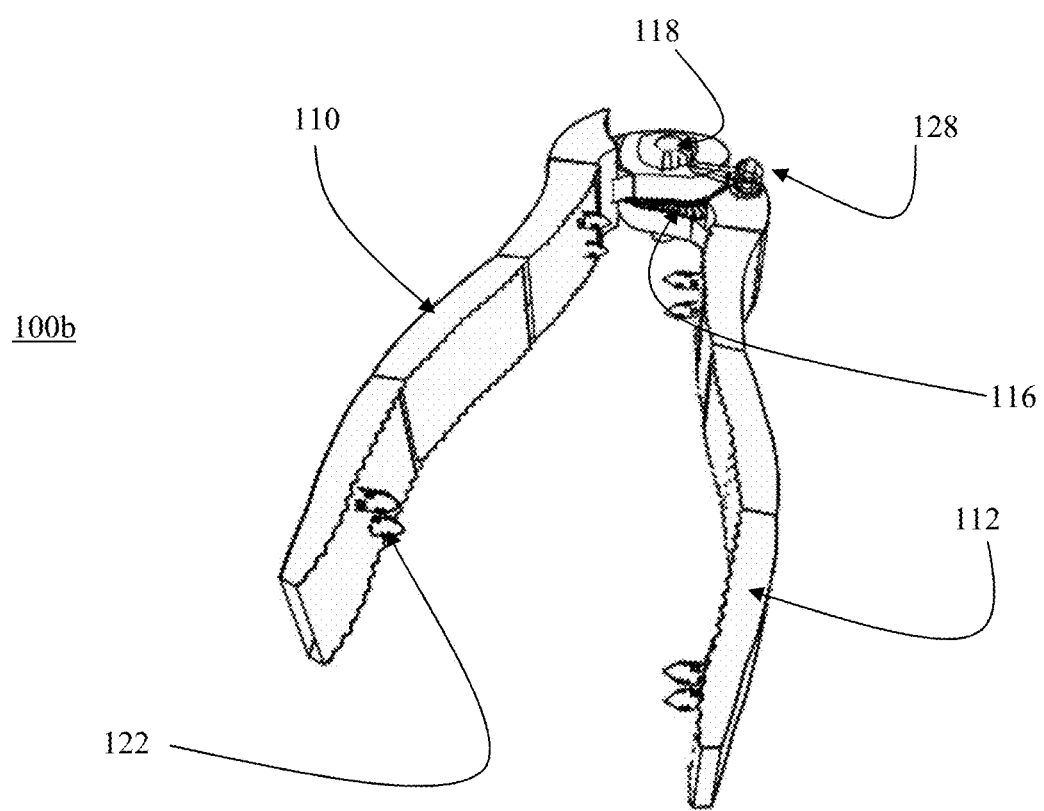
FIG. 3B illustrates a perspective (top oblique) view of the thoracic/lumbosacral TP staple in an open (unclamped) position, according to an exemplary embodiment of the invention.
Figure 3C:
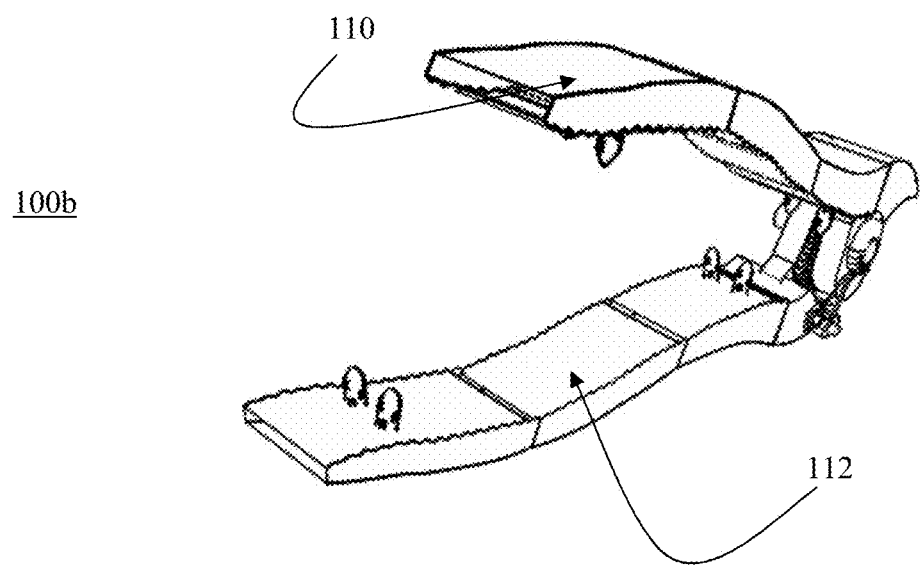
FIG. 3C illustrates a perspective (lateral oblique) view of the thoracic/lumbosacral TP staple in an open (unclamped) position, according to an exemplary embodiment of the invention.
Figure 3D:
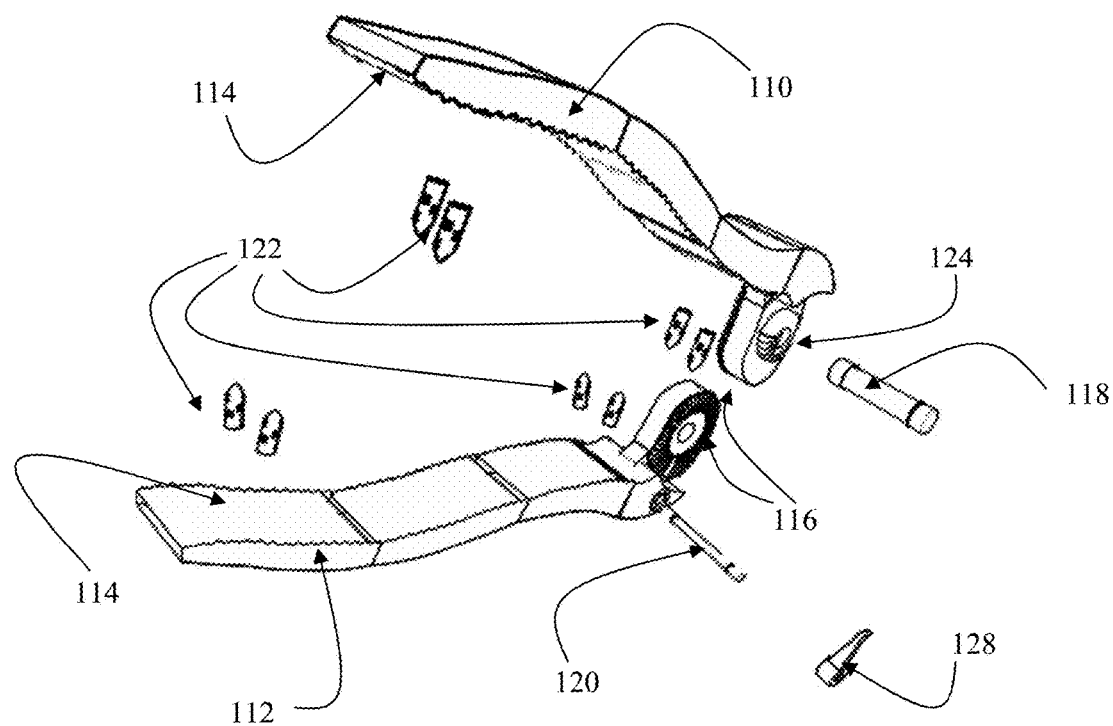
FIG. 3D illustrates an exploded view of the thoracic/lumbosacral TP staple, according to an exemplary embodiment of the invention.
Figure 4A:
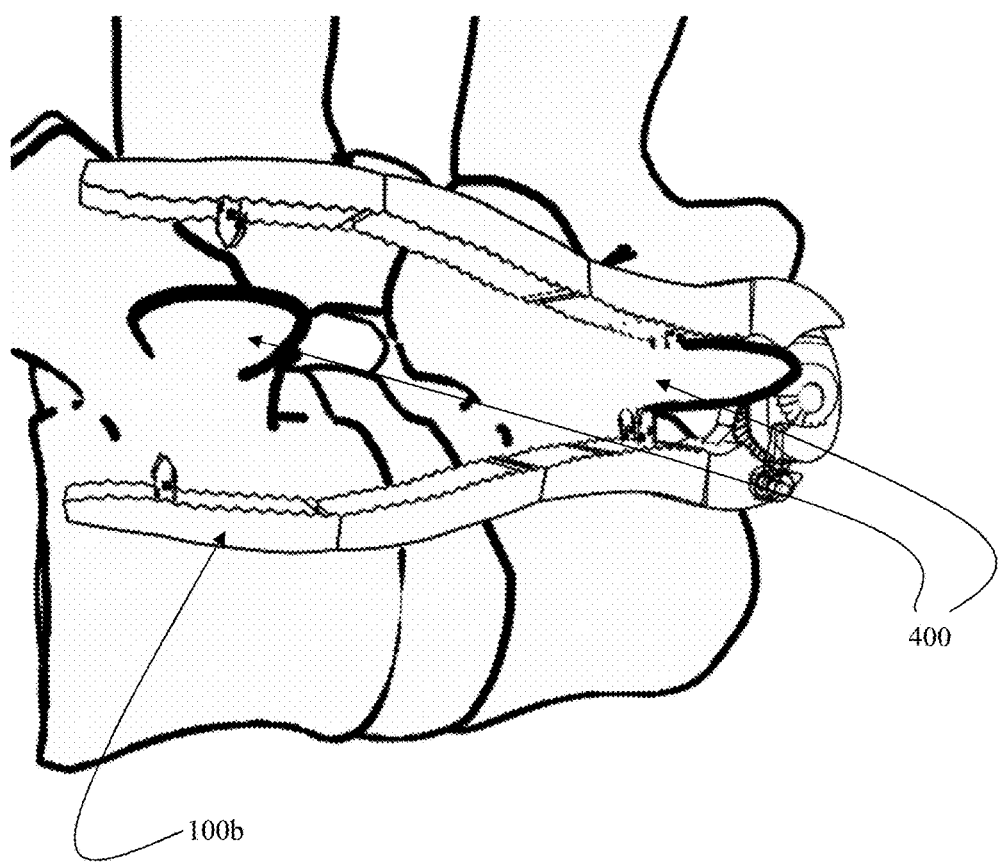
FIG. 4A illustrates a perspective (side oblique) assembly view of the lumbosacral Transverse Process (TP) staple articulating with two TPs in a partially open (partially clamped) position, according to an exemplary embodiment of the invention.
Figure 4B:
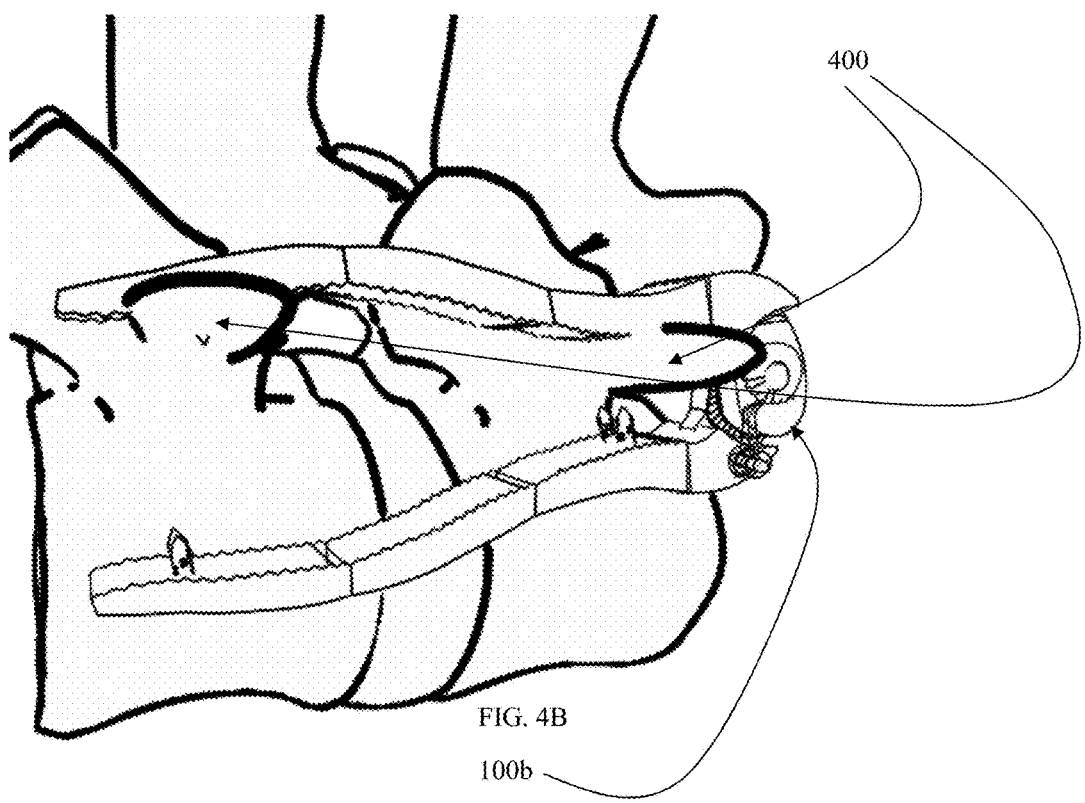
FIG. 4B illustrates a perspective (side oblique) assembly view of the lumbosacral TP staple articulating with two TPs in a partially open (partially clamped) position, according to an exemplary embodiment of the invention.
Figure 4C:
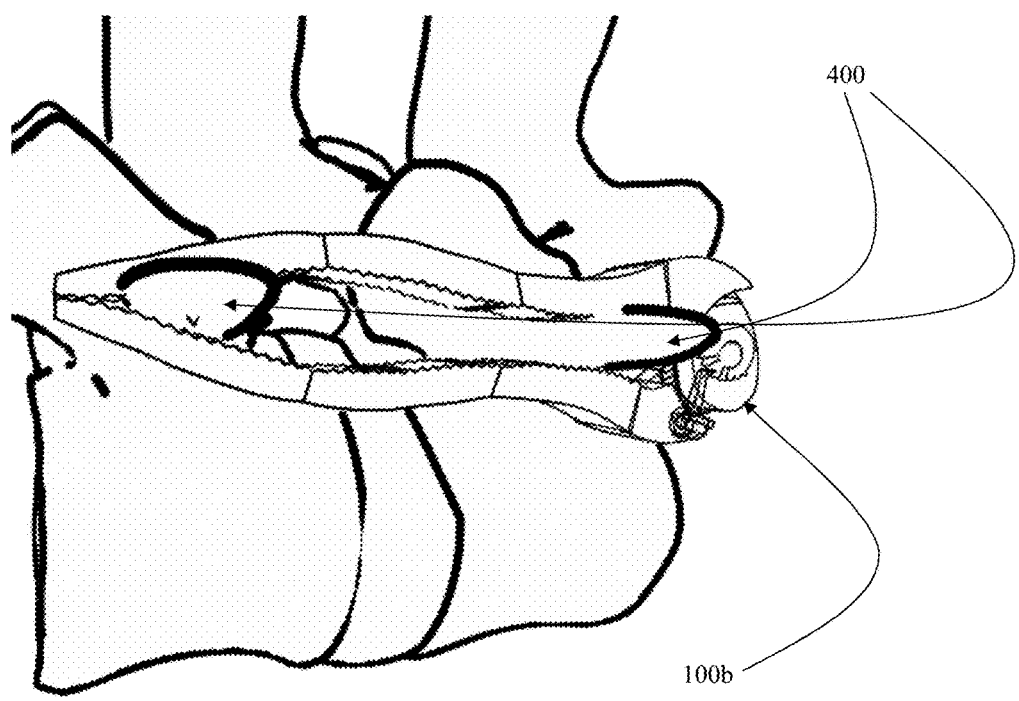
FIG. 4C illustrates a perspective (side oblique) assembly view of the lumbosacral TP staple articulating with two TPs in a closed (clamped) position, according to an exemplary embodiment of the invention.
Figure 4D:
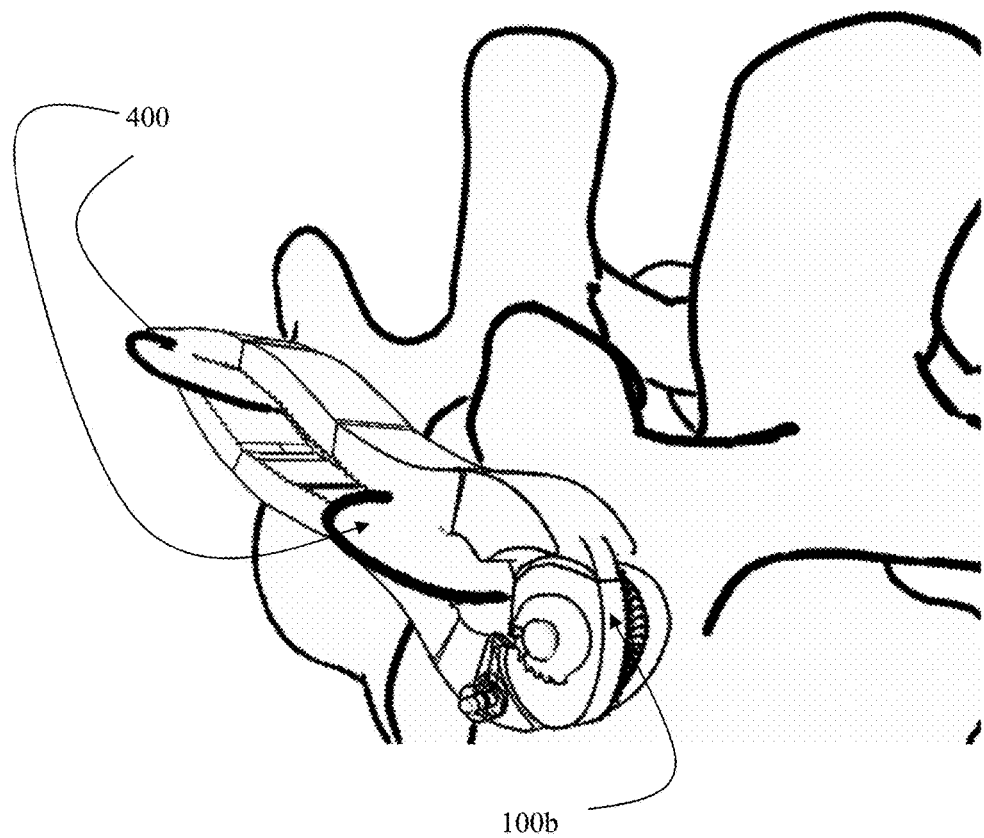
FIG. 4D illustrates a side perspective (posterior oblique) assembly view of the lumbosacral TP staple articulating with two TPs in a closed (clamped) position, according to an exemplary embodiment of the invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Alternate embodiments may be devised without departing from the scope of the invention. Additionally, well known elements of the invention will not be described in detail or will be omitted so as not to obscure the relevant details of the invention. The word "exemplary" is used herein to mean "serving as an example, instance, or illustration." Any embodiment described herein as "exemplary" is not necessarily to be construed as preferred or advantageous over other embodiments. Likewise the term "embodiments of the invention" does not require that all embodiments of the invention include the discussed feature, advantage or mode of operation.

With reference to FIGS. 1A-19C, exemplary embodiments of the invention will now be described.

1. Exemplary Medical Device

Referring to FIGS. 1-9, the above described problems of the conventional art can be solved in the thoracic, lumbar and cervical spines by insertions.

For example, FIGS. 1A-1D illustrate three dimensional views of an embodiment of the thoracic/lumbosacral Spinous Process (SP) staple apparatus 100a.

FIGS. 1A-1D illustrate an exemplary embodiment of a thoracic/lumbosacral SP staple 100a, for example, including a flexure spring (e.g., ratchet pawl 128). As shown in FIGS. 1A-1D, the features of the staple 100a can include top claws 110 and bottom claws 112 with claw ridges 114 to help incorporate and fuse with bone. A staple pin-pivot 118 can connect the top claws 110 and bottom claws 112. The staple 100a may include fastener pins/prongs 122 to help incorporate and fuse with bone; however, the staple 100a is not limited to any number of fastener pins/prongs 122. For example in the illustrated embodiments, the staple 100a includes sixteen fastener pins/prongs 122; eight per the top claw 110 and eight per the bottom claw 112. Further, a total of eight prongs 122 for engagement of two segmental SPs may be utilized such that each SP may be penetrated and perforated by a total of eight prongs 122; four prongs per single SP unit of penetration/engagement on the top claw 110 and four prongs per single SP unit of penetration/engagement on the bottom claw. However, in other embodiments, the staple 100a can include other amounts of fastener pins/prongs 122, such as four, six, eight, ten, etc. for engagement of the segmental SPs.

Claw teeth 116 may be molded onto the top claw 110 and bottom claw 112, and the claw teeth 116 may be interdigitating. Further, ratchet teeth 124 may be molded onto the bottom claw 112 (shown in FIGS. 1A-1B), and a ratchet pawl 128 (e.g., spring loaded ratchet pawl) may interact with the ratchet teeth 124 locking the staple 100a in position. The ratchet pawl 128 can be connected to the top claw 110 via ratchet bolt 120 and can rotate about the ratchet bolt 120 (shown in FIGS. 1A-1B).

In another embodiment, ratchet teeth 124 may also be molded on the top claw 110 (shown in FIGS. 1C-1D), and the ratchet pawl 128 may interact with the ratchet teeth 124 locking the staple 100a in position. The ratchet pawl 128 can be connected to the bottom claw 112 via ratchet bolt 120 and can rotate about the ratchet bolt 120 (shown in FIGS. 1C-1D).

As the staple 100a closes, the ratchet pawl 128 works in standard fashion. When a force is applied to open the staple 100a, the ratchet pawl 128 (e.g., a flexure spring) interacts with the ratchet teeth 124 exhibiting spring-like qualities due to its curvature resulting in the ratchet mechanism "locking up." Thus, the material used for the ratchet pawl 128 can contribute to the deformability and springiness of the ratchet mechanism, resulting in varying degrees of deformability and spring-like resistance. The ratchet mechanism can limit the opening force of the staple 100a by a force proportional to the stiffness of the ratchet pawl 128 (e.g., flexure spring). Further, the force can be tailored by making the ratchet pawl 128 from different materials or varying the dimension(s) of the ratchet pawl 128, or a flexure spring portion of the ratchet pawl 128. This embodiment can achieve significant rigidity (stiffness).

FIGS. 2A-2E illustrate a step-by-step mechanical engagement of an exemplary embodiment of a thoracic/lumbosacral Spinous Process (SP) staple 100a with two segmental SPs; beginning with the staple's fully opened position (FIG. 2A), then subsequently progressing to a semi-closed (partially clamped) position (FIG. 2B), and then subsequently and finally achieving a fully clamped position (FIGS. 2C-2E) entirely engaging and unifying the two segmental SPs.

FIGS. 3A-3D illustrate an exemplary embodiment of a thoracic/lumbosacral Transverse Process (TP) staple 100b.

As shown in FIGS. 3A-3D, the features of the staple 100b can include a top claw 110 and a bottom claw 112, each having claw ridges 114 to help incorporate and fuse with bone. A staple pin-pivot 118 can connect the top claw 110 and the bottom claw 112. The staple 100b may include fastener pins/prongs 122 to help incorporate and fuse with bone; however, the staple 100b is not limited to any number of fastener pins/prongs 122. For example in the illustrated embodiments, the staple 100b includes eight fastener pins/prongs 122; four per the top claw 110 and four per the bottom claw 112. Further, a total of four prongs 122 for engagement of two segmental TPs may be utilized such that each TP may be penetrated and perforated by a total of four prongs; two prongs per single TP unit of penetration/engagement on the top claw 110 and two prongs per single TP unit of penetration/engagement on the bottom claw 112. However, in other embodiments, the staple 100b can include other amounts of fastener pins/prongs 122, such as two, four, six, eight, ten, etc. for engagement of the segmental TPs.

Claw teeth 116 may be molded onto the top claw 110 and bottom claw 112, and the claw teeth 116 may be interdigitating. Further, ratchet teeth 124 may be molded on the top claw 110 (shown in FIGS. 3A-D), and the ratchet pawl 128 may interact with the ratchet teeth 124 locking the staple 100b in position. The ratchet pawl 128 can be connected to the bottom claw 112 via ratchet bolt 120 and can rotate about the ratchet bolt 120 (shown in FIGS. 3A-3D).

In another embodiment, ratchet teeth 124 may also be molded onto the bottom claw 112 (not shown), and a ratchet pawl 128 may interact with the ratchet teeth 124 locking the staple 100b in position. In this embodiment, the ratchet pawl 128 can be connected to the top claw 110 via ratchet bolt 120 and can rotate about the ratchet bolt 120 (not shown).

As the staple 100b closes, the ratchet pawl 128 works in standard fashion. When a force is applied to open the staple 100b, the ratchet pawl 128 (e.g., a flexure spring) interacts with the ratchet teeth 124 exhibiting spring-like qualities due to its curvature resulting in the ratchet mechanism "locking up." Thus, the material used for the ratchet pawl 128 can contribute to the deformability and springiness of the ratchet mechanism, resulting in varying degrees of deformability and spring-like resistance. The ratchet mechanism can limit the opening force of the staple 100b by a force proportional to the stiffness of the ratchet pawl 128 (e.g., flexure spring). Further, the force can be tailored by making the ratchet pawl 128 from different materials or varying the dimension(s) of the ratchet pawl 128, or a flexure spring portion of the ratchet pawl 128. This embodiment can achieve significant rigidity (stiffness).

FIGS. 4A-4D illustrate a step-by-step mechanical engagement of an exemplary embodiment of a thoracic/lumbosacral Transverse Process (TP) staple 100b with two segmental TPs; beginning with the staple's fully opened position (FIG. 4A), then subsequently progressing to a semi-closed position (partially clamped) (FIG. 4B), and then subsequently and finally achieving a fully clamped position (FIGS. 4C-4D) entirely engaging and unifying the two segmental TPs.

Figure 5:
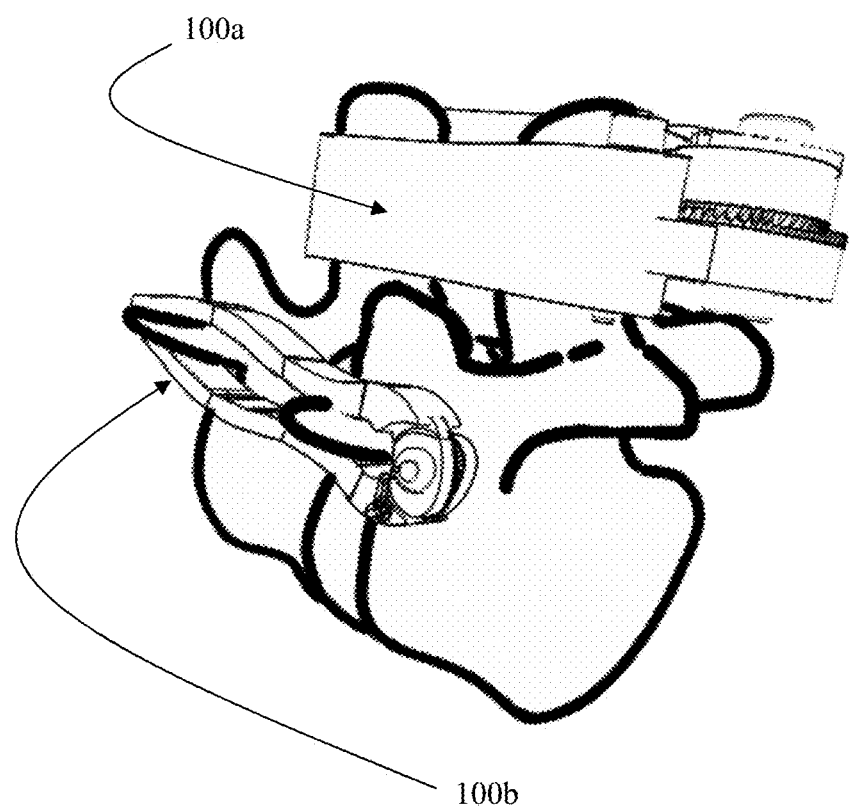
FIG. 5 illustrates a side perspective (posterior-oblique) assembly view of the thoracic/lumbosacral Spinous Process (SP) and Transverse Process (TP) staples engaging (clamped position) SPs and TPs of two adjacent spinal units, according to an exemplary embodiment of the invention.

FIG. 5 illustrates an exemplary embodiment of both a fully clamped thoracic/lumbosacral SP staple 100a and a fully clamped thoracic/lumbosacral TP staple 100b used to concomitantly staple/fuse two segmental spinal units.

Figure 6A:
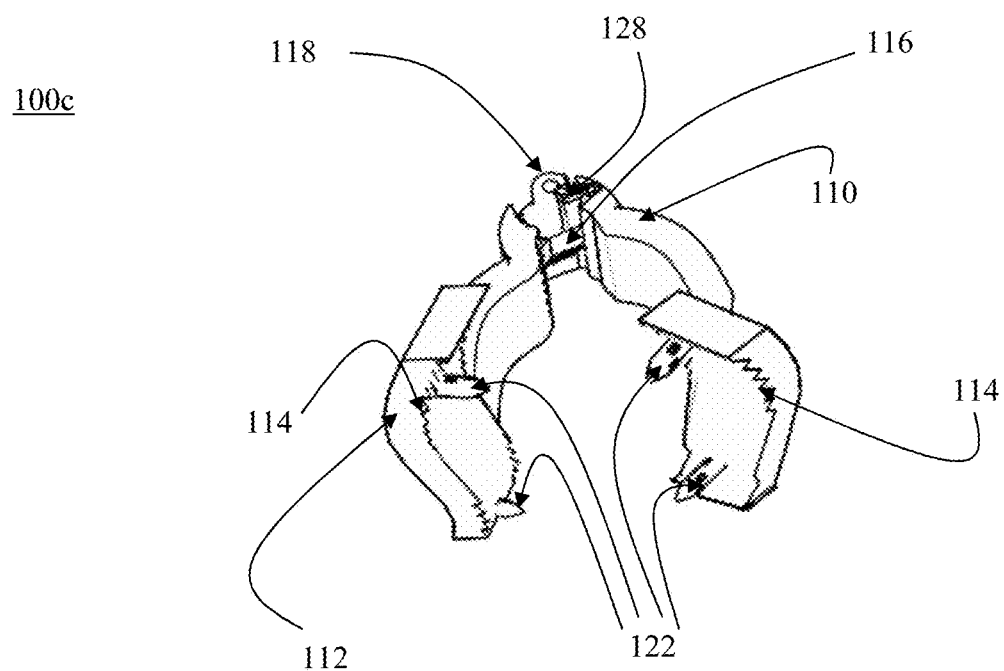
FIG. 6A illustrates a side perspective (top oblique) view of the cervical Spinous Process (SP) staple in a partially open (partially clamped) position, according to an exemplary embodiment of the invention.
Figure 6B:
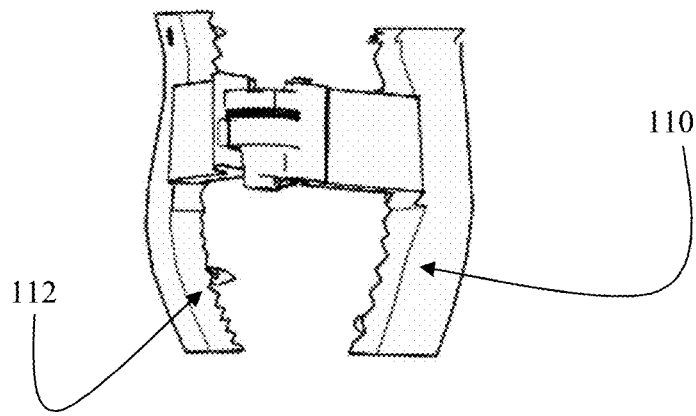
FIG. 6B illustrates a side perspective view of the cervical SP staple in a partially open (partially clamped) position, according to an exemplary embodiment of the invention.
Figure 6C:
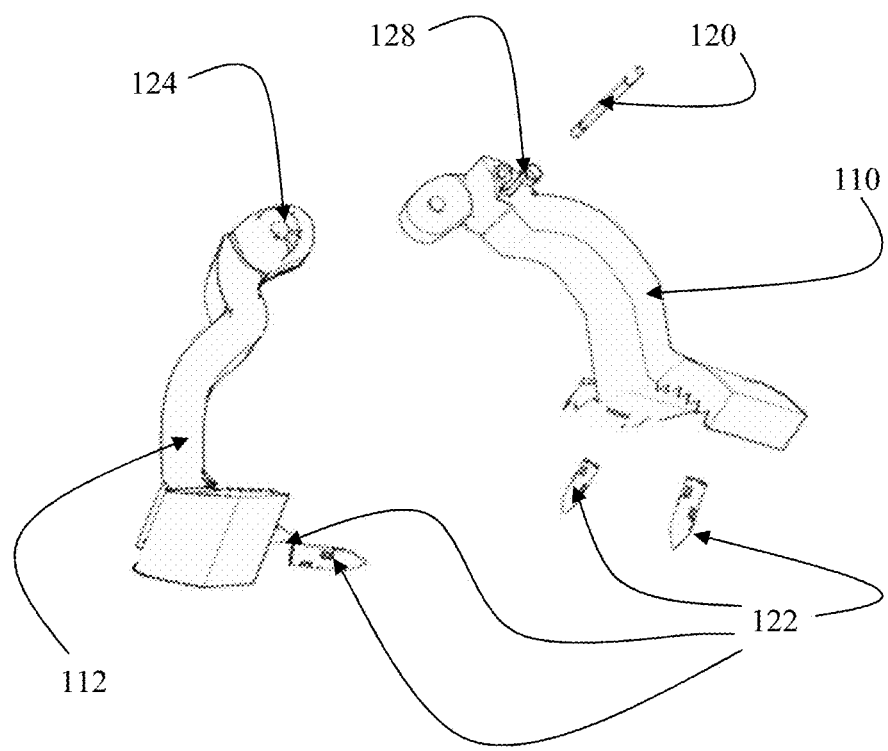
FIG. 6C illustrates an exploded view of the cervical SP staple, according to an exemplary embodiment of the invention.
Figure 7A:
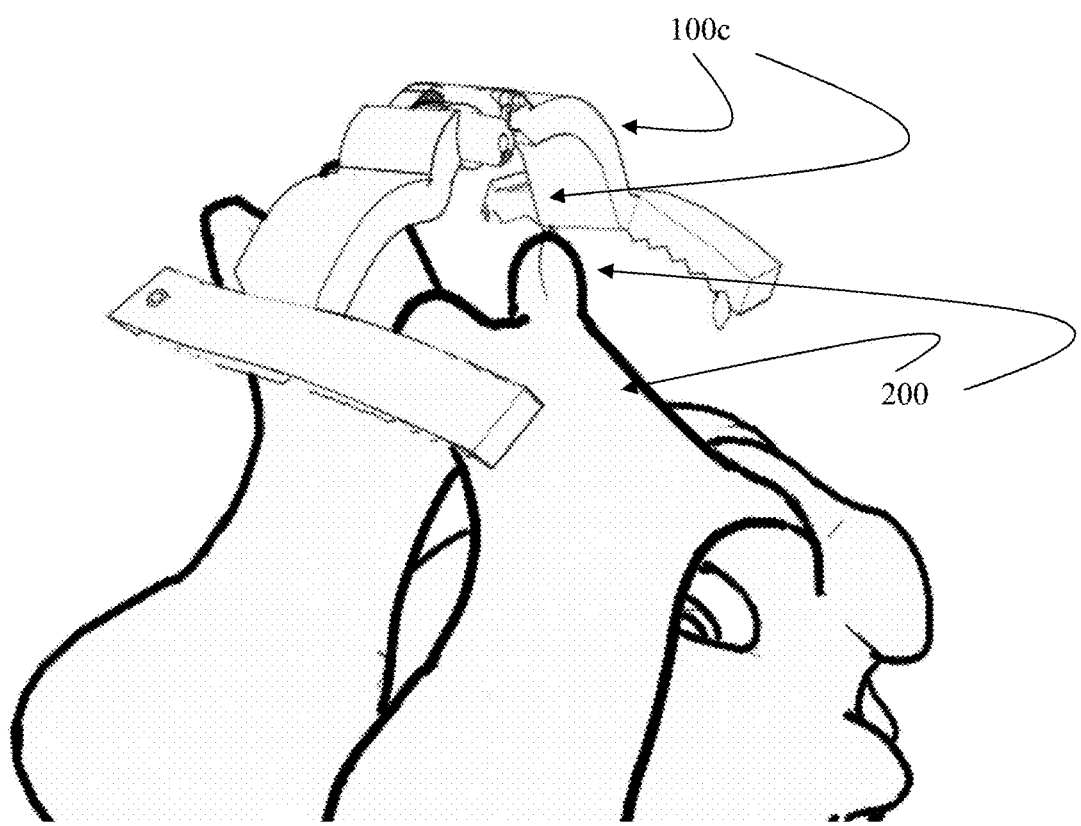
FIG. 7A illustrates a top perspective (side-oblique) assembly view of the cervical SP staple articulating with two SPs in a wide open position, according to an exemplary embodiment of the invention.
Figure 7B:
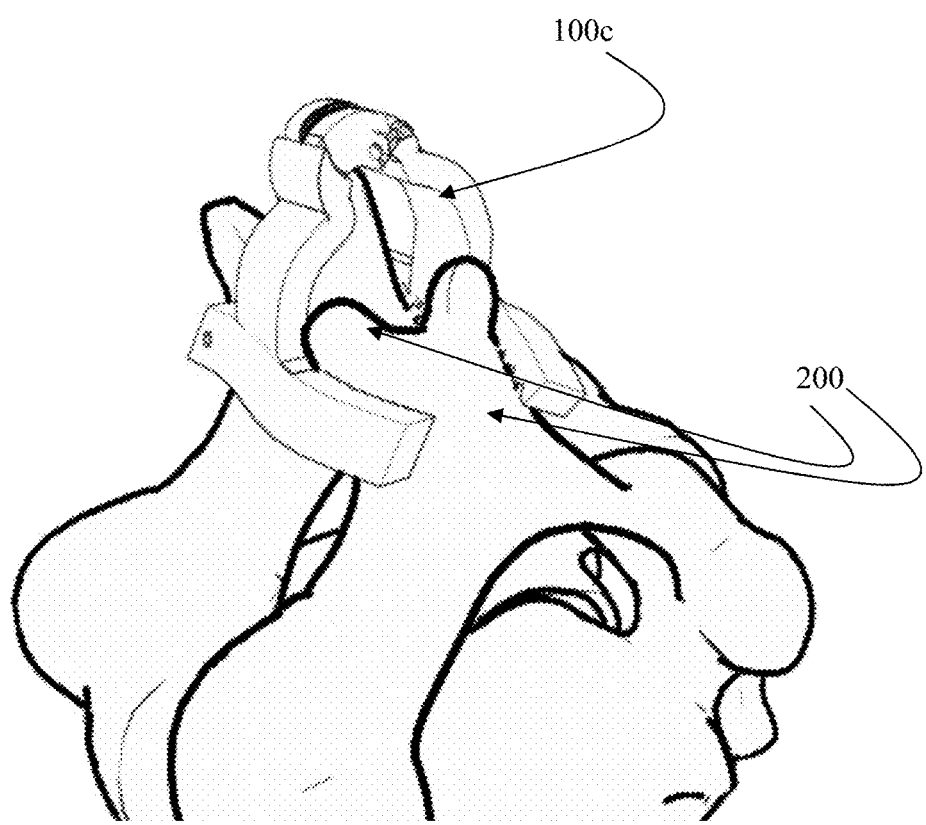
FIG. 7B illustrates a top perspective (top oblique) assembly view of the cervical SP staple articulating with two SPs in a closed (clamped) position, according to an exemplary embodiment of the invention.
Figure 7C:
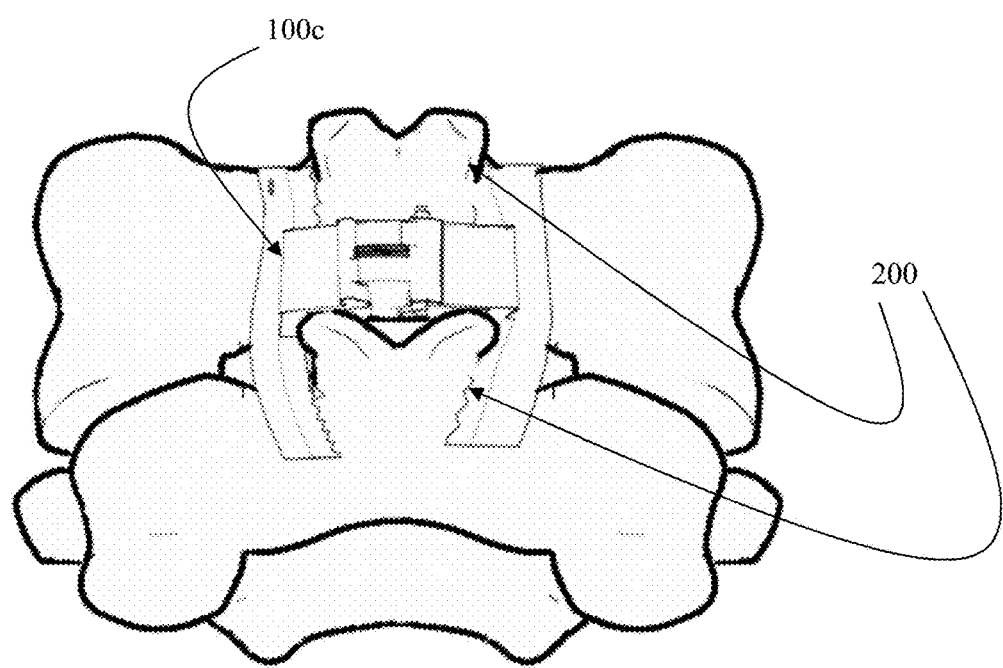
FIG. 7C illustrates a side assembly view of the cervical SP staple articulating with two SPs in a closed (clamped) position, according to an exemplary embodiment of the invention.
Figure 7D:
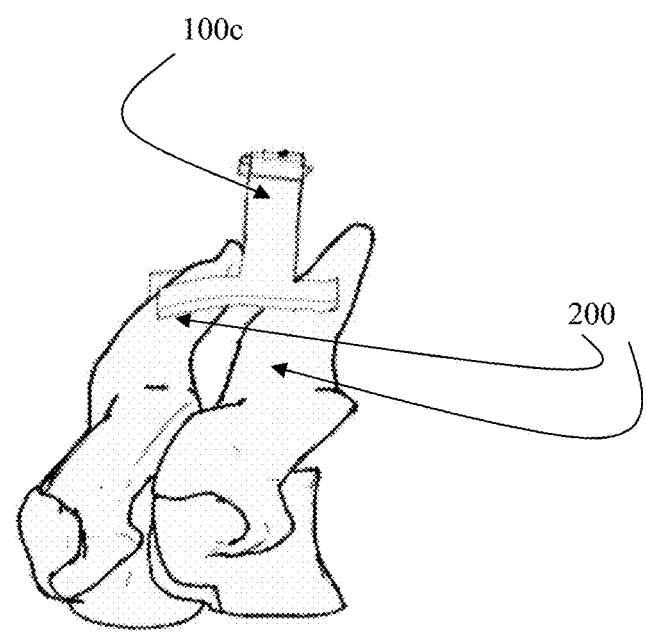
FIG. 7D illustrates a bottom assembly view of the cervical SP staple articulating with two SPs in a closed (clamped) position, according to an exemplary embodiment of the invention.

FIGS. 6A-6C illustrate an exemplary embodiment of a cervical Spinous Process (SP) staple 100c.

As shown in FIGS. 6A-6C, the features of the staple 100c can include a top claw 110 and a bottom claw 112, each having claw ridges 114 to help incorporate and fuse with bone. A staple pin-pivot 118 can connect the top claw 110 and the bottom claw 112. The staple 100c may include fastener pins/prongs 122 to help incorporate and fuse with bone; however, the staple 100c is not limited to any number of fastener pins/prongs 122. For example in the illustrated embodiments, the staple 100c includes four fastener pins/prongs 122; two per the top claw 110 and two per the bottom claw 112. Further, a total of two prongs 122 for engagement of each SP may be utilized such that each SP may be penetrated and perforated by a total of two prongs 122; one prong per single SP unit of penetration/engagement on the top claw 110 and one prong per single SP unit of penetration/engagement on the bottom claw 112. However, in other embodiments, the staple 100c can include other amounts of fastener pins/prongs 122, such as six, eight, ten, etc. for engagement of the cervical SPs.

Claw teeth 116 may be molded onto the top claw 110 and the bottom claw 112, and the claw teeth 116 may be interdigitating. Further, ratchet teeth 124 may be molded onto the bottom claw 112 (shown in FIGS. 6A-6C), and a ratchet pawl 128 may interact with the ratchet teeth 124 locking the staple 100c in position. The ratchet pawl 128 can be connected to the top claw 110 via ratchet bolt 120 and can rotate about the ratchet bolt 120 (shown in FIGS. 6A-6C).

In another embodiment, ratchet teeth 124 may also be molded on the top claw 110 (not shown), and the ratchet pawl 128 may interact with the ratchet teeth 124 locking the staple 100*c* in position. The ratchet pawl 128 can be connected to the bottom claw 112 via ratchet bolt 120 and can rotate about the ratchet bolt 120 (not shown).

As the staple 100*c* closes, the ratchet pawl 128 works in standard fashion. When a force is applied to open the staple 100*c*, the ratchet pawl 128 (e.g., a flexure spring) interacts with the ratchet teeth 124 exhibiting spring-like qualities due to its curvature resulting in the ratchet mechanism "locking up." Thus, the material used for the ratchet pawl 128 can contribute to the deformability and springiness of the ratchet mechanism, resulting in varying degrees of deformability and spring-like resistance. The ratchet mechanism can limit the opening force of the staple 100*c* by a force proportional to the stiffness of the ratchet pawl 128 (e.g., flexure spring). Further, the force can be tailored by making the ratchet pawl 128 from different materials or varying the dimension(s) of the ratchet pawl 128, or a flexure spring portion of the ratchet pawl 128. This embodiment can achieve significant rigidity (stiffness).

FIGS. 7A-7E illustrate a step-by-step mechanical engagement of an exemplary embodiment of the cervical Spinous Process (SP) staple 100*c* with two segmental cervical SPs; beginning with the staple's fully opened position (FIG. 7A), and then subsequently progressing to a fully clamped position (FIGS. 7B-7D) entirely engaging and unifying the two cervical TPs.

FIGS. 8A-8D illustrate exemplary embodiments of a straight fastener solid prong 122*a*, a straight perforated fastener prong 122*b*, a curved fastener solid prong 122*c*, and a curved perforated fastener prong 122*d*.

Figures 9A, 9B:
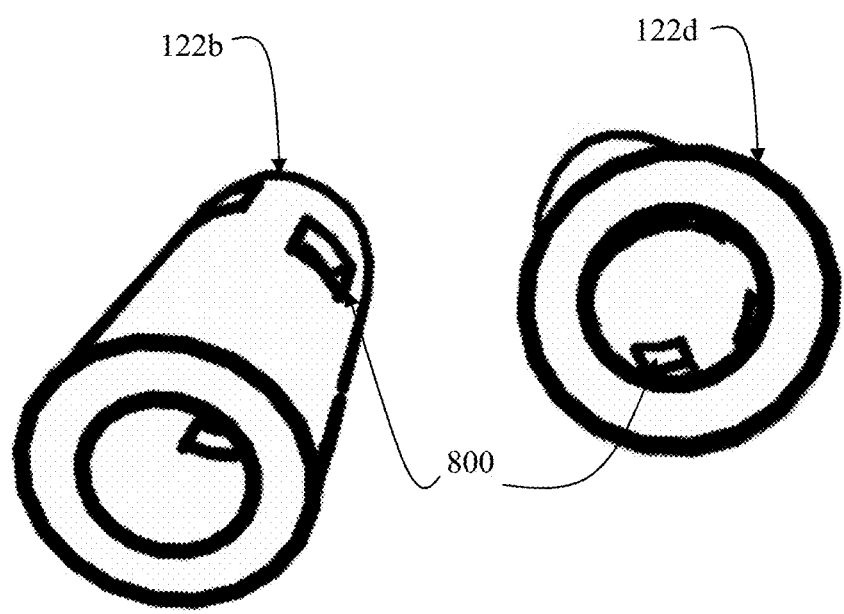
FIG. 9A illustrates a bottom perspective view of the straight-perforated staple prong, according to an exemplary embodiment of the invention.
FIG. 9B illustrates a bottom perspective view of the curved-perforated staple prong, according to an exemplary embodiment of the invention.

FIGS. 9A-9B illustrate a bottom perspective view of a straight-perforated staple prong 122*b* and a bottom perspective view of a curved-perforated staple prong 122*d*. The perforations 800 of these prongs allow insertion of bone and/or fusion material facilitating the fusion of the device to the spinous process thereby facilitating fusion. The perforations 800 can also be applied to other pins, staple screws involved in securing bone to facilitate fusion.

An exemplary embodiment of a thoracic/lumbar Spinous Process (SP) staple, can include first claw means (e.g., 110 or 112), second claw means (e.g., 110 or 112), a staple pin (e.g., 118) pivotally connecting the first claw means and the second claw means (e.g., 110, 112), and ratchet means (e.g., 124, 128) for limiting an opening force of the first claw means (e.g., 110 or 112) with respect to the second claw means (e.g., 110 or 112).

2. Exemplary Surgical Method

Exemplary surgical steps for practicing one or more of the foregoing exemplary embodiments will now be described.

Surgical implantation of the thoracic/lumbosacral Spinous Process (SP) staple (e.g., 100*a*) conjoining two adjacent SPs can be performed under standard open, closed, percutaneous, endoscopic, tubular, microscopic, fluoroscopic or any other standardized techniques. The staple (e.g., 100*a*) is applied to and engages with a staple gun (for example, as described in related application Ser. No. 12/471,345, filed on May 22, 2009, application Ser. No. 12/471,340, filed on May 22, 2009, Ser. No. 12/054,335 filed on Mar. 24, 2008, Ser. No. 11/842,855, filed on Aug. 21, 2007, Ser. No. 11,536,815 filed on Sep. 29, 2006, and Ser. No. 11/208,644 filed on Aug. 23, 2005, which describe a facet joint (FJ) staple and staple gun). The staple gun can have a straight distal applier or angled applier to facilitate placement depending on the particular spinal anatomy. Upon exposure of two adjacent SP processes, the staple (e.g., 100*a*) is opened via the staple gun applier, the two adjacent SPs are engaged by the opened staple claws (e.g., 110, 112), and the staple gun then closes the upper and lower claws (e.g., 110, 112) which lead to the stapling/fusion of the two adjacent spinous processes (FIGS. 2A-2E). Depending on patient anatomy or surgical preference, the staple prongs (e.g., 122) can be either straight or curved. The staple prongs (e.g., 122) with perforations can be packed with any kind of bony/fusion material prior to placement on SPs. A variety of staples (e.g., 100*a*) with varying inter-prong distances to account for inter and intra-patient inter-spinous distance variations can be manufactured. The staple (e.g., 100*a*) with the correct approximate inter-spinous prong distance is selected.

Surgical implantation of the thoracic/lumbosacral Transverse Process (TP) staple (e.g., 100*b*) conjoining two adjacent TPs can be performed under standard open, closed, percutaneous, endoscopic, tubular, microscopic, fluoroscopic or any other standardized techniques. The Transverse Process (TP) staple (e.g., 100*b*) is applied to, and engages a staple gun (for example, as described in related application Ser. No. 12/471,345, filed on May 22, 2009, application Ser. No. 12/471,340, filed on May 22, 2009, Ser. No. 12/054,335 filed on Mar. 24, 2008, Ser. No. 11/842,855, filed on Aug. 21, 2007, Ser. No. 11,536,815 filed on Sep. 29, 2006, and Ser. No. 11/208,644 filed on Aug. 23, 2005, which describe a facet joint (FJ) staple and staple gun). The staple gun can have a straight distal applier or angled applier to facilitate placement depending on the particular spinal anatomy. Upon exposure of the TP processes, the staple (e.g., 100*b*) is opened via the staple gun applier, the TPs are engaged by the opened staple claws (e.g., 110, 112), and the staple gun then closes the upper and lower claws (e.g., 110, 112) which lead to the stapling/fusion of two adjacent transverse processes (FIGS. 4A-4D). Depending on patient anatomy or surgical preference, the staple prongs (e.g., 122) can be either straight or curved. The staple prongs (e.g., 122) with perforations can be packed with any kind of bony/fusion material prior to placement on TPs. A variety of staples (e.g., 100*b*) with varying inter-prong distances to account for inter and intra patient inter TP distance variations can be manufactured. The staple (e.g., 100*b*) with the correct approximate inter TP prong distance is selected.

Surgical implantation of the cervical Spinous Process (SP) staple (e.g., 100*c*) can be performed under standard open, closed, percutaneous, endoscopic, tubular, microscopic, fluoroscopic or any other standardized techniques. The cervical Spinous Process (SP) staple (e.g., 100*c*) is applied to and engages a staple gun (for example, as described in related application Ser. No. 12/471,345, filed on May 22, 2009, application Ser. No. 12/471,340, filed on May 22, 2009, Ser. No. 12/054,335 filed on Mar. 24, 2008, Ser. No. 11/842,855, filed on Aug. 21, 2007, Ser. No. 11,536,815 filed on Sep. 29, 2006, and Ser. No. 11/208,644 filed on Aug. 23, 2005, which describe a facet joint (FJ) staple and staple gun). The staple gun can have a straight distal applier or angled applier to facilitate placement depending on the particular spinal anatomy. Upon exposure of the cervical SP processes, the staple (e.g., 100*c*) is opened via the staple gun applier, the two adjacent cervical SPs are engaged from above by the opened staple claws (e.g., 110, 112), and the staple gun then closes the upper and lower claws (e.g., 110, 112) which lead to the stapling/fusion of cervical spinous processes (FIGS. 7A-7D). Depending on patient anatomy or surgical preference, the staple prongs (e.g., 122) can be either straight or curved. The staple prongs (e.g., 122) with perforations can be packed with any kind of bony/fusion material prior to placement on SPs. A variety of staples (e.g., 100c) with varying inter-prong distances to account for inter and intra patient inter-spinous distance variations can be manufactured. The staple (e.g., 100c) with the correct approximate inter-spinous prong distance is selected.

With reference to FIGS. 10A-12B another exemplary embodiment of the invention will now be described.

3. Exemplary Medical Device

Referring to FIGS. 10A-12B, the above described problems of the conventional art can be solved in the thoracic, lumbar and cervical spine.

Figure 10A:
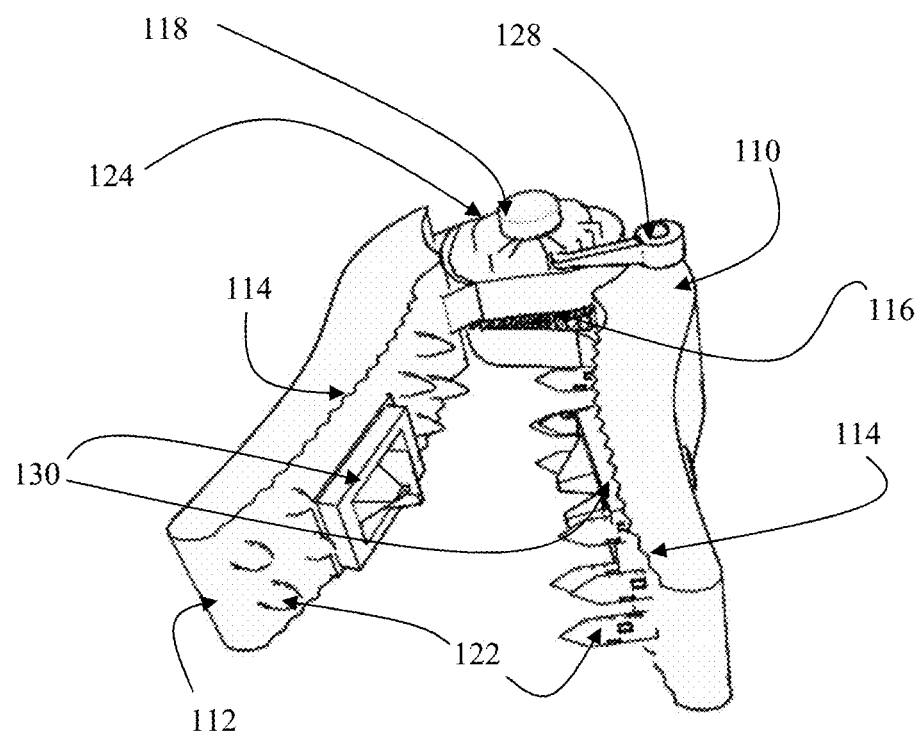
FIG. 10A illustrates a perspective (top oblique) view of the SP staple in an open position, according to an exemplary embodiment of the invention.
Figure 10B:
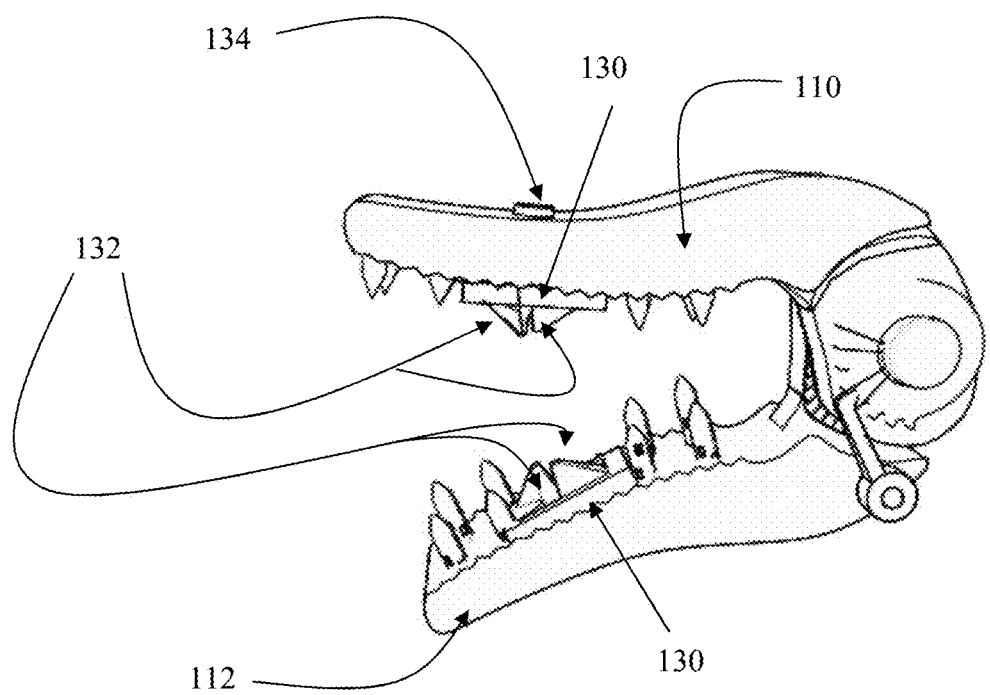
FIG. 10B illustrates a perspective (lateral) view of the SP staple in an open position, according to an exemplary embodiment of the invention.

For example, FIGS. 10A-B illustrate three dimensional views of an embodiment of the Spinous Process (SP) staple apparatus 100a.

FIGS. 10A-B illustrate an embodiment of a Spinous Process (SP) staple with interdigitating-interlocking hemi-spacers, for example, including a flexure spring (e.g., ratchet pawl 128). As shown in FIGS. 10A-B, the features of the staple 100 can include top claws 110 and bottom claws 112 with claw ridges 114 to help incorporate and fuse with bone. A staple pin-pivot 118 can connect the top claws 110 and bottom claws 112. The staple 100 may include fastener pins/prongs 122 to help incorporate and fuse with bone; however, the staple 100 is not limited to any number of fastener pins/prongs 122. For example, in the illustrated embodiments, the staple 100 includes sixteen fastener pins/prongs 122; eight per the top claw 110 and eight per the bottom claw 112. Further, a total of eight prongs for engagement of two segmental SPs may be utilized such that each SP may be penetrated and perforated by a total of eight prongs; four prongs per single SP unit of penetration/engagement on the top claw 110 and four prongs per single SP unit of penetration/engagement on the bottom claw. However, in other embodiments, the staple 100 can include other amounts of fastener pins/prongs 122, such as four, six, eight, ten, etc. for engagement of the segmental SPs.

Claw teeth 116 may be molded onto the top claw 110 and bottom claw 112, and the claw teeth 116 may be interdigitating. Further, ratchet teeth 124 may be molded onto the bottom claw 112 (shown in FIG. 10A), and a ratchet pawl 128 (e.g., spring loaded ratchet pawl) may interact with the ratchet teeth 124 locking the staple 100 in position. The ratchet pawl 128 can be connected to the top claw 110 via ratchet bolt 120 and can rotate about the ratchet bolt 120 (shown in FIG. 10A).

In another embodiment, ratchet teeth 124 may also be molded on the top claw 110 (shown in FIG. 10B), and the ratchet pawl 128 may interact with the ratchet teeth 124 locking the staple 100 in position. The ratchet pawl 128 can be connected to the bottom claw 112 via ratchet bolt 120 and can rotate about the ratchet bolt 120 (shown in FIG. 1B).

As the staple 100 closes, the ratchet pawl 128 works in standard fashion. When a force is applied to open the staple 100, the ratchet pawl 128 (e.g., a flexure spring) interacts with the ratchet teeth 124 exhibiting spring-like qualities due to its curvature resulting in the ratchet mechanism "locking up." Thus, the material used for the ratchet pawl 128 can contribute to the deformability and springiness of the ratchet mechanism, resulting in varying degrees of deformability and spring-like resistance. The ratchet mechanism can limit the opening force of the staple 100 by a force proportional to the stiffness of the ratchet pawl 128 (e.g., flexure spring). Further, the force can be tailored by making the ratchet pawl 128 from different materials or varying the dimension(s) of the ratchet pawl 128. This embodiment can achieve significant rigidity (stiffness).

The interior surfaces and/or exterior surfaces of the top claw 110 and bottom claw 112 can include hemi-spacer(s) 130. As shown in FIGS. 10A-B, the hemi-spacer(s) 130 can be positioned on the interior surfaces of the top claw 110 and bottom claw 112 such that when the staple 100 is closed, the hemi-spacer(s) 130 are positioned on opposing surfaces of each other. Each hemi-spacer 130 can be attached to the top claw 110 and bottom claw 112, for example, with a screw 134 or other suitable fixing device. Further, the shape of the hemi-spacer(s) 130 can vary. For example, in the illustrated embodiments, the staple 100 includes hemi-spacer(s) 130 that are rectangular in shape. However, in other embodiments, the hemi-spacers 130 can include other shapes, such as circular, oval, square, etc. In other embodiments, a thickness of the hemi-spacer 130 on one claw can be greater than a thickness of the hemi-spacer 130 on the other claw. In still other embodiments, the hemi-spacer 130 can be formed on only one of the claws 110, 112.

Further, each hemi-spacer 130 can include interdigitating prongs 132 which can be used to interdigitate, interlock, and unite with corresponding features on another hemi-spacer 130, thereby forming a single interspinous process spacer wedge. The wedge (hemi-spacer pair 130) can occupy and maintain the inter-spinous space in between adjacent Spinous Processes (SPs), thereby alleviating spinal canal compression and any ensuing lumbar stenosis.

Figure 13A:
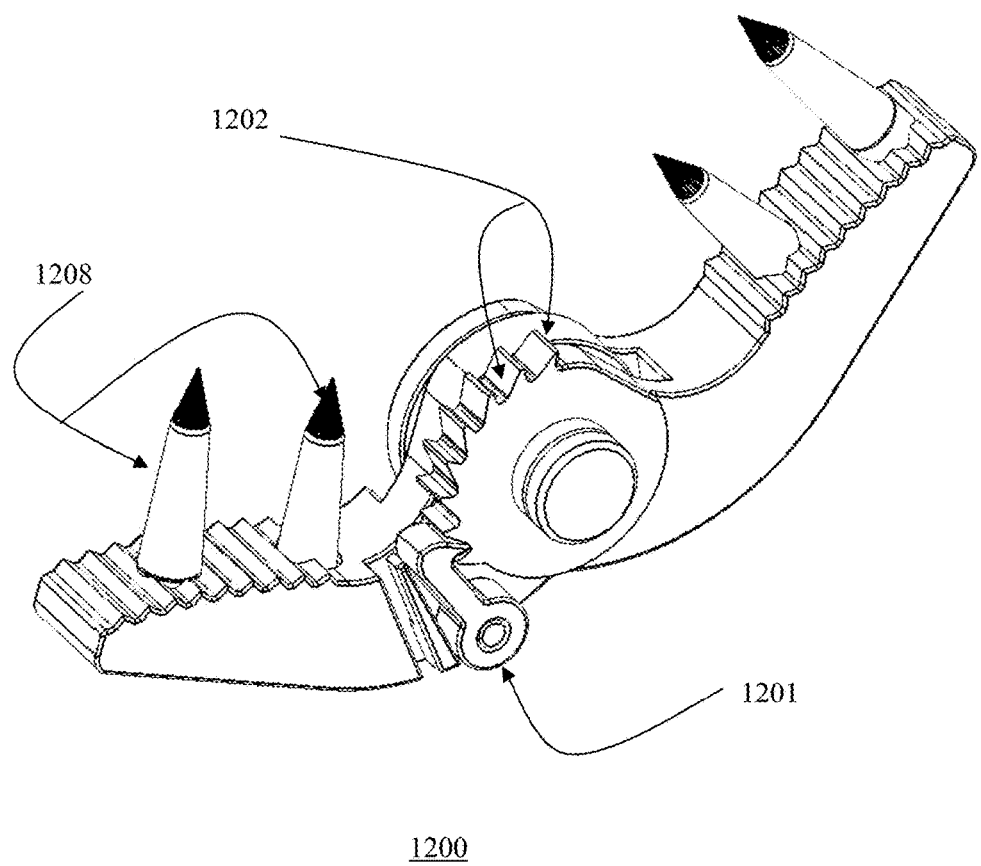
FIGS. 13A-B illustrate a Lumbar facet joint staple with a calibrated ratcheting mechanism in opened (FIG. 13A) and closed (FIG. 13B) positions.
Figure 13B:
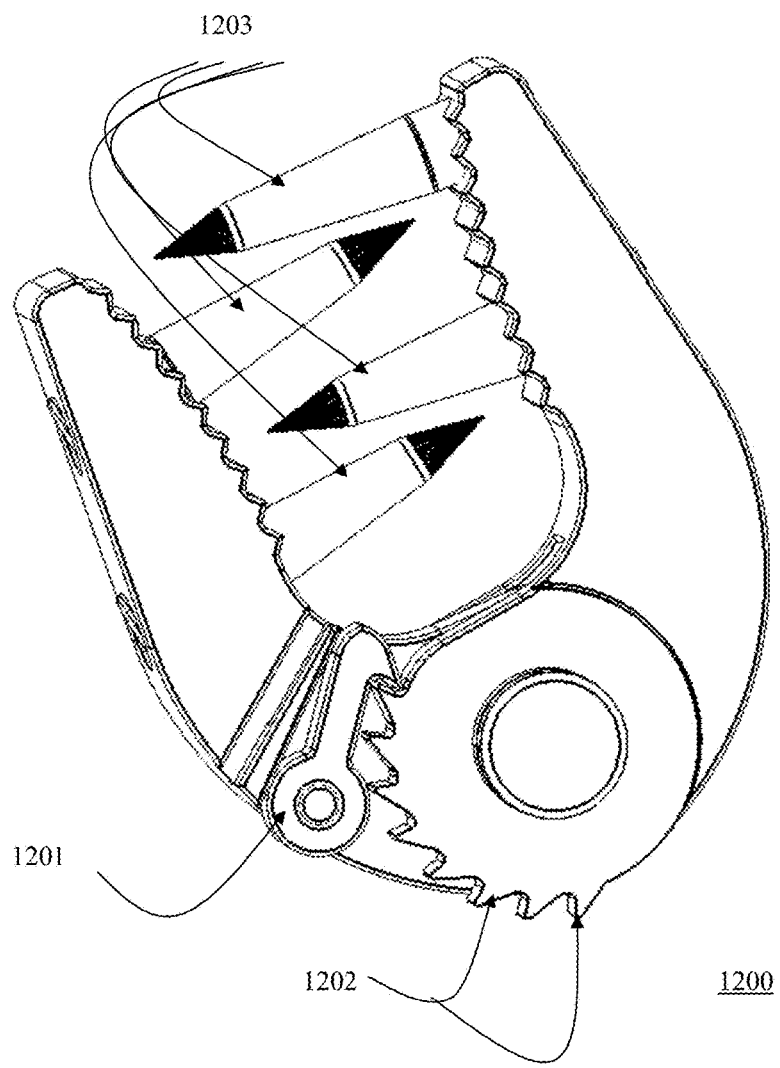

In another exemplary embodiment, each hemi-spacer 130 positioned on opposing staple claws (110, 112) can include interdigitating prongs 132. The interdigitating prongs 132 may include mirror image interlocking protrusions 312 (FIGS. 13A-B) and protrusion receptacles 310 (FIGS. 13A-B). The interlocking protrusions 312 and protrusion receptacles 310 can interact allowing for co-mating and unification of each hemi-spacer 130. Thus, when the top claw 110 and bottom claw 112 of the SP staple 100 are closed (i.e. unit), the fastener prongs 122 will perforate adjacent SPs and the hemi-spacer(s) 130 (and interlocking protrusions 312 and protrusion receptacles 310) will interdigitate, interlock, and unite forming a single interspinous process spacer wedge which maintains separation distraction between SPs, thereby alleviating spinal canal compression thus alleviating lumbar stenosis.

The hemi-spacers 130 can be attached to each claw 110, 112 of the staple 100, for example, via a screw 134 or other suitable fixing device. Further, different sized hemi-spacers 130 can be selectively and preferentially attached to each claw 110, 112 to account for inter- and intra-patient anatomical variability depending on the interspinous distance. The staples 100 also can be manufactured with various tolerances, e.g. different claw lengths and inter-spinous inter-prong distances, etc. The exemplary embodiments disclosed herein can be used to perform multiple levels of distraction engaging a series of adjacent pair of SPs with one staple 100 per every incremental unit of two adjacent SP elements.

Figure 11A:
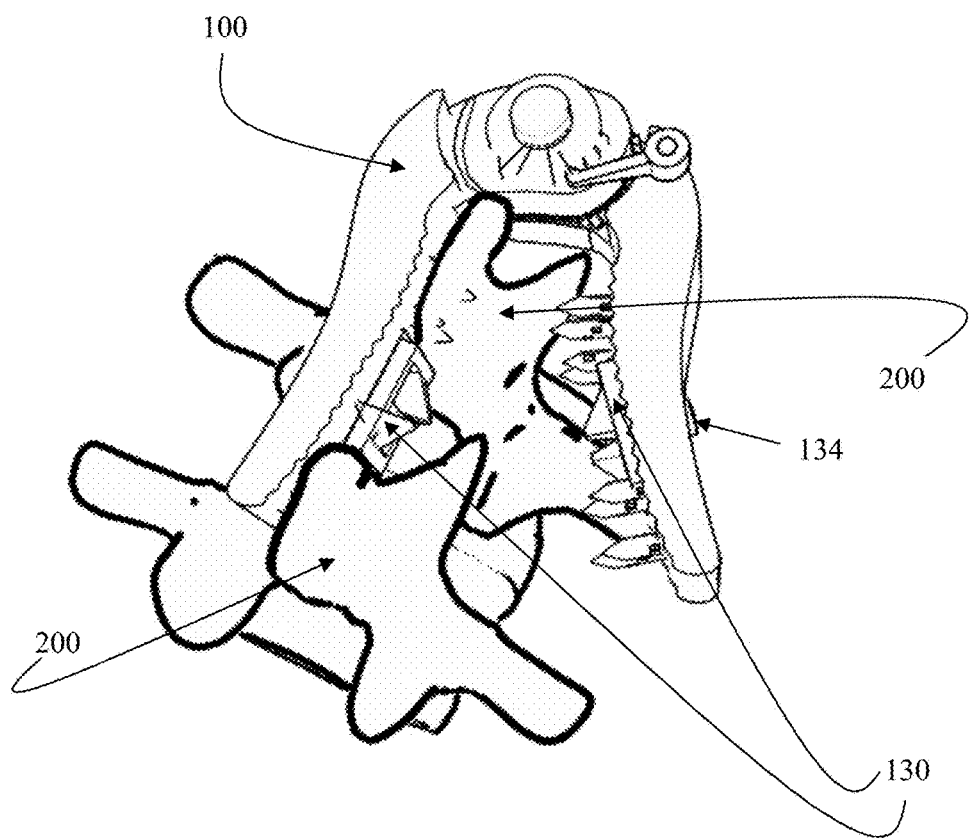
FIG. 11A illustrates a perspective assembly (top oblique) view of the SP staple articulating with two SPs in an open position (wide open), according to an exemplary embodiment of the invention.
Figure 11B:
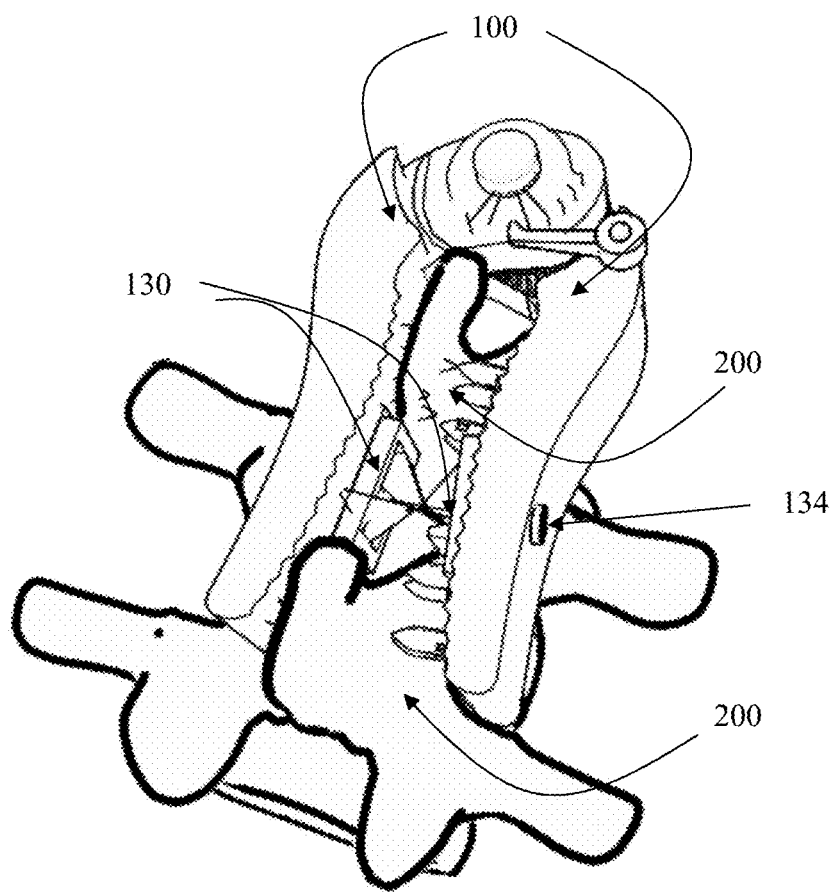
FIG. 11B illustrates a perspective assembly (top oblique) view of the SP staple articulating with two SPs in a partially open position (partially clamped), according to an exemplary embodiment of the invention.
Figure 11C:
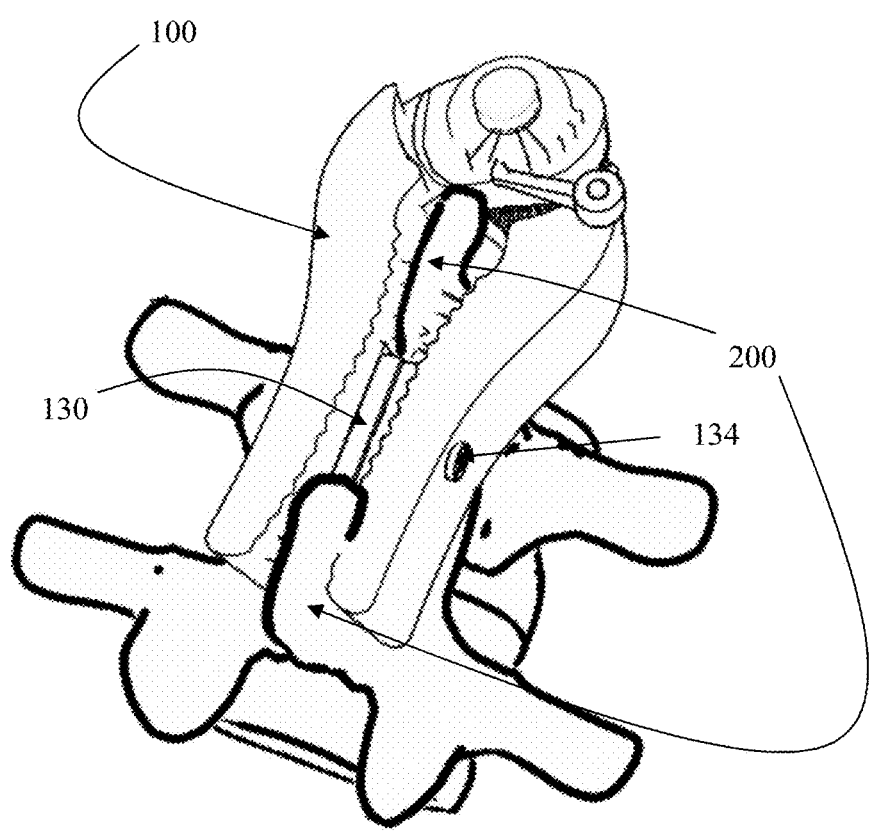
FIG. 11C illustrates a perspective assembly (top oblique) view of the SP staple articulating with two SPs in a closed position, according to an exemplary embodiment of the invention.

FIGS. 11A-C illustrate an exemplary embodiment of a step-by-step mechanical engagement of the SP staple 100 with two segmental SPs; beginning with the staple's opened position (FIG. 11A), then subsequently progressing to a semi-closed position (FIG. 11B), and then subsequently and finally achieving a fully clamped position (FIG. 11C) entirely engaging and unifying the two segmental SPs. The hemi-spacer(s) 130 may include mirror image interlocking protrusions 312 (FIGS. 13A-B) and protrusion receptacles 310 (FIGS. 13A-B). The interlocking protrusions 312 and protrusion receptacles 310 can interact allowing for co-mating and unification of each hemi-spacer 130. Thus, when the top claw 110 and bottom claw 112 of the SP staple 100 are closed (i.e., clamped), the fastener prongs 122 will perforate adjacent SPs and the hemi-spacer(s) 130 (and interlocking protrusions 312 and protrusion receptacles 310) will interdigitate, interlock, and unite forming a single interspinous process spacer wedge which maintains separation distraction between SPs, thereby alleviating spinal canal compression thus alleviating lumbar stenosis.

Figure 12A:
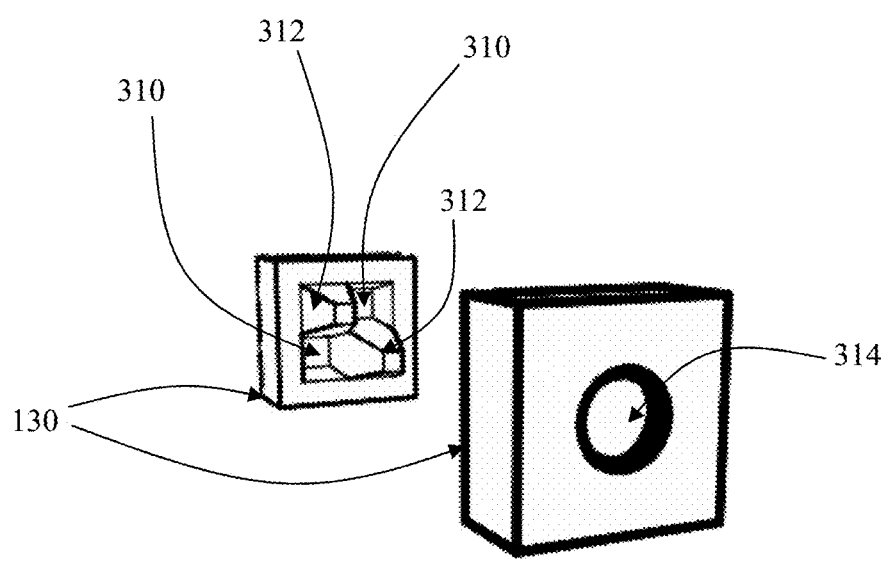
FIG. 12A illustrates a perspective view of two opposing hemi-spacers, according to an exemplary embodiment of the invention.

FIG. 12A illustrates an exemplary embodiment of the hemi-spacer(s) 130 located on opposing staple claws 110, 112. Each hemi-spacer(s) 130 can include one or more hemi-spacer screw inserts 314. Each hemi-spacer(s) 130 can be attached to the top claw 110 and bottom claw 112, for example via one or more screws 134, which can be secured in the one or more hemi-spacer screw inserts 314 and can penetrate one or more perforations (not illustrated) on each claw 110, 112. In the illustrated exemplary embodiment, each hemi-spacer 130 includes a single hemi-spacer screw insert 314, and each hemi-spacer 130 is attached to the top claw 110 and bottom claw 112, respectively, using a single screw 134, which is secured in the hemi-spacer screw insert 314 and penetrates a single perforation (e.g., screw hole or threaded screw hole) (not illustrated) on each claw 110, 112. In other embodiments, the hemi-spacers 130 can be integrally formed with the claws 110, 112. In other embodiments, the hemi-spacers 130 can be permanently or removably/replaceably fixed to the claws 110, 112 by other suitable fixing means.

As shown in FIG. 12A, in an exemplary embodiment, a surface of each hemi-spacer 130 can include two mirror image interdigitating protrusions 312 and two mirror image protrusion receptacles 310 which mate with corresponding features on an opposing hemi-spacer 130 when the hemi-spacers 130 are aligned. However, in other embodiments, the hemi-spacer(s) 130 can include any number of mirror image interdigitating protrusions 312 and corresponding mirror image protrusion receptacles 310 which mate with each other when aligned.

Figure 12B:
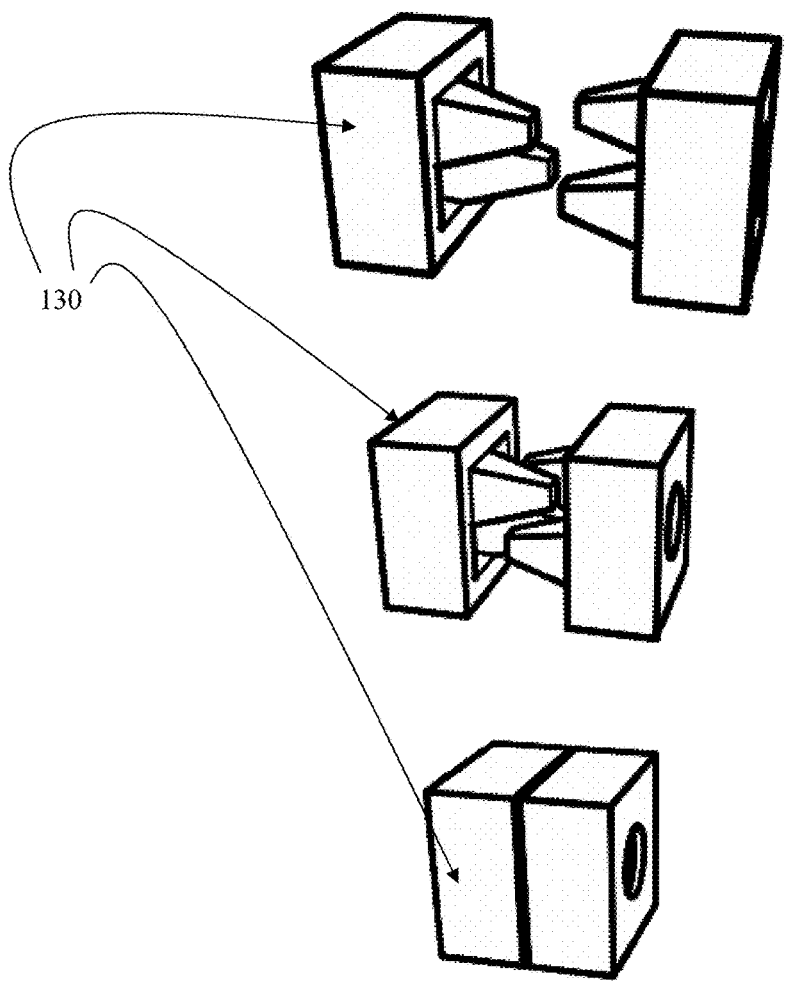
FIG. 12B illustrates a perspective view of sequential interdigitation of opposing hemi-spacers forming a united single interspinous spacer wedge, according to an exemplary embodiment of the invention.

FIG. 12B illustrates an exemplary embodiment of the hemi-spacer(s) 130 whereby two opposing hemi-spacer(s) 130 can unify into a single inter-spinous wedge spacer. For example, in the illustrated embodiments, the mirror image interdigitating protrusions 312 of each opposing hemi-spacer 130 interdigitates and mates with an opposing mirror image protrusion receptacle 310 of the corresponding hemi-spacer 130. The interdigitating protrusions 312 and their corresponding protrusion receptacles 310 of each hemi-spacer 130 can mate with each other forming a unified interspinous spacer-wedge.

The exemplary staples 100 can be provided with a variety of inter-prong distances to account for inter and intra-patient inter-spinous distance variations. The hemi-spacers 130 can be formed with different dimensions, such as a variety of heights, lengths, and widths, to account for variations in dimensions between patients.

The protrusions 312 and protrusion receptacles 310 of the hemi-spacer 130 can have a variety of corresponding shapes. For example, as illustrated in the exemplary embodiments, the sidewalls of the protrusions 312 and protrusion receptacles 310 can have a tapered shape to facilitate easy alignment and engagement/mating therebetween. In other embodiments, the sidewalls of the protrusions 312 and protrusion receptacles 310 can have other shapes, such as conical shapes, pyramid shapes, triangular shapes, square shapes, rectangular shapes, etc.

4. Exemplary Surgical Method

Exemplary surgical steps for practicing one or more of the foregoing embodiments will now be described.

Surgical implantation of the Spinous Process (SP) staple with interdigitating—interlocking hemi-spacers conjoining and separating/distracting two adjacent SPs can be performed under standard open, closed, percutaneous, endoscopic, tubular, microscopic, fluoroscopic or any other standardized techniques. The SP staple can be applied to and engaged with a staple gun whose design has been described in, for example, Applicants' related pending application Ser. No. 12/471,345, filed on May 22, 2009, application Ser. No. 12/471,340, filed on May 22, 2009, Ser. No. 12/054,335 filed on Mar. 24, 2008, Ser. No. 11/842,855, filed on Aug. 21, 2007, Ser. No. 11/536,815 filed on Sep. 29, 2006, and Ser. No. 11/208,644 filed on Aug. 23, 2005, relating to the FJ staple, herein incorporated by reference. The staple gun can have a straight distal applier or angled applier to facilitate placement depending on the particular spinal anatomy. The patient may be positioned prone and flexed or lateral and flexed. After the administration of local anesthesia with or without Intravenous (IV) sedation or any acceptable form of analgesia/anesthesia, an incision is made over the desired adjacent SPs. The interspinous ligament may be partially or completely opened or separated. Upon exposure of two adjacent SP processes, the staple 100 is opened via the staple gun applier, the two adjacent SPs are engaged by the opened staple claws 110, 112, and the staple gun then closes the upper and lower claws 110, 112 which lead to the stapling of the two adjacent SPs (FIGS. 11A-C). The closure of the staple 100 leads to the unification of the two hemi-spacers 130 into one spacer wedge which separates and distracts the adjacent SPs (FIGS. 11A-C and FIG. 13A-B). A variety of staples 100 can be manufactured with varying inter-prong distances to account for inter and intra-patient inter-spinous distance variations. The staple 100 with the correct approximate inter-spinous prong distance is selected. The hemi-spacers 130 with the desired height, length, and width are selected and may be attached to the staple claws 110, 112 prior to SP stapling. Staples 100 can also be manufactured with different sized hemi-spacers 130 already secured to the claws 110, 112, thereby not necessitating that the surgeon need to fiddle with placement of the hemi-spacers 130 on the staple 100, for example, by attaching with screws 134 (i.e., the hemi-spacers 130 can be pre-installed on the claws 110, 112 of the staple 100). Alternatively, in other embodiments staples 100 with built-in (not screwed in) hemi-spacers 130 of differing dimensions can be selected for different patients.

In between the two sets of prongs 122 on the upper and lower claws 110, 112 is an attached rectangular hemi-spacer 130. It is positioned to act as a wedge occupying the inter-spinous space in between adjacent SPs. The hemi-spacers 130 on opposing staple claws 110, 112 are designed with mirror image interlocking protrusions 312, and protrusion receptacles 310 allowing their co-mating and thus unification (FIGS. 13A-B). Thus when the upper and lower claws 110, 112 of the SP staple 100 unite, and their prongs 122 perforate adjacent SPs, the hemi-spacers 130 interdigitate, interlock, and unite forming a single interspinous process spacer wedge which maintains distraction between SPs, thereby alleviating spinal canal compression thus alleviating lumbar stenosis (FIGS. 11A-C).

The hemi-spacers are attached to each claw of the staple via a screw. Depending on the interspinous distance, different sized hemi-spacers (differing in length, height and/or width) can be preferentially attached to each claw to account for inter- and intra-patient anatomical variability.

Furthermore the staples themselves can be manufactured with different claw lengths and inter-spinous inter-prong distances. Hemi-spacers can be designed in any variety of geometric shape, and mate with any form of interlocking mechanisms entailing extrusions slots, prongs, pins etc.

The exemplary embodiment of this device can be used to perform multiple levels of distraction engaging a series of adjacent pair of SPs with one staple per every incremental unit of two adjacent SP elements.

A surgeon can select the degree of adjacent SP separation and distraction by choosing hemi-spacers of increasing lengths.

In another embodiment, an interarticulating staple 100 can be provided for clamping one of a thoracic/lumbar Spinous Process (SP), a thoracic/lumbar Transverse Process (TP), and cervical Spinous Process (SP). The interarticulating staple 100 can include a top claw 110, a bottom claw 112, a staple pin 118 pivotally connecting the top claw 110 and the bottom claw 112, and ratchet means (e.g., 124, 128) for limiting an opening force of the top claw 110 with respect to the bottom claw 112. The staple 100 can include spacer means (e.g., 130) on the top claw 110 and/or on the bottom claw 112 for providing adjacent spinous process separation and/or distraction. Upon the stapling of two adjacent spinous processes, the staple claws approximate, and the spacer means can be wedged between two adjacent spinous processes, thereby providing adjacent spinous process separation and/or distraction leading to spinal canal decompression and alleviation of the symptoms of spinal stenosis.

In another embodiment, an interarticulating staple 100 can be provided for clamping one of a thoracic/lumbar Spinous Process (SP), a thoracic/lumbar Transverse Process (TP), and cervical Spinous Process (SP). The interarticulating staple 100 can include first claw means (e.g., 110) pivotally connected to second claw means (e.g., 112); and ratchet means (e.g., 124, 128) for limiting an opening force of the first claw means (e.g., 110) with respect to the second claw means (e.g., 112) and fixing a position of the first claw means (e.g., 110) with respect the second claw means (e.g., 112); and spacer means (e.g., 130) on at least one of the first claw means (e.g., 110) and the second claw means (e.g., 112), the spacer means for providing one of adjacent spinous process separation and distraction. Upon the stapling of two adjacent spinous processes, the staple claws approximate, and the spacer means can be wedged between two adjacent spinous processes, thereby providing adjacent spinous process separation and/or distraction leading to spinal canal decompression and alleviation of the symptoms of spinal stenosis.

FIGS. 13A-B illustrate a lumbar facet joint staple 1200 in open and closed positions and having staple prongs 1203. This lumbar facet staple has been thoroughly described in Applicants' previous co-pending patent applications, Ser. No. 11/536,815, filed on Sep. 29, 2006, and Ser. No. 11/208,644, filed on Aug. 23, 2005, the relevant portion of each of which is hereby incorporated by reference hereinafter. The new improvement of this device includes a ratchet 1201. The staple 1200 can be incrementally closed with increased ratcheting over increasing number of spurs 1202. This achieves increasing calibrated levels of lumbar facet joint fusion, and conversely diminishing joint flexibility. This new designs further enhances the capacity to achieve flexible fusions in the lumbar spine.

5. Exemplary Medical Device

Figure 14A:
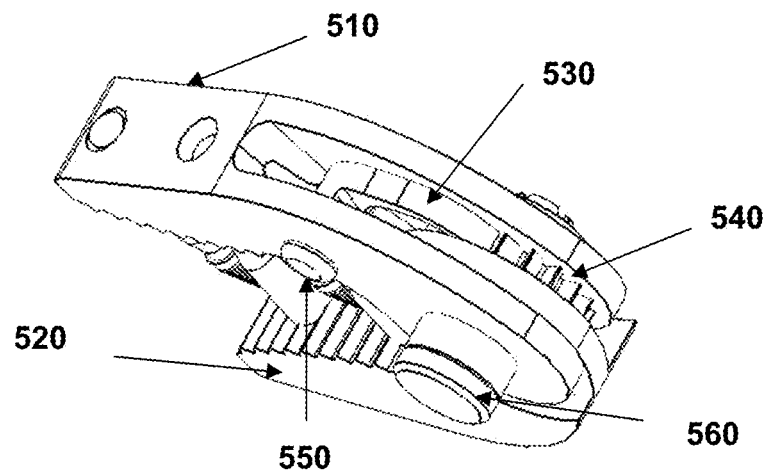
FIGS. 14A-B illustrate an embodiment of a posterior lumbar facet staple, flexure spring embodiment in side isometric (FIG. 14A) and exploded (FIG. 14B) views.
Figure 14B:
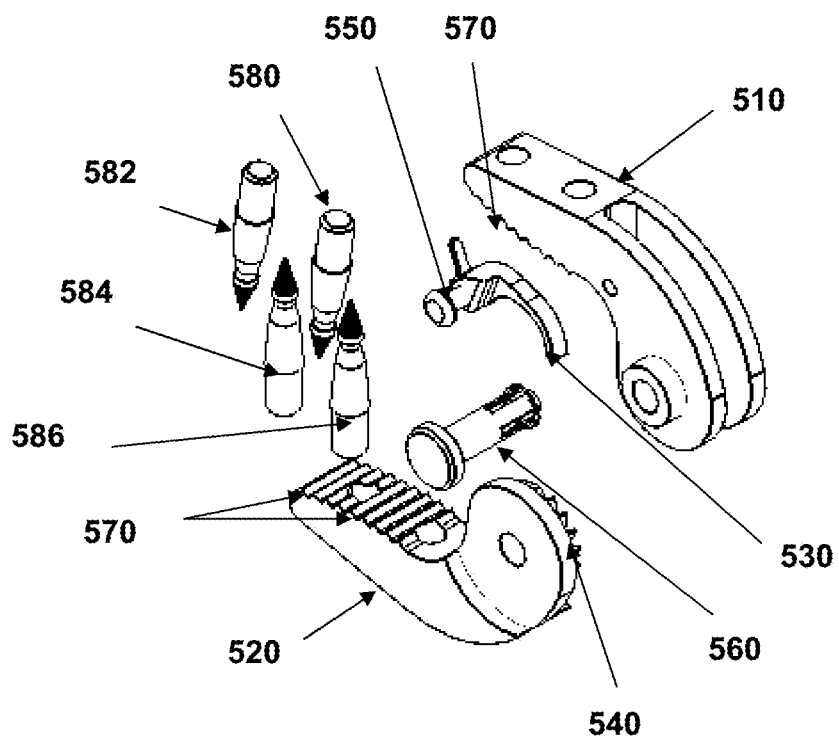
Figure 15A:
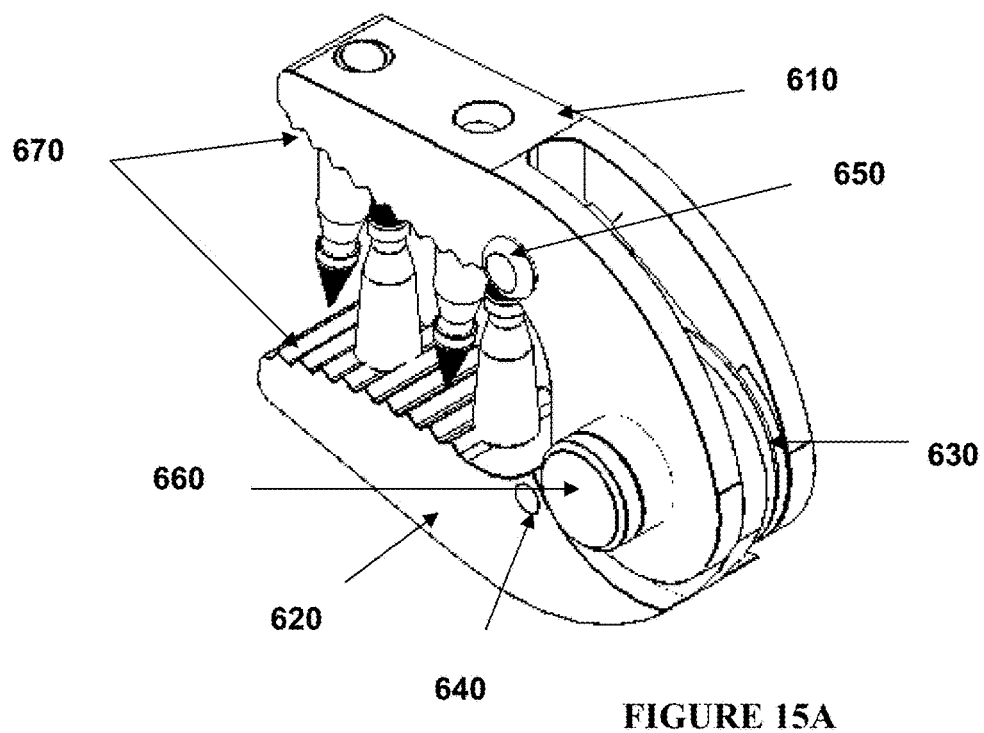
FIGS. 15A-C illustrate an embodiment of a posterior lumbar facet staple, torsional spring embodiment in side isometric (FIG. 15A), bottom isometric (FIG. 15B), and exploded (FIG. 15C) views.
Figure 15B:
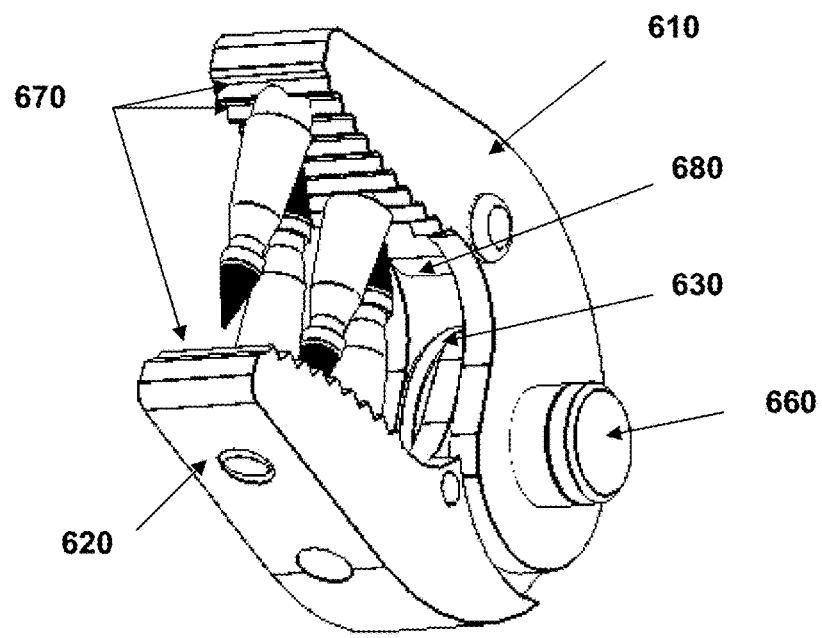
Figure 15C:
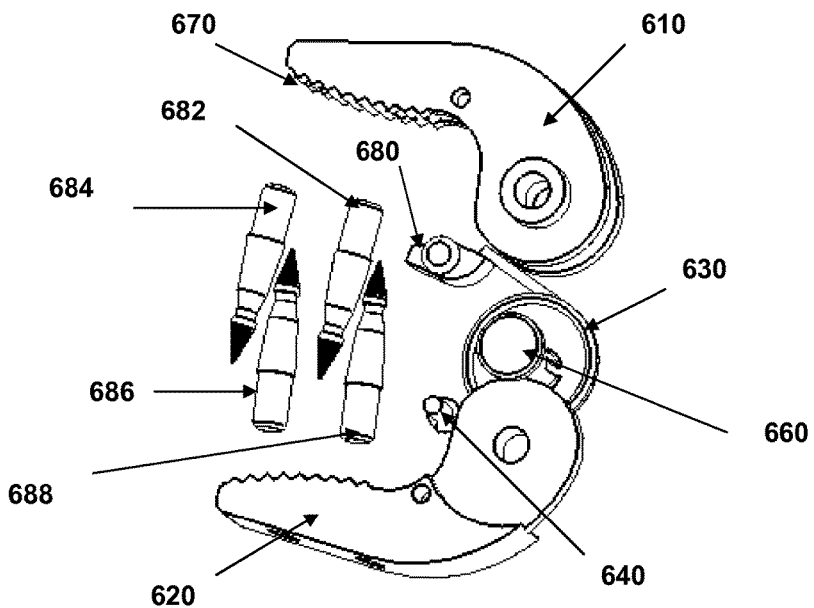

FIGS. 14A-B illustrate an embodiment of a posterior lumbar facet staple having a flexure spring. FIGS. 15A-C illustrate an embodiment of a lumbar facet staple having a torsional spring. Features of a lumbar facet staple have been thoroughly described in the aforementioned related applications, the relevant portions of which are hereby incorporated by reference herein in their entirety. The embodiments illustrated in the related applications included a ratchet. The staple could be incrementally closed with increased ratcheting over increasing number of spurs. The present invention provides two evolved embodiments, which are superior to conventional designs in that the closing mechanisms can withstand much greater force (Newtons) than a small external ratchet. Other improvements will be described below.

FIGS. 14A-B illustrate an embodiment of a posterior lumbar facet staple 500 having a flexure spring 530. As shown in FIGS. 14A-B, the features of the staple 500 include top claws 510 and bottom claws 520 with ridges 570 to help incorporate and fuse with bone. A staple pin (pivot) 560 connects the top claws 510 and bottom claws 520. The staple 500 includes four fastener pins (prongs) 580, 582, 584, 586, two per top claw 510 or bottom claw 520. Ratchet teeth 540 are molded onto the lower claw 520, and a spring loaded ratchet pawl 530 pivots on the claw, and locks the staple 500 in position. As the staple 500 closes, the ratchet 540 works in standard fashion. When a force is applied to open the staple 500, the ratchet 540 locks up, but the ratchet pawl (e.g., the flexure spring) 530 acts as a spring due to its curvature. So depending on the material used for the ratchet spring, the ratchet spring 530 can deform more or less, thereby providing different degrees of resistance. The ratchet mechanism 540 limits the opening force of the staple 500 by a force proportional to the stiffness of the flexure spring 530 (e.g., ratchet pawl). The force can be tailored by making the pawl from different materials or varying the dimension of the flexure spring on the pawl. This embodiment can achieve significant rigidity (stiffness).

FIGS. 15A-C illustrate an embodiment of a posterior lumbar facet staple 600 having a torsional spring 630. FIGS. 15A-C illustrate features of the staple 600, which include top claws 610 and bottom claws 620 with ridges 670 to help incorporate and fuse with bone. A staple pin (pivot) 660 joins the upper claw 610 and lower claw 620 of the staple 600. The staple 600 includes four fastener pins (prongs) 682, 684, 686, 688, two per top claw 610 or bottom claw 620 of the staple 600. The features of the staple 600 include a torsional spring 630, a brake 680, and a pivot spring pin 640. As the staple 600 closes, the ratchet works in standard fashion. When the staple 600 is open, the spring does not interfere with the motion. Once the staple 600 is closed there is a ratchet mechanism (brake) 680 that engages with the spring 630. At that point, the force required to open the staple 600 will depend on the stiffness of the spring 630. Having staple models with different types of springs (e.g., soft, hard, etc.) allows the tailoring of different staples to the needs of a given patient. The embodiments of the present invention have less compliance than the conventional devices.

Figure 16A:
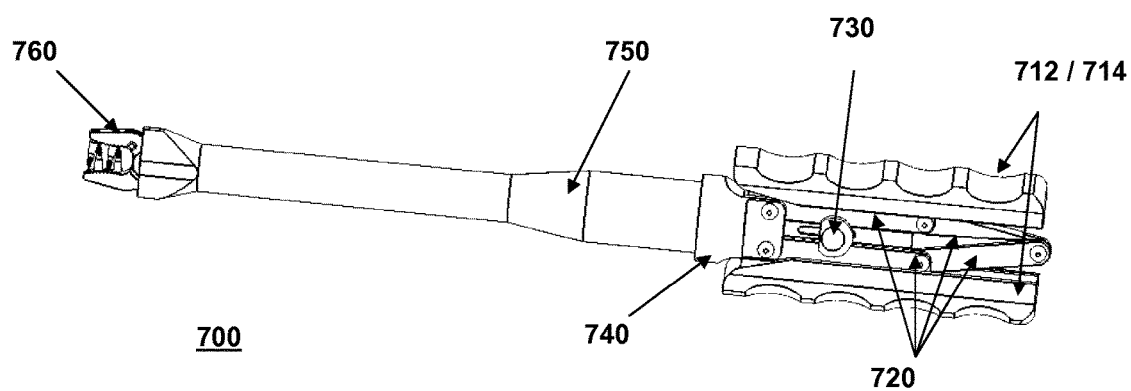
FIGS. 16A-C illustrate an embodiment of a Lumbar facet joint staple gun in side (FIG. 16A), exploded (FIG. 16B) and cross-sectional (FIG. 16C) views.
Figure 16B:
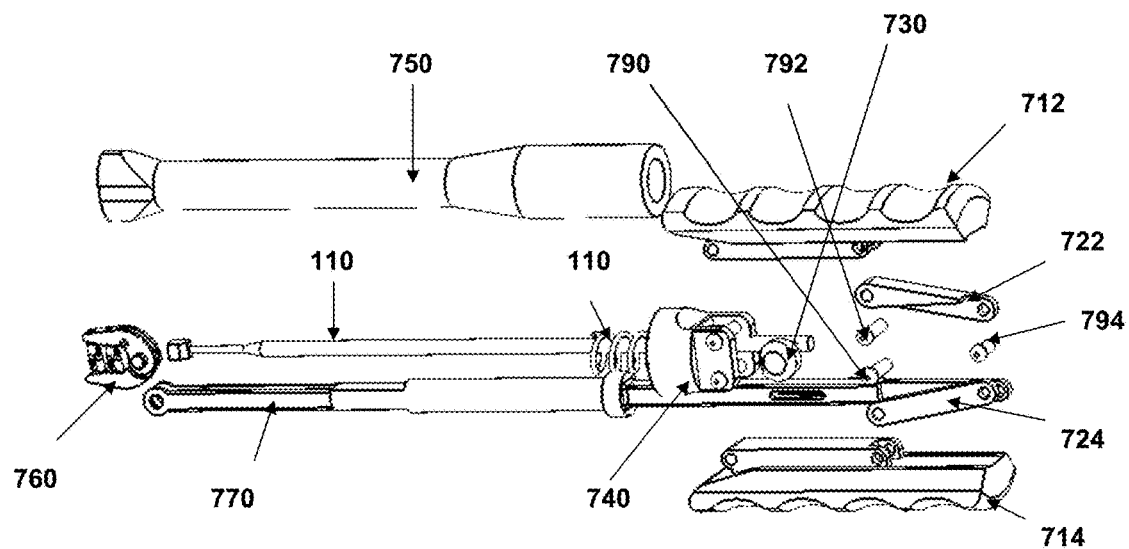
Figure 16C:
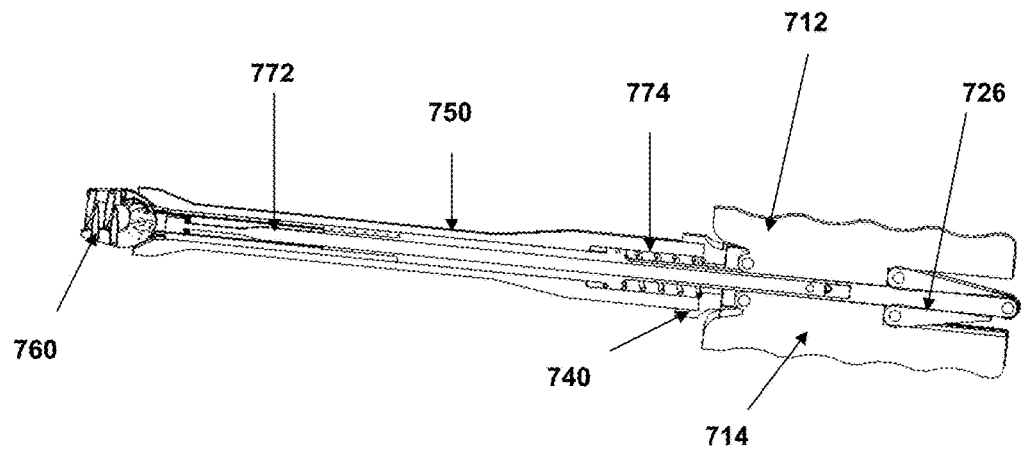
Figure 17A:
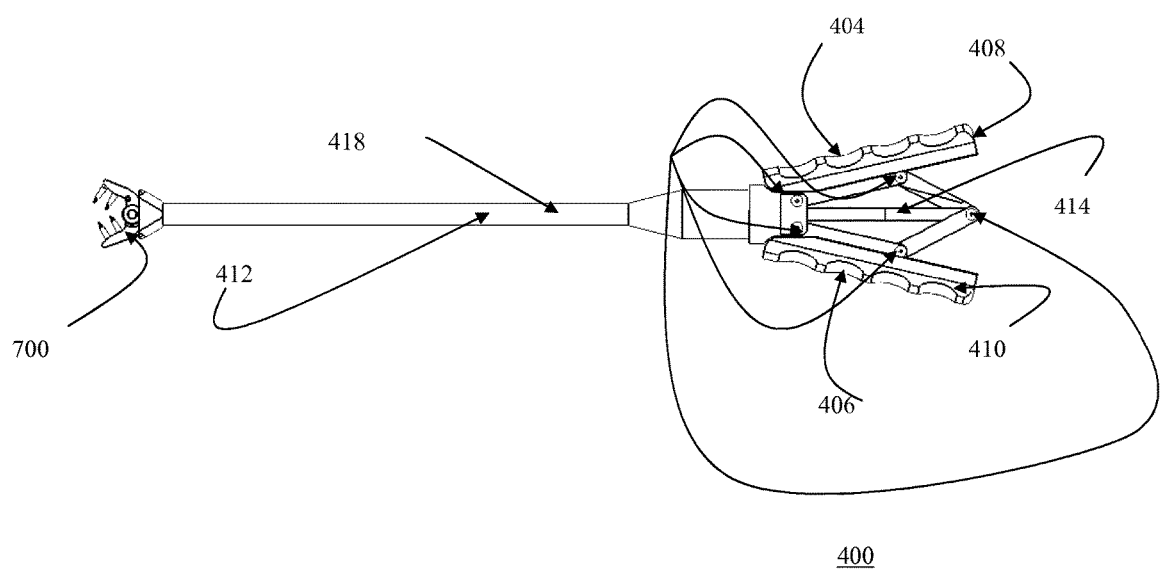
FIGS. 17A-D illustrate an embodiment of a Lumbar facet joint staple gun in side view (FIG. 17A), exploded (FIG. 17B) and cross-sectional (FIG. 17C) and front-on (FIG. 17D) view.
Figure 17B:
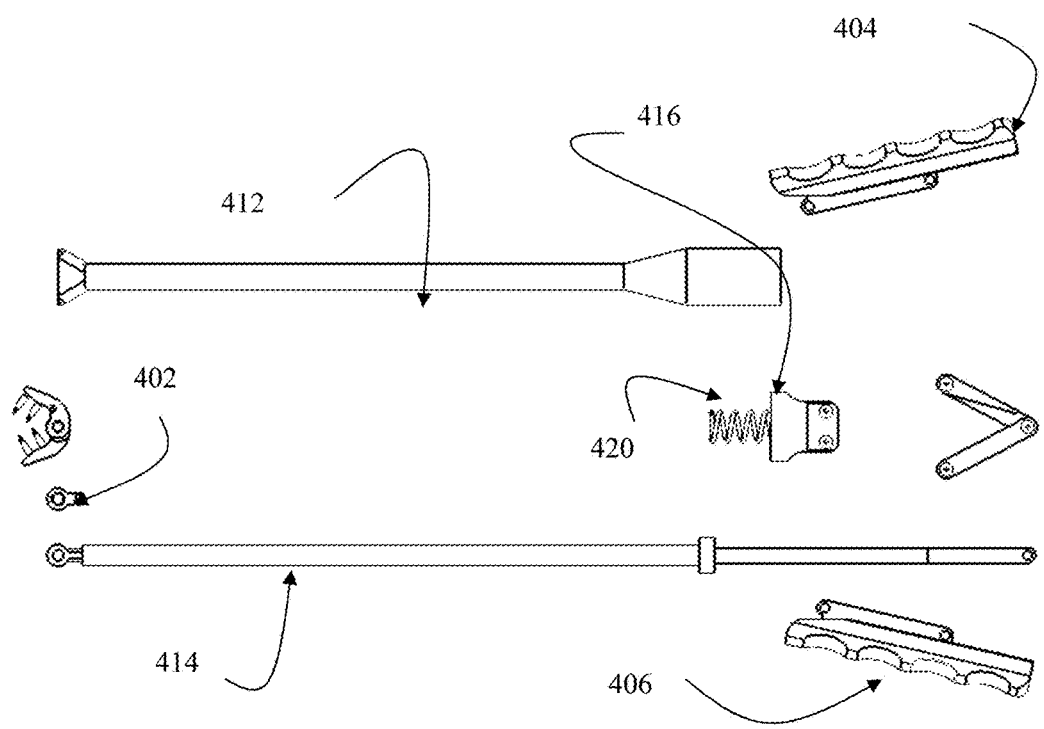
Figure 17C:
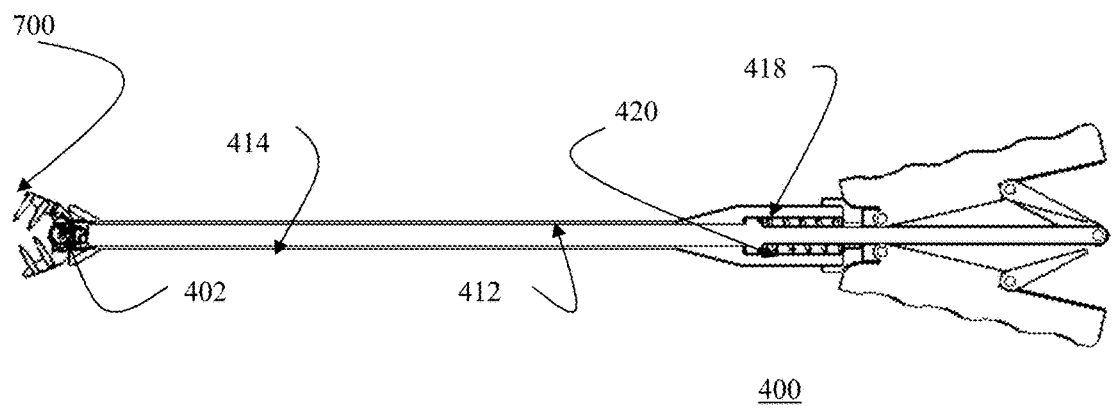
Figure 17D:
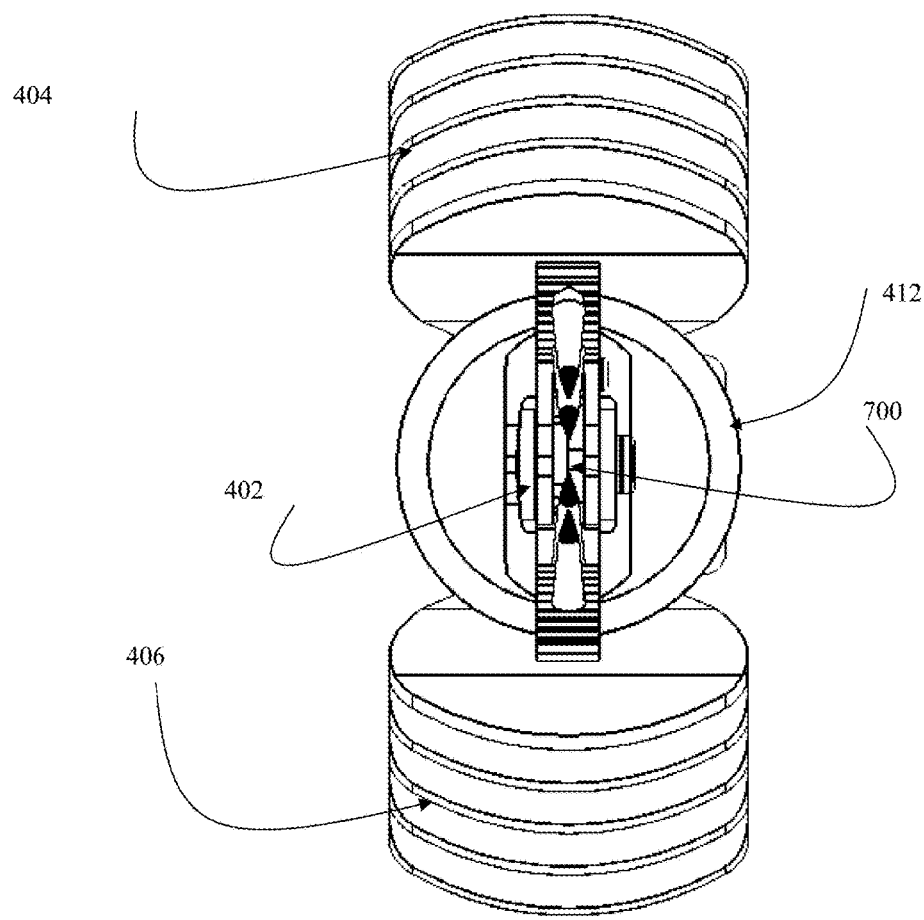

FIGS. 16A-6C illustrate an embodiment of a lumbar facet joint staple gun 700.

Features of lumbar facet joint staple guns have been thoroughly described in the aforementioned related applications, the relevant portions of which are hereby incorporated by reference in their entirety. The exemplary staple gun 700 is an evolutionary advanced version compared to the conventional designs. An improved feature of the staple gun 700 includes a spring return 274 to bring the handles (e.g., upper and lower grips 712, 714) back to their original position after stapling, and a pull knob that opens the staple fingers (e.g., claws) to release the staple 760 at will. The staple 760 in this embodiment is released automatically when it is closed. In addition, a return spring 774 is added to the handles (e.g., upper and lower grips 712, 714) so that the user does not have to reset the stapler manually each time it is used.

The FIGS. illustrate the staple gun 700, which includes two upper and lower grips 712, 714, upper and lower bars 722, 724, a cylinder 750, an opening connector 740, an opening rod 772, an opening lever or pull knob 730, a puller 726, a connector 740, a return spring 774, and pins 790, 792, 794.

6. Surgical Method

Exemplary surgical steps for practicing one or more of the forgoing embodiments will now be described.

The surgical placement of the lumbar facet staples via a posterior facet lumbar staple gun is described in the aforementioned related applications. The surgical procedure for these staple embodiments with this staple gun embodiment is identical to that which has been previously described. The evolutionary advantages of these embodiments are explained above.

The present inventions may provide effective and safe techniques that overcome the problems associated with current transpedicular based cervical, thoracic and lumbar fusion technology, as well as anterior cervical, thoracic and lumbar plating technology, and for many degenerative stable and unstable spinal diseases. These inventions could replace much pedicle screw, and anterior plating based instrumentation in many but not all degenerative spine conditions.

The speed and simplicity of placement of posterior cervical and lumbar facet staples, placement of anterior and posterior lumbar intervertebral cage/BDFT screw constructs, and placement of anterior cervical cage/BDFT screw constructs far exceeds that of current pedicle screw and anterior spinal plating technology. Furthermore, these devices have markedly significantly decreased risk of misguided screw placement and hence decreased risk of neurovascular injury, and blood loss. In the cervical and lumbar spines, intervertebral cage/BDFT screw constructs and facet staples could be applied modularly in different combinations to achieve different degrees of rigidity (flexibility). Furthermore, the posterior cervical and lumbar staple technology is amenable to short same-day procedures performed under local/IV anesthesia with a rapid recovery time. The lumbar and cervical intervertebral cage/BDFT screw constructs all would have decreased recovery time, and more rapid return to work time compared to pedicle screw, and plating technology. These devices with great probability lead to similar if not equal fusion rates, with substantially less morbidity, and hence, overall, make them a major advance in the evolution of spinal instrumented technology leading to advances in the compassionate care of the spinal patient.

7. Exemplary Medical Device

FIGS. 17A-17D illustrate an embodiment of a lumbar facet joint staple gun.

Features of lumbar facet joint staple guns have been thoroughly described in the aforementioned related applications, the relevant portions of which are hereby incorporated by reference in their entirety. The exemplary staple gun 400 is an evolutionary advanced version compared to the conventional designs. The changes incorporated herein facilitate easier insertion and removal of the staple 700 compared to our prior design. An improved feature of the staple gun is the design of an independent puller tip which can be swung open when the stapler is at its maximum open position.

The FIGS. illustrate the staple gun 400 which includes two upper and lower grips 404, 406, upper and lower bars 408, 410, a cylinder 418, a puller 414, a puller tip 402, a connector 418, a return spring 420, and pins 422.

In our previous design the user might have to force the staple hinge to fit into the loops (puller), and once the staple 700 was closed the user had to pry the staple hinge from the loops. To address this problem, one of the loops was made as an independent part which can be swung open when the stapler is at its maximum open position.

The following is the mechanism of its action: The user opens the stapler handles to their maximum. This forces the puller part 414 to stick out from the cylinder part 412. In that configuration, the puller tip 402 can be opened, and the user can insert the staple 700, and close the puller tip 402 (no force required). As the user closes the staple handles, the puller part 414 retracts into the cylinder part 412 which prevents the puller tip part 402 from opening. Thus there is no risk of the staple 700 becoming loose or falling off during surgery. Once the staple 700 has been closed, and is locked, the user can open once more the staple handles to their max to force the puller part out, and in that configuration, the puller tip 402 can be opened, and the staple 700 can be released. The release mechanism doesn't have a spring. The puller tip 402 can simply be opened only when the center shaft (puller) is extended completely. When the puller 414 is retracted (during stapling) the release (puller tip) is constrained by the surrounding geometry i.e. it cannot move. The main advantage of this mechanism is its simplicity. The spring 420 is for the return. The spring 420 pushes the puller out, so after the user staples, by pressing the handles together and pulling the center shaft in (puller), the spring 420 will force the puller 414 out and swing the handles open to reset the stapler.

For example, an aspect of the invention can include a staple gun for a lumbar facet joint staple includes a handle having an upper bar 408 and a lower bar 410, each of the upper bar 408 and the lower bar 410 having a first and a free end, a hollow cylinder 412 body having a first end for receiving the lumbar facet joint staple and a second end adjacent to the handle, a connector 418 having a first end coupled to the hollow cylinder 412 body and a second end coupled to the handle such that the first end of each of the upper bar 408 and the lower bar 410 can be pivotably coupled to the connector 418, a puller 414 disposed in and extending through the hollow cylinder 412 body, wherein the puller 414 has a first end for receiving the lumbar facet joint staple and a second end adjacent to the handle, the second end of the puller 414 being coupled to the handle, and a puller tip 402 coupled to the first end of the puller 414, wherein the handle can be moveable from a closed position to an open position, a distance between the free end of the upper bar 408 and the free end of the lower bar 410 in the closed position being less than a distance between the free end of the upper bar 408 and the free end of the lower bar 410 in the open position, wherein the first end of the puller 414 and at least a part of the puller tip 402 are disposed inside the first end of the hollow cylinder 412 body when the handle is in the closed position, and wherein the first end of the puller 414 and at least a part of the puller tip 402 extend outside the first end of the hollow cylinder 412 body when the handle is in the open.

The puller tip 402 can be moveable between an open position and a closed position when the handle in the open position, and wherein the puller tip 402 is locked in the closed position by the first end of the hollow cylinder 412 body when the handle in the closed position. The puller tip 402 can include a first loop part and a second loop part, the first loop part and the second loop part for grasping sides of the lumbar facet joint staple, wherein the first loop part is movable with respect to the second loop part in a direction transverse to a longitudinal axis of the puller 414. The staple gun can include a spring return mechanism that biases the handle in the open position. The handle can include a linkage coupling the puller 414 to each of the upper bar 408 and the lower bar 410.

Features of cervical facet joint staples have been thoroughly described in the aforementioned related applications, the relevant portions of which are hereby incorporated by reference in their entirety.

More particularly, the lumbar staple has top and bottom claws which come together. The top part of the staple, beneath from where the staple prongs come out, has on either side, a circular protuberance with a hole in the center. A pin goes through this hole and through a hole in the lower staple claw thus connecting these two components which pivot around the pin to open and close the jaw of the staple. The protuberances on both sides of the staple can be fit snugly into the puller tip 402 of the staple gun.

Exemplary aspects of a staple are illustrated in FIGS. 18A-B and 19A-C.

Figure 18A:
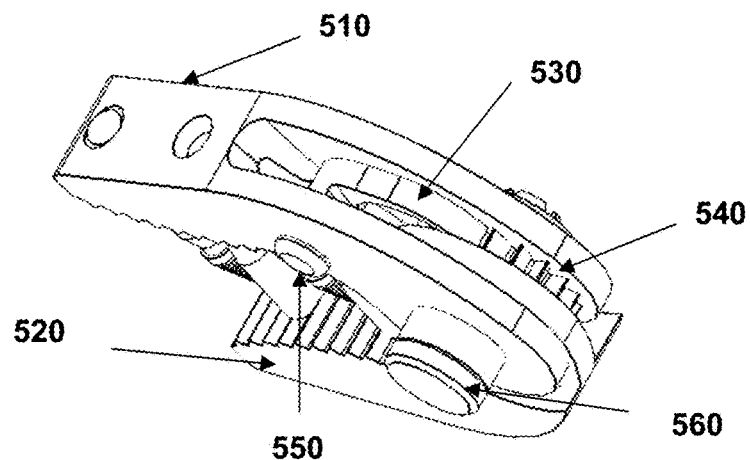
FIGS. 18A-B illustrate an embodiment of a posterior lumbar facet staple, flexure spring embodiment in side isometric (FIG. 18A) and exploded (FIG. 18B) views.
Figure 18B:
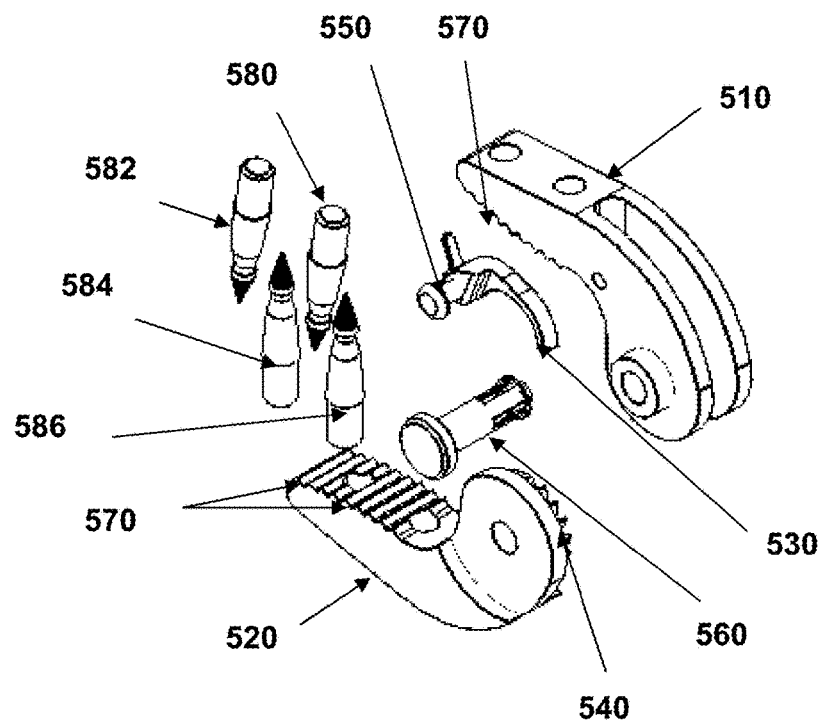
Figure 19A:
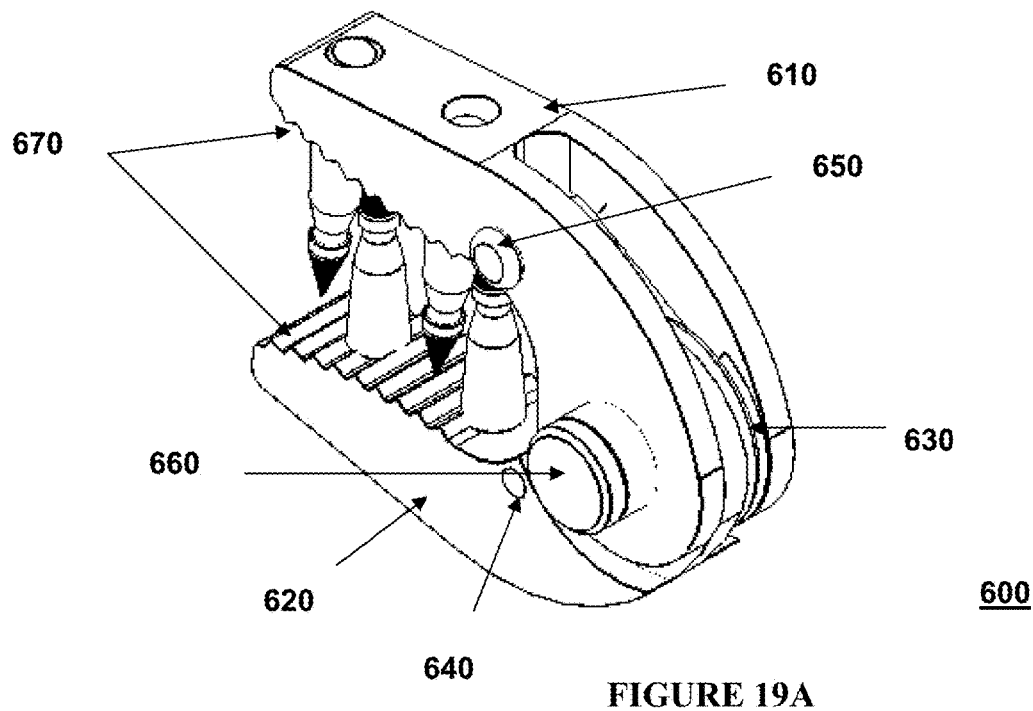
FIGS. 19A-C illustrate an embodiment of a posterior lumbar facet staple, torsional spring embodiment in side isometric (FIG. 19A), bottom isometric (FIG. 19B), and exploded (FIG. 19C) views.
Figure 19B:
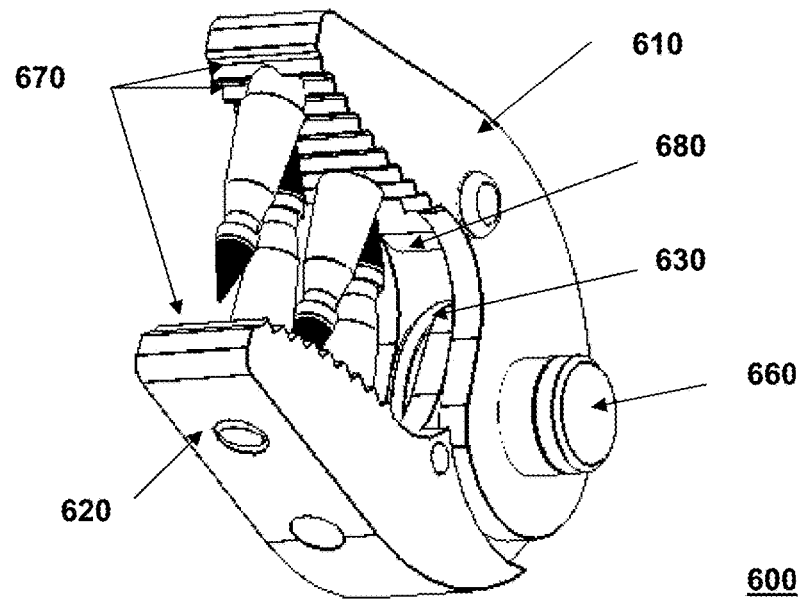
Figure 19C:
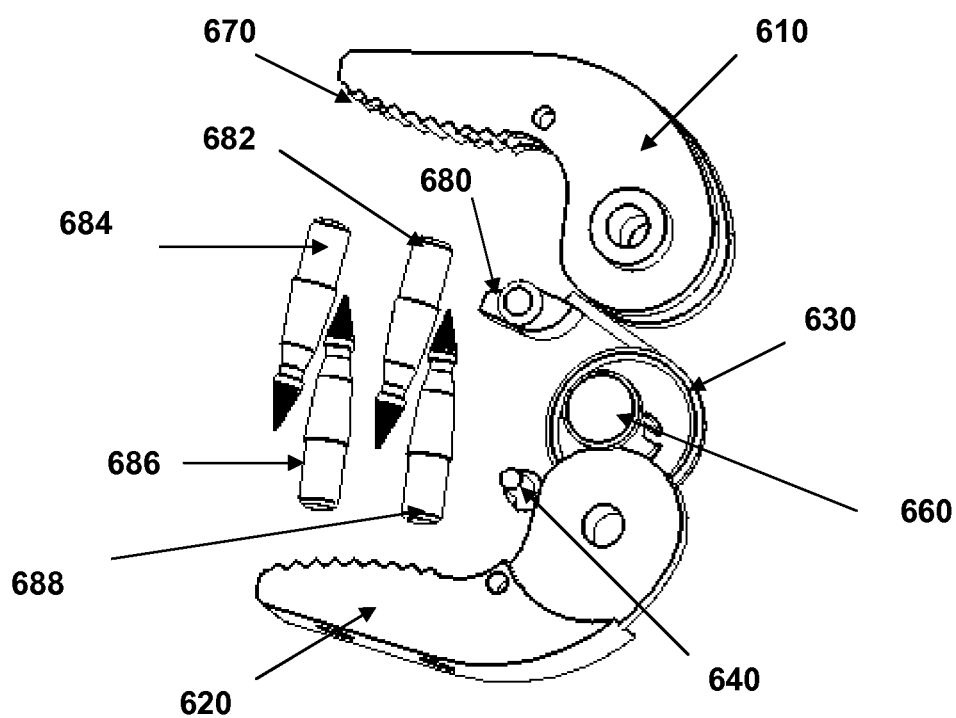

FIGS. 18A-B illustrate an embodiment of a posterior lumbar facet staple having a flexure spring. FIGS. 19A-C illustrate an embodiment of a lumbar facet staple having a torsional spring. Features of a lumbar facet staple have been thoroughly described in the aforementioned related applications, the relevant portions of which are hereby incorporated by reference herein in their entirety. The embodiments illustrated in the related applications included a ratchet. The staple could be incrementally closed with increased ratcheting over increasing number of spurs. The present invention provides two evolved embodiments, which are superior to conventional designs in that the closing mechanisms can withstand much greater force (Newtons) than a small external ratchet. Other improvements will be described below.

FIGS. 18A-B illustrate an embodiment of a posterior lumbar facet staple 500 having a flexure spring 530. As shown in FIGS. 18A-B, the features of the staple 500 include top claws 510 and bottom claws 520 with ridges 570 to help incorporate and fuse with bone. A staple pin (pivot) 560 connects the top claws 510 and bottom claws 520. The staple 500 includes four fastener pins (prongs) 580, 582, 584, 586, two per top claw 510 or bottom claw 520. Ratchet teeth 540 are molded onto the lower claw 520, and a spring loaded ratchet pawl 530 pivots on the claw, and locks the staple 500 in position. As the staple 500 closes, the ratchet 540 works in standard fashion. When a force is applied to open the staple 500, the ratchet 540 locks up, but the ratchet pawl (e.g., the flexure spring) 530 acts as a spring due to its curvature. So depending on the material used for the ratchet spring, the ratchet spring 530 can deform more or less, thereby providing different degrees of resistance. The ratchet mechanism 540 limits the opening force of the staple 500 by a force proportional to the stiffness of the flexure spring 530 (e.g., ratchet pawl). The force can be tailored by making the pawl from different materials or varying the dimension of the flexure spring on the pawl. This embodiment can achieve significant rigidity (stiffness).

FIGS. 19A-C illustrate an embodiment of a posterior lumbar facet staple 600 having a torsional spring 630. FIGS. 19A-C illustrate features of the staple 600, which include top claws 610 and bottom claws 620 with ridges 670 to help incorporate and fuse with bone. A staple pin (pivot) 660 joins the upper claw 610 and lower claw 620 of the staple 600. The staple 600 includes four fastener pins (prongs) 682, 684, 686, 688, two per top claw 610 or bottom claw 620 of the staple 600. The features of the staple 600 include a torsional spring 630, a brake 680, and a pivot spring pin 640. As the staple 600 closes, the ratchet works in standard fashion. When the staple 600 is open, the spring does not interfere with the motion. Once the staple 600 is closed there is a ratchet mechanism (brake) 680 that engages with the spring 630. At that point, the force required to open the staple 600 will depend on the stiffness of the spring 630. Having staple models with different types of springs (e.g., soft, hard, etc.) allows the tailoring of different staples to the needs of a given patient. The embodiments of the present invention have less compliance than the conventional devices.

8. Surgical Method

Exemplary surgical steps for practicing one or more of the forgoing embodiments will now be described.

The surgical placement of the lumbar facet staples via a posterior facet lumbar staple gun (FIG. 17) is described in the aforementioned related applications. The surgical procedure for these staple embodiments with this staple gun embodiment is identical to that which has been previously described. The evolutionary advantages of these embodiments are explained above.

The present inventions may provide effective and safe techniques that overcome the problems associated with current transpedicular based cervical, thoracic and lumbar fusion technology, as well as anterior cervical, thoracic and lumbar plating technology, and for many degenerative stable and unstable spinal diseases. These inventions could replace much pedicle screw, and anterior plating based instrumentation in many but not all degenerative spine conditions.

The speed and simplicity of placement of posterior cervical and lumbar facet staples, placement of anterior and posterior lumbar intervertebral cage/BDFT screw constructs, and placement of anterior cervical cage/BDFT screw constructs far exceeds that of current pedicle screw and anterior spinal plating technology. Furthermore, these devices have markedly significantly decreased risk of misguided screw placement and hence decreased risk of neurovascular injury, and blood loss. In the cervical and lumbar spines, intervertebral cage/BDFT screw constructs and facet staples could be applied modularly in different combinations to achieve different degrees of rigidity (flexibility). Furthermore, the posterior cervical and lumbar staple technology is amenable to short same-day procedures performed under local/IV anesthesia with a rapid recovery time. The lumbar and cervical intervertebral cage/BDFT screw constructs all would have decreased recovery time, and more rapid return to work time compared to pedicle screw, and plating technology. These devices with great probability lead to similar if not equal fusion rates, with substantially less morbidity, and hence, overall, make them a major advance in the evolution of spinal instrumented technology leading to advances in the compassionate care of the spinal patient.

The present invention has been described herein in terms of several preferred embodiments. However, modifications and additions to these embodiments will become apparent to those of ordinary skill in the art upon a reading of the foregoing description. It is intended that all such modifications and additions comprise a part of the present invention to the extent that they fall within the scope of the several claims appended hereto.

What is claimed is:

1. An interarticulating staple for clamping one of a thoracic/lumbar Spinous Process (SP), a thoracic/lumbar Transverse Process (TP), and cervical Spinous Process (SP), the interarticulating staple comprising:

a first claw;
a second claw, wherein each of the first claw and the second claw includes a clamping surface having at least one of a plurality of ridges and a plurality of prongs, wherein a first clamping surface is opposed to a second clamping surface and wherein each of the first clamping surface and the second clamping surface has a concave surface;
a staple pin pivotally connecting the first claw and the second claw; and
a ratchet mechanism that limits an opening force of the first claw with respect to the second claw.

2. The staple according to claim 1, wherein the ratchet mechanism comprises:
a ratchet pin pivotably mounted to the second claw,
wherein the first claw includes a plurality of ratchet teeth, and
wherein the ratchet pin includes a flexure spring engaging the plurality of ratchet teeth.

3. The staple according to claim 1, wherein the clamping surface of the first claw includes the plurality of prongs, and wherein one of the plurality of prongs includes a perforation.

4. The staple according to claim 1, wherein the clamping surface of the first claw includes the plurality of prongs, and wherein one of the plurality of prongs includes a plurality of perforations.

5. The staple according to claim 1, wherein the clamping surface of the first claw includes the plurality of prongs, and wherein each of the plurality of prongs includes a perforation.

6. The staple according to claim 1, wherein the first claw and the second claw each include a portion having a staple pin opening,
wherein the portion having the staple pin opening of the first claw overlaps the portion having the staple pin opening of the second claw, and
wherein the staple pin engages the staple pin opening of the first claw and the second claw to pivotally connect the first claw to the second claw.

7. The staple according to claim 6, wherein the portion having the staple pin opening of each of the first claw and the second claw includes claw teeth, and
wherein the claw teeth of the first claw interdigitate with the claw teeth of the second claw.

8. The staple according to claim 1, wherein the clamping surface of the first claw opposes the clamping surface of the second claw.

9. The staple according to claim 1, wherein the ratchet mechanism comprises:
a ratchet pawl pivotably mounted to the first claw,
wherein the second claw includes a plurality of ratchet teeth, and
wherein a portion of the ratchet pawl engages the plurality of ratchet teeth to fix a position of the first claw with respect to the second claw.

10. The staple according to claim 9, wherein the ratchet pawl is pivotably mounted to the first claw by a ratchet bolt.

11. The staple according to claim 1, wherein the ratchet mechanism prevents an opening movement of the first claw with respect to the second claw in the opening direction at a plurality of positions.

12. The staple according to claim 1, wherein the staple is a cervical Spinous Process (SP) staple configured to clamp a cervical Spinous Process (SP),
wherein each of the first claw and the second claw are T-shaped.

13. The staple according to claim 1, wherein each of the first claw and the second claw includes:
a first portion extending in a longitudinal direction from a proximal end to a distal end, the proximal end of each of the first claw and the second claw having a staple pin opening; and
a clamping surface at the distal end of the first portion, wherein the clamping surface extends away from the distal end of the first portion in a direction perpendicular to the longitudinal direction of the first portion.

14. The staple according to claim 13, wherein the clamping surface of each of the first claw and the second claw includes:
the plurality of prongs, wherein the plurality of prongs is separated into a first group of prongs and a second group of prongs, wherein the first group of prongs on each of the first claw and the second claw is separated from the second group of prongs on each of the first claw and the second claw by a first distance that is equal to an inter-lumbar cervical Spinous Process (SP) distance such that the first and second claws will engage and perforate adjacent Spinous Processes.

15. The staple according to claim 13, wherein the clamping surface of the first claw includes a plurality of prongs, wherein the plurality of prongs of the first claw is separated into a first group of prongs and a second group of prongs, wherein the first group of prongs on the first claw is separated from the second group of prongs on the first claw by a first distance, and
wherein the clamping surface of the second claw includes a plurality of prongs, wherein the plurality of prongs of the second claw is separated into a third group of prongs and a fourth group of prongs, wherein the third group of prongs on the second claw is separated from the fourth group of prongs on the second claw by a second distance.

16. The staple according to claim 1, wherein the ratchet mechanism limits the opening force of the first claw with respect to the second claw at a fully open position, a fully closed position, and an intermediate position between the fully open position and the fully closed position.

17. The staple according to claim 1, wherein the clamping surface of each of the first claw and the second claw includes both the plurality of ridges and the plurality of prongs.

18. The staple according to claim 1, wherein the clamping surface includes the plurality of prongs, and
wherein the plurality of prongs includes at least one of a solid, straight prong and a solid, curved prong.

19. The staple of claim 1, wherein the ratchet mechanism comprises a flexure spring and a plurality of ratchet teeth.

20. An interarticulating staple for clamping one of a thoracic/lumbar Spinous Process (SP), a thoracic/lumbar Transverse Process (TP), and cervical Spinous Process (SP), the interarticulating staple comprising:
a first claw;
a second claw, wherein each of the first claw and the second claw includes a clamping surface having at least one of a plurality of ridges and a plurality of prongs;
a staple pin pivotally connecting the first claw and the second claw; and
a ratchet mechanism that limits an opening force of the first claw with respect to the second claw, wherein the ratchet mechanism comprises:
a ratchet pin pivotably mounted to the first claw,
wherein the second claw includes a plurality of ratchet teeth, and wherein the ratchet pin includes a flexure spring engaging the plurality of ratchet teeth.

21. The staple according to claim 20, wherein the ratchet pin is pivotably mounted to the first claw by a ratchet bolt.

22. A method of clamping one of a thoracic/lumbar Spinous Process (SP), a thoracic/lumbar Transverse Process (TP), and cervical Spinous Process (SP), the method comprising:

positioning an interarticulating staple on a pair of adjacent spinous processes, wherein the interarticulating staple comprises:

a first claw having a first clamping surface extending from a first proximal end of the first claw to a first distal end of the first claw and a second claw having a second clamping surface extending from a second proximal end of the second claw to a second distal end of the second claw, wherein the first clamping surface and the second clamping surface cooperate to clamp the pair of adjacent spinous processes between the first and second clamping surfaces when the first claw and the second claw are in a closed position;

a staple pin pivotally connecting the first claw and the second claw; and a ratchet mechanism that limits an opening force of the first claw with respect to the second claw; and securing the interarticulating staple to the pair of adjacent spinous processes by clamping the first clamping surface and the second clamping surface to the pair of adjacent spinous processes.

23. The method of claim 22, wherein the ratchet mechanism comprise a flexure spring and a plurality of ratchet teeth.

24. An interarticulating staple for clamping one of a thoracic/lumbar Spinous Process (SP), a thoracic/lumbar Transverse Process (TP), and cervical Spinous Process (SP), the interarticulating staple comprising:

a first claw;

a second claw, wherein each of the first claw and the second claw includes a clamping surface having at least one of a plurality of ridges and a plurality of prongs;

a staple pin pivotally connecting the first claw and the second claw; and a ratchet mechanism that limits an opening force of the first claw with respect to the second claw, wherein the clamping surface includes the plurality of prongs, and wherein the plurality of prongs includes at least one of a perforated, straight prong configured to hold bone/biological fusion promoters to facilitate fusion and a perforated, curved prong configured to hold the bone/biological fusion promoters to facilitate the fusion.

25. The staple of claim 24, wherein the ratchet mechanism comprises a flexure spring and a plurality of ratchet teeth.

* * * * *

UNITED STATES PATENT AND TRADEMARK OFFICE
CERTIFICATE OF CORRECTION

PATENT NO. : 10,098,672 B2
APPLICATION NO. : 14/337210
DATED : October 16, 2018
INVENTOR(S) : Mosheh T. Moskowitz et al.

Page 1 of 2

It is certified that error appears in the above-identified patent and that said Letters Patent is hereby corrected as shown below:

On the Title Page

Column 1, Line 1 (Related U.S. Application Data): Delete "Continuation" and insert
-- Continuation-in-part --, therefor.

Page 2, Column 1, Line 3 (Related U.S. Application Data): Delete "continuation" and insert
-- continuation-in-part --, therefor.

Page 2, Column 1, Lines 11-39 (Related U.S. Application Data): After "8,734,516," delete "application No. 14/337,210, which is a continuation of application No. 13/101,135, filed on May 4, 2011, now Pat. No. 9,675,385, which is a continuation-in-part of application No. 12/054,335, filed on Mar. 24, 2008, now Pat. No. 7,972,363, which is a continuation-in-part of application No. 11/842,855, filed on Aug. 21, 2007, now Pat. No. 7,942,903, application No. 14/337,210, which is a continuation of application No. 13/101,135, filed on May 4, 2011, now Pat. No. 9,675,385, which is a continuation-in-part of application No. 11/842,855, filed on Aug. 21, 2007, now Pat. No. 7,942,903, application No. 14/337,210, which is a continuation of application No. 13/101,135, filed on May 4, 2011, now Pat. No. 9,675,385, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279, application No. 14/337,210, which is a continuation of application No. 13/101,135, filed on May" 4, 2011, now Pat. No. 9,675,385, which is a continuation-in-part of application No. 11/208,644, filed on Aug. 23, 2005, now Pat. No. 7,704,279, application No. 14/337,210, which is a continuation of application No. 13/101,135, filed on May 4, 2011, now Pat. No. 9,675,385, application No. 14/337,210, which is a continuation of application No. 13/101,135, filed on May 4, 2011, now Pat. No. 9,675,385,".

Page 2, Column 1, Line 40 (Related U.S. Application Data): After "14/337,210," delete "which".

Page 2, Column 1, Line 40 (Related U.S. Application Data): Delete "continuation" and insert
-- continuation-in-part --, therefor.

Signed and Sealed this
Second Day of July, 2019

Andrei Iancu
*Director of the United States Patent and Trademark Office*

Page 2, Column 1, Line 42 (Related U.S. Application Data): Delete "continuation" and insert -- continuation-in-part --, therefor.

In the Claims

Column 30, Line 4: In Claim 23, delete "comprise" and insert -- comprises --, therefor.